United States Patent [19]

Ingolia et al.

[11] Patent Number: 4,885,251
[45] Date of Patent: Dec. 5, 1989

[54] RECOMBINANT DNA EXPRESSION VECTORS AND DNA COMPOUNDS WHICH ENCODE ISOPENICILLIN N SYNTHETASE

[75] Inventors: Thomas D. Ingolia; Stephen W. Queener; Suellen M. Samson, all of Indianapolis; Paul L. Skatrud; Otis W. Godfrey, both of Greenwood, all of Ind.

[73] Assignee: Eli Lilly and Company, Indianapolis, Ind.

[21] Appl. No.: 895,008

[22] Filed: Aug. 8, 1986

Related U.S. Application Data

[63] Continuation-in-part of Ser. No. 799,384, Nov. 18, 1985, abandoned, which is a continuation-in-part of Ser. No. 725,870, Apr. 22, 1985, abandoned.

[51] Int. Cl.[4] .................... C12N 9/00; C12N 15/00; C12P 1/02; C12P 1/04
[52] U.S. Cl. .................... 435/183; 435/172.3; 435/252.2; 435/252.3; 435/252.33; 435/252.35; 435/254; 435/320; 536/27; 935/14; 935/27; 935/34; 935/60; 935/68; 935/72
[58] Field of Search .................... 435/68, 91, 169, 170, 435/171, 172.3, 183, 252.1, 252.2, 252.3, 252.33, 252.35, 254, 320, 849, 872, 886, 925, 986, 933, 935; 935/6, 22, 27, 36, 60, 68, 72; 536/27

[56] References Cited

U.S. PATENT DOCUMENTS

| | | | |
|---|---|---|---|
| 4,178,210 | 12/1979 | Demain et al. | 435/47 |
| 4,307,192 | 12/1981 | Demain et al. | 435/47 |
| 4,588,585 | 5/1986 | Mark et al. | 424/85.2 |
| 4,618,578 | 10/1986 | Burke et al. | 435/68 |

FOREIGN PATENT DOCUMENTS 84304856.2 7/1984 European Pat. Off. .
85306765.0 9/1984 European Pat. Off. .

OTHER PUBLICATIONS

Kaster et al., 1983 *NAR*, 11:6895.
Van Solingen et al., 1985, *J. Cell. Biochem.*, Suppl. 9C:(Abstr. 1576), 174.
Peñalva et al., 1985, *J. Cell. Biochem.*, Suppl. 9C:(Abstr. 1570), 172.
Dalbodie-McFarland et al., 1982, *PNAS*, 79:6409–6413.
Suggs et al., 1981, *PNAS*, 78:6613.
Pang et al., 1984, *Biochem. J.*, 222:789.
Skatrud et al., 1984, *Current Genetics*, 8:155.
S. W. Queener and Norbert Neuss, The Chemistry and Biology of β-Lactam Antibiotics, vol. 3, Chapter 1, (1982, Academic Press, Inc.).

(List continued on next page.)

*Primary Examiner*—Elizabeth C. Weimar
*Assistant Examiner*—Richard C. Peet
*Attorney, Agent, or Firm*—Ron K. Levy; Leroy Whitaker

[57] ABSTRACT

The present invention comprises novel DNA compounds that encode isopenicillin N synthetase and also comprises related methods, transformants, and polypeptides. The novel isopenicillin N synthetase-encoding DNA, together with its associated transcriptional and translational activating sequence, was isolated from *Cephalosporium acremonium* and cloned into an *E. coli* cloning vector. The isopenicillin N synthetase-encoding DNA has been used to construct novel *E. coli* expression vectors that drive expression of a stable, active, and novel isopenicillin N synthetase in *E. coli*. The intact *C. acremonium* isopenicillin N synthetase-encoding DNA and associated transcriptional and translational activating sequence have also been used to construct *C. acremonium* expression vectors that drive expression of the isopenicillin N synthetase in *C. acremonium*. The *C. acremonium* transcriptional and translational activating sequence has further been fused to a hygromycin phosphotransferase-encoding DNA segment and placed onto *C. acremonium* expression vectors. Useful derivatives of the novel compounds and vectors are also described.

65 Claims, 23 Drawing Sheets

OTHER PUBLICATIONS

Wolfe et al., 1984, Science, 226:1386.

Jeffrey T. Fayerman, Abstract of an Oral Presentation entitled "Protein Engineering" at the 4th Stony Brook Symposium on Molecular Biology, May 20–22, 1985.

Skatrud et al., Abstract of an Oral Presentation entitled, "The Application of Recombinant DNA Technology to the Antibiotic Producing Filamentous Fungus *Cephalosporium acremonium*" at the 4th Annual Toyobo Biotechnology Foundation Symposium, Tokyo, Japan, Aug. 30–31, 1985.

Thomas D. Ingolia, a Poster Session at a Meeting of the International Union of Pure & Applied Chemistry, Manchester, England, Sep. 8–13, 1985.

Jerry L. Chapman, Abstract of an Oral Presentation at the 1985 Annual Meeting of the Society for Industrial Microbiology, Boston, Mass., Aug. 3–9, 1985.

Samson et al., 1985, Nature, 318:191–194.

Juarin and Grundstrom, 1981, Proc. Natl. Acad. Sci., 78(8):4897–4901.

Restriction Site and Function Map of
Plasmid pIT335
(8.24 kb)

Restriction Site and Function Map of
Plasmid pCZ106
(10.8 kb)

Restriction Site and Function Map of
Plasmid pIT337
(11.8 kb)

Restriction Site and Function Map of Plasmid pIT221 (8.04 kb)

Restriction Site and Function Map of
Plasmid pPS20
(11 kb)

Restriction Site and Function Map of
Plasmid pPS19
(7.85 kb)

Restriction Site and Function Map of
Plasmid pPS21
(8.5 kb)

Restriction Site and Function Map of
Plasmid pPS21A
(8.5 kb)

Restriction Site and Function Map of
Plasmid pPS25
(8.71 kb)

Restriction Site and Function Map of Plasmid pPS28 (6.6 kb)

Restriction Site and Function Map of Plasmid pPS29
(6.1 kb)

Restriction Site and Function Map of
Plasmid pPS26
(11.6 kb)

Restriction Site and Function Map of
Plasmid pPS34
(8.7 kb)

Restriction Site and Function Map of
Plasmid pIT336
(4.1 kb)

Restriction Site and Function Map of
Plasmid pPS35
(4.1 kb)

Restriction Site and Function Map of
Plasmid pPS27
(5.5 kb)

Restriction Site and Function Map of
Plasmid pPS37
(6.4 kb)

Restriction Site and Function Map of
Plasmid pMLC12
(2.67 kb)

Restriction Site and Function Map of
Plasmid pPS48
(7 kb)

Restriction Site and Function Map of
Plasmid pPS47
(8 kb)

Restriction Site and Function Map of
M13mp19 Phage mIT110
(9.92 kb)

Restriction Site and Function Map of
Plasmid pKC309
(6.82 kb)

Restriction Site and Function Map of
Plasmid pIT344WT
(9.3 kb)

RECOMBINANT DNA EXPRESSION VECTORS AND DNA COMPOUNDS WHICH ENCODE ISOPENICILLIN N SYNTHETASE

CROSS REFERENCE TO RELATED APPLICATIONS

This application is a continuation-in-part of U.S. patent application Ser. No. 799,384, filed Nov. 18, 1985, now abandoned which is a continuation-in-part of U.S. patent application Ser. No. 725,870, filed Apr. 22, 1985.

SUMMARY OF THE INVENTION

The present invention comprises a DNA sequence encoding isopenicillin N synthetase activity. Isopenicillin N synthetase catalyzes the reaction in which isopenicillin N is formed from δ-(L-α-aminoadipyl)-L-cysteinyl-D-valine. This reaction is a critical step in the biosynthesis of important antibiotics such as penicillins from *Penicillium chrysogenum*, *Cephalosporium acremonium*, and *Streptomyces clavuligerus*; cephalosporins from *C. acremonium*; and 7α-methoxycephalosporins from *S. clavuligerus*.

The novel DNA sequence which encodes the isopenicillin N synthetase activity was isolated from *Cephalosporium acremonium* and has been used to construct recombinant DNA expression vectors that drive expression of the activity. Two types of these expression vectors are especially useful. The first type of vector drives high-level expression of the isopenicillin N synthetase activity in *E. coli*, and the second type drives expression of the activity in *Cephalosporium acremonium*.

The *E. coli*-produced isopenicillin N synthetase activity has been shown in vitro tests to form isopenicillin N from δ-(L-α-aminoadipyl)-L-cysteinyl-D-valine. Crude cell extracts from *E. coli* transformed with the *E. coli* vectors of the present invention exhibited isopenicillin N synthetase activity without any prior activation treatment. The *E. coli* vectors of the present invention thus provide an efficient means for obtaining large amounts of active isopenicillin N synthetase. Isopenicillin N synthetase is useful, not only for the production of isopenicillin N, but also for the condensation of tripeptides other than δ-(L-α-aminoadipyl)-L-cysteinyl-D-valine to form novel antibiotics.

The Cephalosporium vectors of the present invention are useful for purposes of strain improvement. Cephalosporium is an economically important organism useful in the production of penicillin and cephalosporin antibiotics. Transformation of Cephalosporium with certain recombinant DNA expression vectors of the present invention will result in higher in vivo levels of isopenicillin N synthetase in the transformants, which thus exhibit increased efficiency and yield of fermentations involving these transformants.

The DNA compounds encoding isopenicillin N synthetase are readily modified to construct expression vectors which increase the efficiency and yield of fermentations involving other organisms, such as *Penicillium chrysogenum* and *Streptomyces clavuligerus*. Although the isopenicillin N synthetase-encodeing DNA of the present invention was isolated from *Cephalosporium acremonium*, the present DNA compounds can be used to construct vectors which drive expression of isopenicillin N synthetase activity in a wide variety of host cells, as the *E. coli* vectors of the present invention illustrate. All organisms that produce penicillins and cephalosporins utilize the common precursors δ-(L-α-aminoadipyl)-L-cysteinyl-D-valine and isopenicillin N. Therefore, the isopenicillin N synthetase-encoding DNA compounds of the present invention can be used to produce vectors useful for improving efficiency and yield of fermentations involving penicillin and cephalosporin antibiotic-producing organisms of all genera.

The DNA compounds of the present invention are derived from genomic DNA of *Cephalosporium acremonium* and are significantly homologous in nucleotide sequence to the DNA compounds encoding isopenicillin N synthetase activity in *Streptomyces clavuligerus*, *Penicillium chrysogenum*, and other isopenicillin N synthetase producing organisms. Because of this homology, the isopenicillin N synthetase-encoding DNA compounds of the present invention can be labelled and used to screen genomic libraries of organisms that produce isopenicillin N or similar compounds for the presence of isopenicillin N synthetase-type enzymes. Many organisms comprise DNA that encodes an isopenicillin N synthetase activity substantially equivalent to the activity encoded by the DNA compounds of the present invention, and the present invention comprises those equivalent DNA compounds.

The isopenicillin N synthetase-encoding DNA compounds of the present invention were derived from *Cephalosporium acremonium* genomic DNA and were isolated in conjunction with the transcriptional and translational activating sequence that controls the expression of the *C. acremonium* isopenicillin N synthetase-encoding genomic DNA. The present invention also comprises this novel transcriptional and translational activating sequence, which has been used, as disclosed herein, to drive expression of heterologous genes in *C. acremonium*.

The present invention also comprises the regulatory signals of the IPS gene that are located at the 3' end of the coding strand of the coding region of the IPS gene. These 3' regulatory sequences encode the transcription termination and mRNA polyadenylation and processing signals of the IPS gene. The presence of these signals in the proper position, which is at the 3' end of the coding strand of the coding region of the gene to be expressed, in an expression vector enhances expression of the desired product encoded by the vector in *Cephalosporium acremonium*.

The following section provides a more detailed description of the present invention. For purposes of clarity and as an aid in the understanding of the present invention, as disclosed and claimed herein, the following items are defined below.

AmR—the apramycin resistance-conferring gene.

Antibiotic—a substance produced by a microorganism that, either naturally or with limited chemical modification, will inhibit the growth of or kill another microorganism or eukaryotic cell.

Antibiotic Biosynthetic Gene—a DNA segment that encodes an enzymatic activity which is necessary for an enzymatic reaction in the process of converting primary metabolites into antibiotics.

Antibiotic-Producing Organism—any organism, including, but not limited to, Streptomyces, Bacillus, Monospora, Cephalosporium, Podospora, Penicillium, and Nocardia, that either produces an antibiotic or contains genes that, if expressed, would produce an antibiotic.

Antibiotic Resistance-Conferring Gene—a DNA segment that encodes an activity that confers resistance to an antibiotic.

ApR—the ampicillin resistance-conferring gene.

Bifunctional Cloning Shuttle Vector—a recombinant DNA cloning vector that can replicate and/or integrate into organisms of two different taxa.

Cat—the chloramphenicol resistance-conferring gene.

Ceph DNA—DNA from *Cephalosporium acremonium*

Ceph ori—*Cephalosporium acremonium* mitochondrial DNA that provides for extra chromosomal maintenance of a recombinant DNA vector.

Cloning—the process of incorporating a segment of DNA into a recombinant DNA cloning vector.

cos—phage λ cohesive end sequences.

Cosmid—a recombinant DNA cloning vector that can replicate in a host cell in the same manner as a plasmid but that can also be packed into phage heads.

Functional Polypeptide—a recoverable bioactive entirely heterologous or homologous polypeptide or precursor, a recoverable bioactive polypeptide comprising a heterologous polypeptide and a portion or whole of a homologous polypeptide or a recoverable bioinactive fusion polypeptide comprising a heterologous polypeptide and a bioinactivating homologous polypeptide which can be specifically cleaved.

Genomic Library—a set of recombinant DNA cloning vectors into which segments of DNA, which substantially represent the entire genome of a particular organism, have been cloned.

HmR—the hygromycin resistance-conferring gene.

Hybridization—the process of annealing two homologous single-stranded DNA molecules to form a double-stranded DNA molecule, that may or may not be completely base paired.

IPS—isopenicillin N synthetase or isopenicillin N synthetase-encoding DNA.

IPSp—the transcriptional and translational activating sequence of the isopenicillin N synthetase (IPS) gene of *Cephalosporium acremonium*.

IPSt—the transcription termination and mRNA polyadenylation and processing signals of the IPS gene.

Isopenicillin N Synthetase—an enzyme, also known as cyclase, that catalyzes the formation of isopenicillin N from δ-(L-α-aminoadipyl)-L-cysteinyl-D-valine.

KmR—the kanamycin resistance-conferring gene.

M13 ori—the origin of replication of phage M13.

mel—the tyrosinase gene.

mRNA—messenger ribonucleic acid.

PGK—the transcriptional and translational activating sequence of the yeast *Saccharomyces cerevisiae* phosphoglycerate kinase gene.

Recombinant DNA Cloning Vector—any autonomously replicating or integrating agent, including, but not limited to, plasmids, comprising a DNA molecule to which one or more additional DNA molecules can be or have been added.

Recombinant DNA Expression Vector—any autonomously replicating or integrating agent, including, but not limited to, plasmids, comprising a transcriptional and translational activating sequence positioned to drive expression of a DNA segment that encodes a polypeptide or RNA of research or commercial interest.

Recombinant DNA Vector—any recombinant DNA cloning or expression vector.

Restriction Fragment—any linear DNA molecule generated by the action of one or more enzymes.

rRNA—ribosomal ribonucleic acid.

Sensitive Host Cell—a host cell that cannot grow in the presence of a given antibiotic without a DNA segment that confers resistance thereto.

TcR—the teracycline resistance-conferring gene.

Transcriptional Activating Sequence—a DNA sequence that promotes transcription of DNA.

Transfectant—a recipient host cell that has undergone transformation by phage DNA.

Transformant—a recipient host cell that has undergone transformation.

Transformation—the introduction of DNA into a recipient host cell that changes the genotype and results in a change in the recipient cell.

Translational activating sequence—a DNA sequence that, when translated into mRNA, promotes translation of mRNA into protein.

trp—the transcriptional and translational activating sequence of the tryptophan operon of *E. coli*.

BRIEF DESCRIPTION OF THE FIGURES

The restriction site and function maps presented in FIGS. 1–23 are approximate representations of the recombinant DNA vectors discussed herein. The spacing of restriction sites on the map is proportional to the actual spacing of the restriction sites on the vector, but observed restriction site distances may vary somewhat from calculated map distances. The restriction site information is not exhaustive; therefore, there may be more restriction sites of a given type on the vector than actually shown on the map.

DETAILED DESCRIPTION OF THE INVENTION

Figure 1:
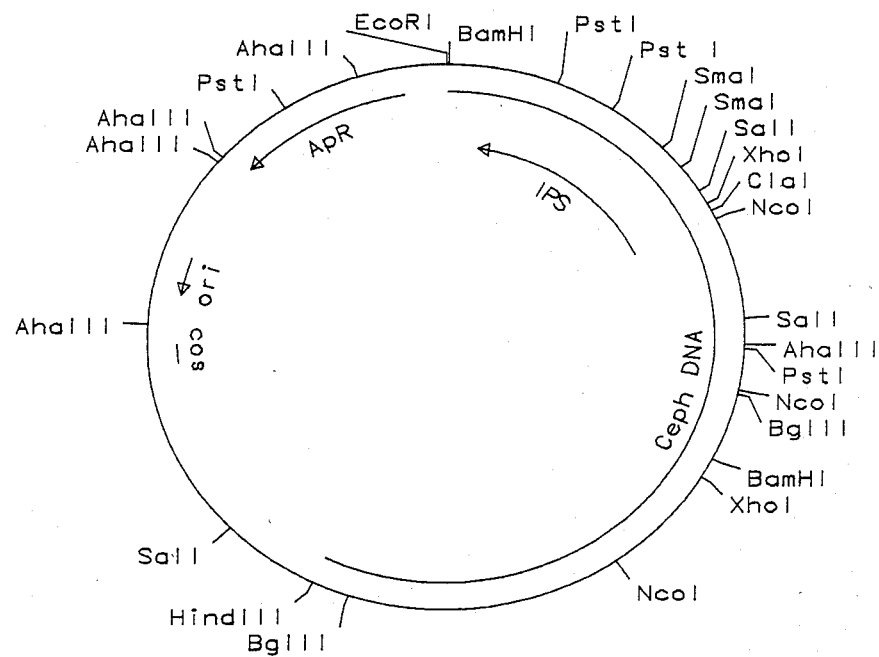
FIG. 1. A restriction site and function map of plasmid pIT335.

The present invention comprises DNA compounds and recombinant DNA cloning nd expression vectors which encode isopenicillin N synthetase activity. A particular DNA sequence encoding isopenicillin N synthetase activity is shown below. In the depiction, only the "sense" or coding strand of the double-stranded DNA molecule is shown, and the DNA is depicted from left to right in the 5'→3' orientation. The nucleotide sequence is numbered; the numbers appear above the DNA sequence. Immediately below each line of DNA sequence, the amino acid residue sequence of the isopenicillin N synthetase encoded by the DNA is listed from left to right in the amino-terminus→carboxy-terminus direction. Each amino acid residue appears below the DNA that encodes it. The amino acid residue sequence is numbered; the numbers appear below the amino acid residue sequence.

DNA Sequence Encoding Isopenicillin N Synthetase Activity and Corresponding Amino Acid Sequence

| | 10 | 20 | 30 | 40 |
|---|---|---|---|---|
| 5'-ATG GGT TCC | GTT CCA GTT | CCA GTG GCC | AAC GTC CCC CGA | ATC GAT GTC |
| MET GLY SER | VAL PRO VAL | PRO VAL ALA | ASN VAL PRO ARG | ILE ASP VAL |
| | 5 | | 10 | 15 |
| 50 | 60 | 70 | 80 | 90 |
| TCG CCC CTA | TTC GGC GAT | GAC AAG GAG | AAG AAG CTC GAG | GTA GCT CGC |
| SER PRO LEU | PHE GLY ASP | ASP LYS GLU | LYS LYS LEU GLU | VAL ALA ARG |
| | 20 | 25 | | 30 |
| 100 | 110 | 120 | 130 | 140 |
| GCC ATC GAC | GCC GCA TCG | CGC GAC ACA | GGC TTC TTT TAC | GCG GTG AAC |
| ALA ILE ASP | ALA ALA SER | ARG ASP THR | GLY PHE PHE TYR | ALA VAL ASN |
| 35 | | 40 | 45 | |
| 150 | 160 | 170 | 180 | 190 |
| CAC GGT GTC | GAC CTG CCG | TGG CTC TCG | CGC GAG ACG AAC | AAA TTC CAC |
| HIS GLY VAL | ASP LEU PRO | TRP LEU SER | ARG GLU THR ASN | LYS PHE HIS |
| 50 | | 55 | 60 | |
| 200 | 210 | 220 230 | 240 | |
| ATG AGC ATC | ACG GAC GAG | GAG AAG TGG | CAG CTC GCC ATC | CGG GCC TAC |
| MET SER ILE | THR ASP GLU | GLU LYS TRP | GLN LEU ALA ILE | ARG ALA TYR |
| 65 | | 70 | 75 | 80 |
| | 250 | 260 | 270 | 280 |
| AAC AAG GAG | CAC GAG TCC | CAG ATC CGG | GCG GGC TAC TAC | CTG CCG ATC |
| ASN LYS GLU | HIS GLU SER | GLN ILE ARG | ALA GLY TYR TYR | LEU PRO ILE |
| | 85 | | 90 | 95 |
| 290 | 300 | 310 | 320 | 330 |
| CCG GGC AAG | AAG GCG GTC | GAA TCG TTC | TGC TAC CTG AAC | CCC TCC TTC |
| PRO GLY LYS | LYS ALA VAL | GLU SER PHE | CYS TYR LEU ASN | PRO SER PHE |
| | 100 | 105 | | 110 |
| 340 | 350 | 360 | 370 | 380 |
| AGC CCA GAC | CAC CCG CGA | ATC AAG GAG | CCC ACC CCT ATG | CAC GAG GTC |
| SER PRO ASP | HIS PRO ARG | ILE LYS GLU | PRO THR PRO MET | HIS GLU VAL |
| 115 | | 120 | 125 | |
| 390 | 400 | 410 | 420 | 430 |
| AAC GTC TGG | CCG GAC GAG | GCG AAG CAC | CCG GGG TTC CGG | GCC TTC GCC |
| ASN VAL TRP | PRO ASP GLU | ALA LYS HIS | PRO GLY PHE ARG | ALA PHE ALA |
| 130 | | 135 | 140 | |
| 440 | 450 | 460 470 | 480 | |
| GAG AAG TAC | TAC TGG GAC | GTC TTC GGC | CTC TCC TCC GCG | GTG CTG CGC |
| GLU LYS TYR | TYR TRP ASP | VAL PHE GLY | LEU SER SER ALA | VAL LEU ARG |
| 145 | 150 | | 155 | 160 |
| | 490 | 500 | 510 | 520 |
| GGC TAC GCT | CTC GCC CTA | GGT CGC GAC | GAG GAC TTC TTC | ACC CGC CAC |
| GLY TYR ALA | LEU ALA LEU | GLY ARG ASP | GLU ASP PHE PHE | THR ARG HIS |
| | 165 | | 170 | 175 |
| 530 | 540 | 550 | 560 | 570 |
| TCC CGC CGT | GAC ACG ACG | CTC TCG TCG | GTC GTG CTC ATC | CGT TAC CCG |
| SER ARG ARG | ASP THR THR | LEU SER SER | VAL VAL LEU ILE | ARG TYR PRO |
| | 180 | 185 | | 190 |
| 580 | 590 | 600 | 610 | 620 |
| TAC CTC GAC | CCG TAC CCG | GAG CCG GCC | ATC AAG ACG GCC | GAC GAC GGC |
| TYR LEU ASP | PRO TYR PRO | GLU PRO ALA | ILE LYS THR ALA | ASP ASP GLY |
| 195 | | 200 | 205 | |
| 630 | 640 | 650 | 660 | 670 |
| ACC AAG CTC | AGC TTC GAG | TGG CAC GAG | GAC GTG TCC CTC | ATC ACG GTG |
| THR LYS LEU | SER PHE GLU | TRP HIS GLU | ASP VAL SER LEU | ILE THR VAL |
| 210 | | 215 | 220 | |
| 680 | 690 | 700 | 710 | 720 |
| TTG TAC CAG | TCC GAC GTG | CAG AAT CTG | CAG GTC AAG ACC | CCG CAG GGC |
| LEU TYR GLN | SER ASP VAL | GLN ASN LEU | GLN VAL LYS THR | PRO GLN GLY |

-continued

DNA Sequence Encoding Isopenicillin N Synthetase
Activity and Corresponding Amino Acid Sequence

| 225 | 230 | | 235 | 240 |
|---|---|---|---|---|
| | 730 | 740 | 750 | 760 |
| TGG CAG GAC | ATC CAG GCT | GAC GAC ACG | GGC TTC CTC ATC | AAC TGC GGC |
| TRP GLN ASP | ILE GLN ALA | ASP ASP THR | GLY PHE LEU ILE | ASN CYS GLY |
| | 245 | | 250 | 255 |
| 770 | 780 | 790 | 800 | 810 |
| AGC TAC ATG | GCC CAT ATC | ACC GAC GAC | TAC TAC CCG GCC | CCG ATC CAC |
| SER TYR MET | ALA HIS ILE | THR ASP ASP | TYR TYR PRO ALA | PRO ILE HIS |
| | 260 | 265 | | 270 |
| 820 | 830 | 840 | 850 | 860 |
| CGC GTC AAA | TGG GTC AAC | GAG GAG CGC | CAG TCA CTG CCC | TTC TTC GTC |
| ARG VAL LYS | TRP VAL ASN | GLU GLU ARG | GLN SER LEU PRO | PHE PHE VAL |
| 275 | | 280 | 285 | |
| 870 | 880 | 890 | 900 | 910 |
| AAC CTG GGC | TGG GAG GAC | ACC ATC CAG | CCG TGG GAC CCC | GCG ACC GCC |
| ASN LEU GLY | TRP GLU ASP | THR ILE GLN | PRO TRP ASP PRO | ALA THR ALA |
| 290 | | 295 | 300 | |
| 920 | 930 | 940 | 950 | 960 |
| AAG GAT GGG | GCC AAG GAT | GCC GCC AAG | GAC AAG CCG GCC | ATC TCC TAC |
| LYS ASP GLY | ALA LYS ASP | ALA ALA LYS | ASP LYS PRO ALA | ILE SER TYR |
| 305 | 310 | | 315 | 320 |
| | 970 | 980 | 990 | 1000 |
| GGA GAG TAT | CTG CAG GGG | GGA CTG CGG | GGC TTG ATC AAC | AAG AAT GGT |
| GLY GLU TYR | LEU GLN GLY | GLY LEU ARG | GLY LEU ILE ASN | LYS ASN GLY |
| | 325 | | 330 | 335 |
| 1010 | | | | |
| CAG ACC TAA-3' | | | | |
| GLN THR | | | | | wherein, A is deoxyadenyl, G is deoxy9uanyl, C is deoxycytidyl, T is thymidyl, ALA is an alanine residue, ARG is an arginine residue, ASN is an asparagine residue, ASP is an aspartic acid residue, CYS is a cysteine residue, GLN is a glutamine residue, GLU is a glutamic acid residue, GLY is a glycine residue, HIS is a histidine residue, ILE is an isoleucine residue, LEU is a leucine residue, LYS is a lysine residue, MET is a methionine residue, PHE is a phenylalanine residue, PRO is a proline residue, SER is a serine residue, THR is a threonine residue, TRP is a tryptophan residue, TYR is a tyrosine residue, and VAL is a valine residue.

The DNA sequence shown above is ~63% in G and C content and encodes a polypeptide, isopenicillin N synthetase, with a calculated molecular weight of 38,476 daltons and an observed molecular weight of about 40,000 daltons.

Those skilled in the art will recognize that the DNA sequence depicted above is an important part of the present invention. The above sequence can be conventionally synthesized by the modified phosphotriester method using fully protected deoxyribonucleotide building blocks. Such synthetic methods are well known in the art and can be carried out in substantial accordance with the procedure of Itakura et al., 1977, Science 198:1056 and Crea et al., 1978, Proc. Nat. Acad. Sci. USA 75:5765. In addition, an especially preferred method is disclosed in Hsiung et al., 1983, Nucleic Acid Research 11:3227 and Narang et al., 1980, Methods in Enzymology 68:90. In addition to the manual procedures referenced above, the DNA sequence can be synthesized using automated DNA synthesizers, such as the Systec 1450A or ABS 380A DNA synthesizers.

Due to the degenerate nature of the genetic code, which results from there, being more than one codon for most of the amino acid residues and stop signal, the amino acid residue sequence of isopenicillin N synthetase depicted above can be encoded by a multitude of different DNA sequences. Because these alternate DNA sequences would encode the same amino acid residue sequence of the present invention, the present invention further comprises these alternate sequences.

In addition, there could be genetic variants of the isopenicillin N synthetase-encoding DNA of the present invention. These genetic variants would share substantial DNA and amino acid residue sequence homology with the compounds of the present invention and would have similar, if not identical, activity, but would differ somewhat from the actual compounds of the present invention. These genetic variants are also equivalent to the compounds of the present invention.

The isopenicillin N synthetase activity-encoding DNA compounds of the present invention were isolated from a strain of *Cephalosporium acremonium* commonly known as the Brotzu strain that is available from the American Type Culture Collection, Rockville, Md., under the accession number ATCC 11550. A genomic library of the total genomic DNA of the *C. acremonium* strain was constructed, and the genomic library was examined for the presence of sequences homologous to a set of 64 different deoxyribooligonucleotides. This set of 64 different deoxyribooligonucleotides was constructed in accordance with information obtained about the amino-terminal amino acid sequence of the *C. acremonium* isopenicillin N synthetase and with knowledge of the genetic code. A variety of the vectors of the genomic library were identified that were homologous to one or more of the 64 different deoxyribooligonucleotides. DNA sequencing revealed which vectors encoded the *C. acremonium* isopenicillin N synthetase.

After the vectors that encoded isopenicillin N synthetase were identified, one particular isopenicillin N synthetase-encoding vector was modified so as to delete most of the *Cephalosporium acremonium* DNA present on the vector that did not encode the isopenicillin N synthetase enzyme. The resulting vector, designated plasmid pIT335, has been transformed into *E. coli* K12 JA221 host cells, and the *E. coli* K12 JA221/pIT335 transformants have been deposited and made part of the stock culture collection of the Northern Regional Research Laboratories, Peoria, Ill., under the accession number NRRL B-15960. A restriction site and function map of plasmid pIT335 is presented in FIG. 1 of the accompanying drawings.

Plasmid pIT335 can be isolated from *E. coli* K12 JA221 by the procedure described in Example 1. Plasmid pIT335 was used as starting material in the construction of a plasmid, designated pIT337, that drives high-level expression of isopenicillin N synthetase in *E. coli*. Plasmid pIT337 was constructed by ligating the ~1.5 kb NcoI-BamHI restriction fragment of plasmid pIT335 to the ~8.7 kb NcoI-NcoI and ~1.6 kb NcoI-BamHI restriction fragments of plasmid pCZ106.

Figure 2:
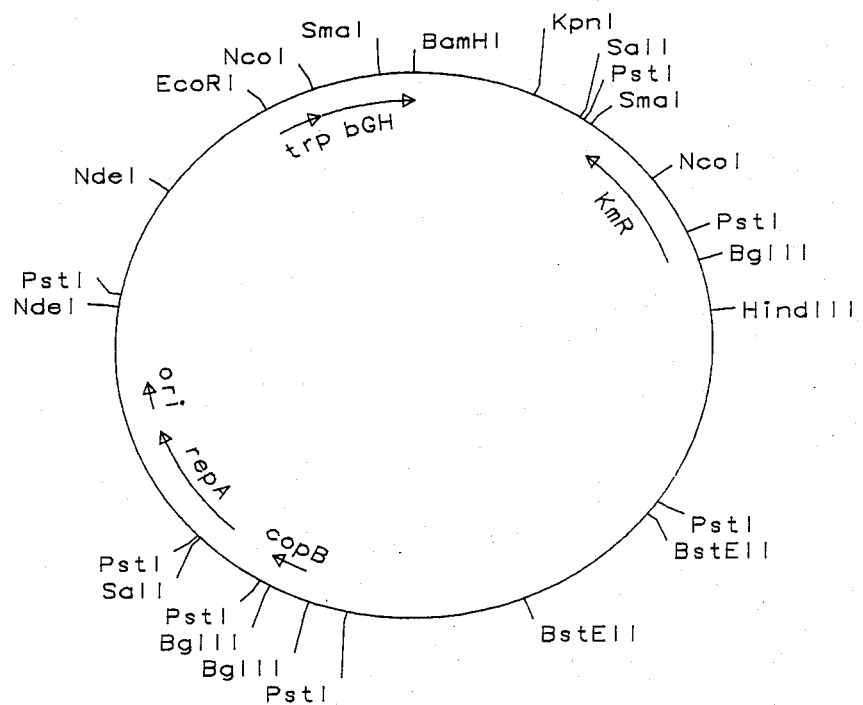
FIG. 2. A restriction site and function map of plasmid pCZ106.

Plasmid pCZ106 comprises a runaway replicon, the trp transcriptional and translational activating sequence and operator, and a DNA sequence encoding a bovine growth hormone derivative. The use of the type of runaway replicon present on plasmid pCZ106 is described and disclosed in U.S. Pat. Nos. 4,487,835; 4,499,189, and 4,495,287. Essentially, at low temperatures of about 25° C., a plasmid comprising a runaway replicon has a copy number of about ~10-15 copies per *E. coli* host cell, but when the temperature is raised to about 37° C., the copy number increases to about 1,000 copies per *E. coli* host cell. *E. coli* K12 RV308/pCZ106 host cells, from which plasmid pCZ106 can be isolated, have been deposited and made part of the stock culture collection of the Northern Regional Research Laboratories, Peoria, Ill., under the accession number NRRL B-15959. A restriction site and function map of plasmid pCZ106 is presented in FIG. 2 of the accompanying drawings.

Plasmid pIT337 comprises the runaway replicon and trp transcriptional and translational activating sequence of plasmid pCZ106 and the protein-coding sequence of the isopenicillin N synthetase gene from plasmid pIT335. The ~1.5 kb NcoI-BamHI restriction fragment of plasmid pIT335 comprises the entire protein-coding sequence for isopenicillin N synthetase, and the NcoI restriction enzyme recognition sequence which is

comprises the

Figure 3:
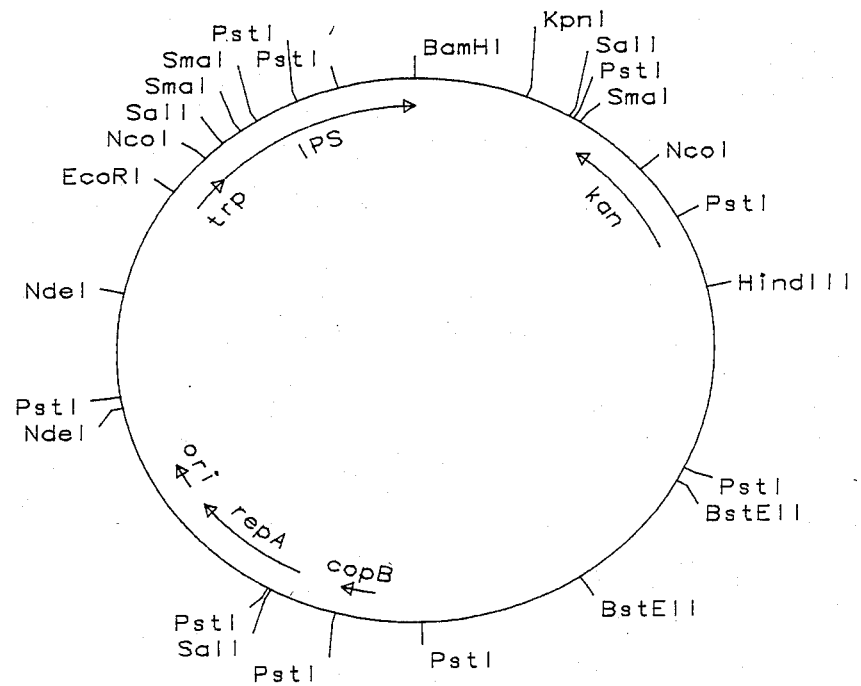
FIG. 3. A restriction site and function map of plasmid pIT337.

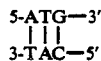

which encodes the amino-terminal methionyl residue of isopenicillin N synthetase. Plasmid pIT337 was constructed so that the trp transcriptional and translational activating sequence would be positioned to drive expression of the isopenicillin N synthetase-encoding DNA. A restriction site and function map of plasmid pIT337 is presented in FIG. 3 of the accompanying drawings. Example 2 describes the construction of plasmid pIT337 in more detail.

At temperatures of about 37° C., *E. coli* K12 RV308 (NRRL B-15624) cells harboring plasmid pIT337 express isopenicillin N synthetase at high levels, approaching ~9% of the total cell protein. Crude cell extracts from these *E. coli* K12 RV308/pIT337 transformants are able to catalyze the conversion of δ-(L-α-aminoadipyl)-L-cysteinyl-D-valine into isopenicillin N, whereas cell extracts from non-transformed *E. coli* K12 RV308 cells cannot catalyze this conversion. The method of assay and results of the assay for the conversion reaction are presented in Example 3.

Plasmid pIT337 provides an efficient means of producing large amounts of isopenicillin N synthetase in *E. coli*. Because *E. coli* transformants of plasmid pIT337 express isopenicillin N synthetase at levels approaching 9% of total cell protein and because culturing *E. coli* is less complex than culturing organisms that naturally produce isopenicillin N synthetase, *E. coli*/pIT337 transformants can be used to produce recombinant isopenicillin N synthetase more efficiently and economically than non-recombinant or "natural" isopenicillin N synthetase producers.

Isopenicillin N synthetase can be used to produce isopenicillin N from δ-(L-α-aminoadipyl)-L-cysteinyl-D-valine in a cell-free system as described in Example 3. Isopenicillin N is not only a useful antibiotic, but also is the starting material for the production of such important antibiotics as penicillin N, cephalexin, and other cephalosporins (see U.S. Pat. No. 4,307,192). Perhaps the most important use of isopenicillin N synthetase is the use of the enzyme to condense tripeptides other than δ-(L-α-aminoadipyl)-L-cysteinyl-D-valine into novel β-lactam derivatives.

Cell-free extracts of penicillin-producing organisms can be used to synthesize unnatural (not produced in nature) β-lactams. The *E. coli* expression vectors of the present invention provide an inexpensive and efficient method of obtaining isopenicillin N synthetase, which can be used in vitro to condense tripeptides which do not naturally occur in nature to form novel antibiotics or antibiotic core structures.

Plasmid pIT337 is especially preferred for driving expression of IPS in *E. coli* not only because of the high expression levels achieved when using the plasmid but also because of the selectable marker present on the plasmid. Many recombinant DNA vectors encode a β-lactamase, so that cells transformed with such vectors can grow in the presence of certain β-lactam antibiotics, such as ampicillin. However, if one desires to use a cell-free extract containing IPS for purposes of constructing β-lactams, one would not want the extract to contain β-lactamase activity. Thus, plasmid pIT337 does not encode a β-lactamase for a selectable marker but rather encodes kanamycin phosphotransferase, an enzyme non-reactive with β-lactams.

The IPS expression vectors of the present invention are not limited to a particular selectable marker. Those skilled in the art recognize that many selectable markers are suitable for use on IPS expression vectors. Such selectable markers include genes that confer tetracycline resistance, i.e., a selectable marker on plasmid pBR322, and genes that confer chloramphenicol resistance, i.e., a selectable marker on plasmids pACYC184 and pBR325.

Figure 20:
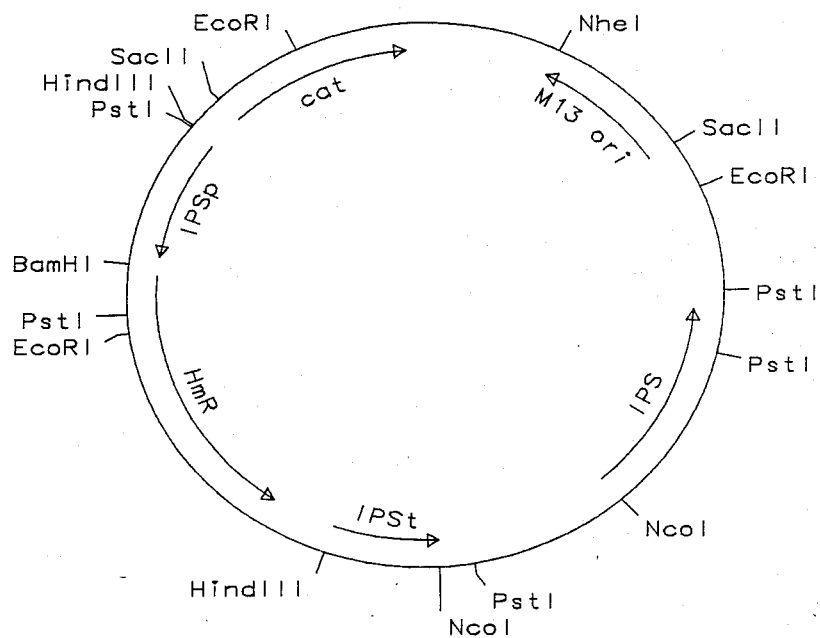
FIG. 20. A restriction site and function map of plasmid pPS47.

The vectors of the present invention include vectors that drive expression of IPS in β-lactam producing organisms. The β-lactamase gene cannot be used as a selectable marker in a β-lactam-producing microorganism. This gene is nevertheless present on many of the vectors of the present invention designed for use in β-lactam-producing organisms simply because of its utility as a selectable marker in *E. coli*. Many of the present vectors designed for β-lactam-producing organisms also replicate in *E. coli* for ease of plasmid preparation. Certain β-lactam-producing organisms, such as *Cephalosporium acremonium*, are eukaryotic cells, but nevertheless, the prokaryotic β-lactamase gene derived from plasmid pBR322 seems to function in some eukaryotic host cells. See Marczynski and Jaehning, 1985, Nuc. Acids Res. 13(23):8487–8506 and Breunig et al., 1982, Gene 20:1–10. To avoid the possibility of introducing a β-lactamase gene that could possibly express in an organism transformed to obtain greater β-lactam-producing ability, the present invention also provides vectors that utilize a selectable marker other than the β-lactamase gene, such as a chloramphenicol acetyltransferase-encoding gene. Plasmid pPS47 of the present invention, described in Example 12 and depicted in FIG. 20, below, is one such vector. Plasmid pPS47 comprises a chloramphenicol resistance-conferring gene for purposes of selection in E. coli, a hygromycin resistance-conferring gene for purposes of selection in Cephalosporium acremonium, and the IPS gene for purposes of improving the cephalosporin-producing ability of C. acremonium. Other resistance-conferring genes that can be exchanged for the chloramphenicol resistance-conferring gene on plasmid pPS47 to obtain equivalent plasmids include the apramycin resistance conferring gene and any one of a number of kanamycin resistance-conferring genes known in the art.

As stated above, a β-lactamase gene cannot be used as a selectable marker in Cephalosporium acremonium, nor does C. acremonium encode an endogenous β-lactamase. However, many E. coli strains, even those sensitive to β-lactams, do encode nd express, at low levels, an endogenous β-lactamase, a product of the ampC gene. See Juarin et al., 1981, Proc. Natl. Acad. Sci. 78(8):4897–4901 and Grundström et al., 1982, Proc. Natl. Acad. Sci. 79:1111–1115. The presence of the ampC gene product in crude cell extracts of recombinant E. coli cells containing an IPS expression vector could lead to degradation of β-lactams prepared using that extract. To avoid such degradation, E. coli K12 RV308 was subjected to mutagenesis to obtain a strain, designated E. coli K12 A85892, that does not express a β-lactamase activity (unless the activity is encoded on a recombinant vector present in the cell). E. coli K12 A85892 is the most preferred strain for use with vectors of the present invention that drive expression of IPS in E. coli. E. coli K12 A85892 can be obtained from the Northern Regional Research Center under the accession number NRRL B-18096.

The search for unnatural tripeptides that will serve as substrates for isopenicillin N synthetase can be complemented by a search for mutant isopenicillin N synthetases that will accept unnatural tripeptides as substrate. The present invention provides the starting material for such a search for a mutant isopenicillin N synthetase. E. coli is the best host for mutational cloning experiments, and the E. coli expression vectors of the present invention can be readily mutated by procedures well known in the art, such as, for example, treatment with radiation (X-ray or UV) or chemical mutagens (such as ethylmethanesulfonate, nitrosoguanidine, or methylmethanesulfonate) or site-specific mutagenesis, to obtain mutant enzymes that recognize unnatural tripeptides as substrate and catalyze the condensation of those unnatural tripeptides to unnatural β-lactams.

Example 13 of the instant specification describes three distinct mutant IPS genes that encode mutant IPS enzymes with IPS activity. As described in Example 13, the IPS coding sequence was subjected to site-specific mutagenesis to change, in one clone, the cysteine codon for the amino-acid residue at position 106 to a serine codon. In another clone, the cysteine codon for the amino-acid residue at position 255 was changed to a serine codon. Finally, the two clones were recombined by recombinant techniques to generate a codinq sequence in which the cysteine codons for residues 106 and 255 were changed to serine codons. The coding sequences were then placed in an expression vector and expressed in E. coli to yield mutant enzymes with IPS activity.

As those skilled in the art will recognize, the present invention allows one to change the codons for the IPS enzyme at will. Given the DNA sequence for the IPS gene, only routine procedures are required to generate mutant IPS enzymes that vary from the natural IPS enzyme at any number of amino-acid residue positions. Such mutant enzymes would be encoded by mutant IPS coding sequences, including sequences in which aminoacid codons have been deleted from or inserted into the natural IPS coding sequence. Such mutant IPS enzymes are within the scope of the present invention, because even if one cannot absolutely predict whether a given mutation will destroy activity of the encoded IPS, one need merely express the mutant sequence, as exemplified herein, to ascertain the effect on IPS activity.

The present invention is not limited to the particular vectors exemplified herein. Instead, the present invention comprises DNA compounds that encode isopenicillin N synthetase activity. The DNA compounds of the present invention can be used to construct expression vectors that drive expression of isopenicillin N synthetase in any host cell in which the expression vector replicates or integrates and in which the transcriptional and translational activating sequence used to express the isopenicillin N synthetase activity functions.

Therefore, although the E. coli expression vectors exemplified herein utilize a runaway replicon functional in E. coli, the present invention comprises any E. coli expression plasmid or vector that drives expression of isopenicillin N synthetase in E. coli. Thus, the present invention comprises expression vectors which drive expression of isopenicillin N synthetase and utilize a replicon functional in E. coli, such as, for example, a replicon from such plasmids as pBR322, pACYC184, F, ColV-K94, R1, R6-5, or R100. Nor is the present invention solely limited to plasmid vectors, for the present invention also comprises expression vectors that express isopenicillin N synthetase activity and utilize integration or viral replication to provide for replication and maintenance in the host cell.

The present invention is not limited to a particular transcriptional and translational activating sequence to drive expression of the isopenicillin N synthetase activity encoding DNA. The present invention comprises the use of any transcriptional and translational activating sequence that functions in E. coli and is used to express isopenicillin N synthetase in E. coli. Many transcriptional and translational activating sequences functional in E. coli are known and are suitable for driving expression of isopenicillin N synthetase activity in E. coli. Such transcriptional and translational activating sequences include, but are not limited to, the lpp, lac, trp, tac, $\lambda p_L$, and $\lambda p_R$ transcriptional and translational activating sequences.

In addition to the various E. coli transcriptional and translational activating sequences exemplified above, transcriptional and translational activating sequences from other organisms can be ligated to the present isopenicillin N synthetase-encoding DNA compounds to form expression vectors that drive expression of isopenicillin N synthetase activity in host cells in which the activating sequence functions. Although *E. coli* is the host best suited for isopenicillin N synthetase production and subsequent purification for in vitro use, vectors that drive expression of isopenicillin N synthetase activity in host cells other than *E. coli* are also useful, especially for purposes of increasing the β-lactam antibiotic-producing ability and efficiency of a given organism.

A variety of organisms produce β-lactam antibiotics. The following Table presents a non-comprehensive list of β-lactam antibiotic-producing organisms.

TABLE I

β-Lactam Antibiotic-Producing Organisms

| Organism | Antibiotic |
|---|---|
| Agrobacterium | various β-lactams |
| Cephalosporium | |
| acremonium | penicillins and cephalosporins |
| Chromobacterium | various β-lactams |
| Gluconobacter | various β-lactams |
| Nocardia | |
| lactamadurans | cephamycin C |
| uniformis | nocardicin |
| Penicillium | |
| chrysogenum | various penicillins and other β-lactams |
| Serratia | various β-lactams |
| Streptomyces | |
| antibioticus | clavulanic acid |
| argenteolus | asparenomycin A, MM 4550, and MM 13902 |
| cattleya | thienamycin |
| chartreusis | SF 1623 and cephamycin A and B |
| cinnamonensis | cephamycin A and B |
| clavuligerus | PA-32413-I, cephamycin C, A16886A, penicillins, cephalosporins, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B and carpetimycin A and B |
| halstedi | cephamycin A and B |
| heteromorphus | C2081X and cephamycin A and B |
| hygroscopicus | deacetoxy-cephalosporin C |
| lipmanii | cephamycin, penicillin N, 7-methoxycephalosporin C, A16884, MM4550, MM13902 |
| olivaceus | epithienamycin F, MM 4550, and MM 13902 |
| panayensis | C2081X and cephamycin A and B |
| pluracidomyceticus | pluracidomycin A |
| rochei | cephamycin A and B |
| sioyaensis | MM 4550 and MM 13902 |
| sp. OA-6129 | OA-6129A |
| sp. KC-6643 | carpetimycin A |
| tokunomensis | asparenomycin A |
| viridochromogenes | cephamycin A and B |
| wadayamensis | WS-3442-D |

Many of the foregoing β-lactam antibiotic-producing organisms are used in the pharmaceutical industry for purposes of antibiotic production. The antibiotic-producing ability of these organisms can be increased and made more efficient by increasing the intracellular concentration of the antibiotic biosynthetic enzymes during the fermentation. The isopenicillin N synthetase activity-encoding DNA compounds of the present invention can be used to construct expression vectors that, when transformed into the appropriate host cell, increase the intracellular concentration of isopenicillin N synthetase activity of the transformed host cell and thereby increase the antibiotic-producing ability and efficiency of that cell, provided that the host cell produces a β-lactam antibiotic via an intermediate reaction involving isopenicillin N synthetase activity.

A vector that will increase the intracellular concentration of isopenicillin N synthetase activity of a given host cell into which the vector is transformed requires the following elements: (1) an isopenicillin N synthetase activity-encoding DNA compound of the present invention; (2) a transcriptional and translational activating sequence that not only functions in the host cell to be transformed, but also is positioned in the correct orientation and position to drive expression of the isopenicillin N synthetase activity-encoding DNA; and (3) maintenance of the vector in the host cell. Of course, the above-described vector could also comprise an antibiotic resistance-conferring gene or some other element that provides a means of selecting for host cells which contain the vector, but such selectable elements may neither be necessary nor desired when the vector integrates into the chromosomal DNA of the host cell.

Figure 5:
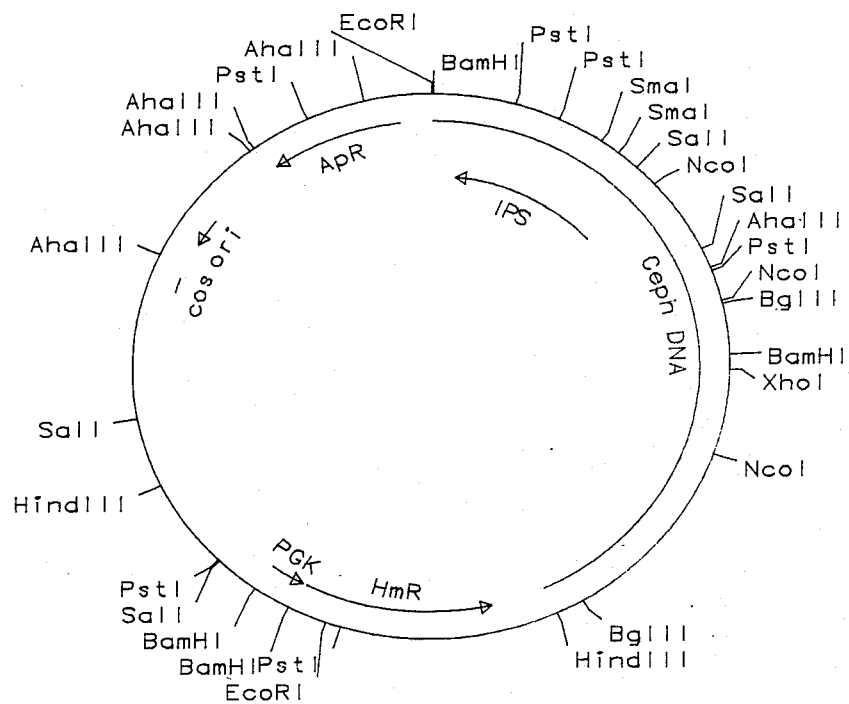
FIG. 5. A restriction site and function map of plasmid pPS20.

Plasmid pPS20 is an expression vector of the present invention that exemplifies the type of vector designed to increase the intracellular concentration of isopenicillin N synthetase activity in a β-lactam antibiotic-producing host cell. Plasmid pPS20 was constructed by inserting the ~2.7 kb HindIII restriction fragment of plasmid pIT221 into the single HindIII restriction enzyme recognition site of plasmid pIT335. The ~2.7 kb HindIII restriction fragment of plasmid pIT221 comprises the transcriptional and translational activating sequence of the yeast *Saccharomyces cerevisiae* phosphoglycerate kinase (PGK) gene ligated in the correct position and orientation to drive expression of a hygromycin resistance-conferring gene. Because the ~2.7 kb HindIII restriction fragment of plasmid pIT221 could be inserted into HindIII-digested plasmid pIT335 in either of two orientations, the ligation which produced plasmid pPS20 also produced a functionally equivalent isomer, designated plasmid pPS20.1. A restriction site and function map of plasmid pPS20 is presented in FIG. 5 of the accompanying drawings; the construction of plasmids pPS20 and pPS20.1 is described in Example 4.

Figure 4:
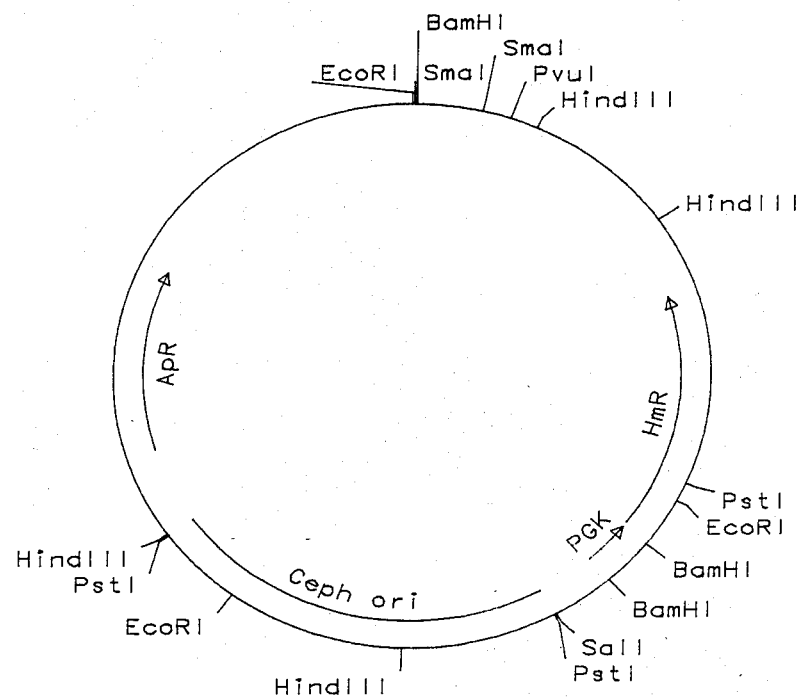
FIG. 4. A restriction site and function map of plasmid pIT221.

The plasmid pIT221 starting material used in the construction of plasmids pPS20 and pPS20.1 was disclosed and claimed in U.S. patent application Ser. No. 654,919, filed Sept. 27, 1984. Construction Flow Sheets I–VI and Examples 1–6 on pages 29–57 of U.S. patent application Ser. No. 654,919 describe the construction of plasmid pIT221 and are incorporated herein by reference. A restriction site and function map of plasmid pIT221 is presented in FIG. 4 of the accompanying drawings.

The ~2.7 kb HindIII restriction fragment of plasmid pIT221 comprises a hygromycin resistance-conferring gene ligated to the yeast PGK transcriptional and translational activating sequence in the correct position and orientation for expression of the hygromycin resistance-conferring activity (HmR). As disclosed in U.S. patent application Ser. No. 654,919 the PGK-HmR gene can be used to transform *Cephalosporium acremonium* and related host cells to the hygromycin-resistant phenotype.

Plasmid pPS20 comprises the PGK-HmR gene, and *Cephalosporium acremonium* /pPS20 transformants can be selected on the basis of the hygromycin resistance conferring activity expressed by the transformants. Plasmid pPS20 also comprises the isopenicillin N synthetase-encoding DNA of the present invention together with the genomic DNA which flanks the isopenicillin N synthetase-encoding DNA in the *Cephalosporium acremonium* genome.

Because plasmid pPS20 comprises almost 3 kb of the genomic DNA that was located upstream of the isopenicillin N synthetase-encoding DNA in the *Cephalosporium acremonium* genome, plasmid pPS20 necessarily comprises the transcriptional and translational activating sequence of the isopenicillin N synthetase encoding DNA. Most transcriptional and translational activating sequences are encoded upstream of the DNA to be activated, although some ribosomal RNA-encoding DNA sequences are activated by transcriptional activating sequences that are not located upstream of the coding region. "Upstream" is a word used in the art of molecular biology and, in the present context, refers to DNA in the 5' direction from the 5' end of the coding strand of the isopenicillin N synthetase-encoding DNA.

The *Cephalosporium acremonium* transcriptional and translational activating sequence encoded on plasmid pPS20 is correctly positioned to drive expression of the isopenicillin N synthetase activity-encoding DNA, because in the construction of plasmid pPS20 no deletions or insertions affecting the transcriptional and translational activating sequence were introduced in the DNA flanking the 5' end of the coding strand of the isopenicillin N synthetase activity-encoding DNA. Plasmid pPS20 can therefore be used to increase the antibiotic-producing ability and efficiency of *Cephalosporium acremonium* and related host cells in which the *C. acremonium* transcriptional and translational activating sequence functions. This increased antibiotic-producing ability and efficiency is due to increased levels of isopenicillin N synthetase activity in the transformant, due to the presence of additional, expressed copies of the isopenicillin N synthetase activity-encoding DNA. Plasmid pPS20 also comprises a hygromycin resistance conferring gene that functions in *C. acremonium* and allows for selection of *C. acremonium*/pPS20 transformants.

Once the *Cephalosporium acremonium*/pPS20 transformants are selected, however, there is no need to maintain the pressure of selection, hygromycin B, in the growth medium of the transformants. There is no need for selective pressure, because the *C. acremonium*/pPS20 transformants are very stable. This stability is believed to result from the plasmid pPS20 transforming *C. acremonium* via chromosomal integration. The present invention, however, is not limited to plasmids that drive expression of isopenicillin N synthetase activity in *C. acremonium* and transform via chromosomal integration. Extra chromosomally replicating expression vectors for *C. acremonium* are readily constructed in accordance with the teaching of U.S. Pat. No. 4,492,758. U.S. Pat. No. 4,492,758 describes mitochondrial DNA segments that can be inserted into a vector such as plasmid pPS20 to provide the necessary functions for extra chromosomal replication of the vector in *C. acremonium*.

As described above, plasmid pPS20 and one of the plasmids from which plasmid pPS20 was derived, pIT335, comprise a *Cephalosporium acremonium* transcriptional and translational activating sequence. Because the *C. acremonium* transcriptional and translational activating sequence located on plasmids pIT335 and pPS20 can be used to drive expression of a wide variety of DNA sequences, the activating sequence comprises an important part of the present invention. Although the sequence data on the *C. acremonium* transcriptional and translational is believed to be encoded on the ~500 bp SalI-NcoI restriction fragment located immediately upstream of and adjacent to the isopenicillin N synthetase activity-encoding DNA on plasmids pIT335 and pPS20. Any restriction fragment that comprises the aforementioned ~500 bp SalI-NcoI restriction fragment necessarily comprises the *C. acremonium* transcriptional and translational activating sequence.

There is a sequence data on the *Cephalosporium acremonium* transcriptional and translational activating sequence encoded on plasmid pIT335. The sequence below is the DNA sequence that is upstream of the isopenicillin N synthetase activity-encoding DNA present on plasmid pIT335. Only a portion of the sequence of the ~500 bp SalI-NcoI restriction fragment that comprises the activating sequence is known, as is illustrated by the "XXXXXXXXXX" region depicted in the sequence. In order to further clarify how the activating sequence is oriented in plasmid pIT335, the restriction fragment is illustrated with single-stranded DNA overlaps characteristic of restriction enzyme SalI and NcoI cleavage.

Partial DNA Sequence
of the *Cephalosporium acremonium*
Transcriptional and Translational Activating Sequence
Encoded on Plasmid pIT335

```
            ←— ~380 bp —→
5'-TCGAC  XXXXXXXXXX   CGAATACTTG   AATATTCCTT   GGTCGCTCTT
      |   ||||||||||   ||||||||||   ||||||||||   ||||||||||
    3'-G  XXXXXXXXXX   GCTTATGAAC   TTATAAGGAA   CCAGCGAGAA

CTGATTTTCG   AGGCTTCTCC   TTCCGCCATC   GTCGCCTCAC
          ||||||||||   ||||||||||   ||||||||||   ||||||||||
          GACTAAAAGC   TCCGAAGAGG   AAGGCGGTAG   CAGCGGAGTG

GCATATCTCG   TCTTTCACAT   CTTACACCAG   CAGGACAAAC
          ||||||||||   ||||||||||   ||||||||||   ||||||||||
          CGTATAGAGC   AGAAAGTGTA   GAATGTGGTC   GTCCTGTTTG

CGTCAC—3'
          ||||||
          GCAGTGGTAC—5'
```

↑ —→ beginning of isopenicillin N synthetase coding region. "TAC" is complementary to the 5'-ATG—3' that encodes the amino-terminal methionyl residue of isopenicillin N synthetase.

The *Cephalosporium acremonium* transcriptional and translational activating sequence can be used to drive expression of any DNA sequence, as plasmid pPS21 illustrates. Plasmid pPS21 is a derivative of plasmid pIT221 that results from the replacement of the PGK transcriptional and translational activating sequence used to drive expression of the hygromycin resistance-conferring gene with the *C. acremonium* transcriptional and translational activating sequence of the present invention. The replacement is accomplished by first removing the ~300 bp XmaI fragment of plasmid pIT221 to form plasmid pPS19. This XmaI deletion was performed to remove a BamHI restriction enzyme recognition site that would interfere with the construction of pPS21. Plasmid pPS19 is then digested with BamHI and treated with the Klenow fragment of *E. coli* DNA Polymerase I. The BamHI digestion excises an ~230 bp BamHI restriction fragment comprising the PGK transcriptional and translational activating sequence; the Klenow treatment makes double-stranded DNA out of the single-stranded BamHI overlaps. The large, ~7.7 kb BamHI fragment of plasmid pPS19 is then ligated to the ~0.8 kb, Klenow-treated, NcoI restriction fragment of plasmid pIT335 that comprises the *C. acremonium* transcriptional and translational activating sequence.

Figure 6:
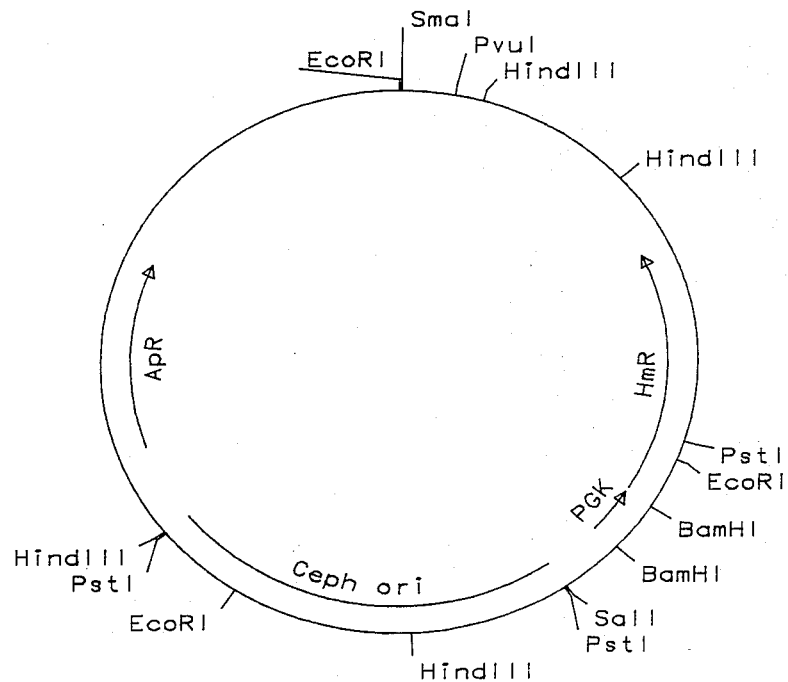
FIG. 6. A restriction site and function map of plasmid pPS19.
Figure 7:
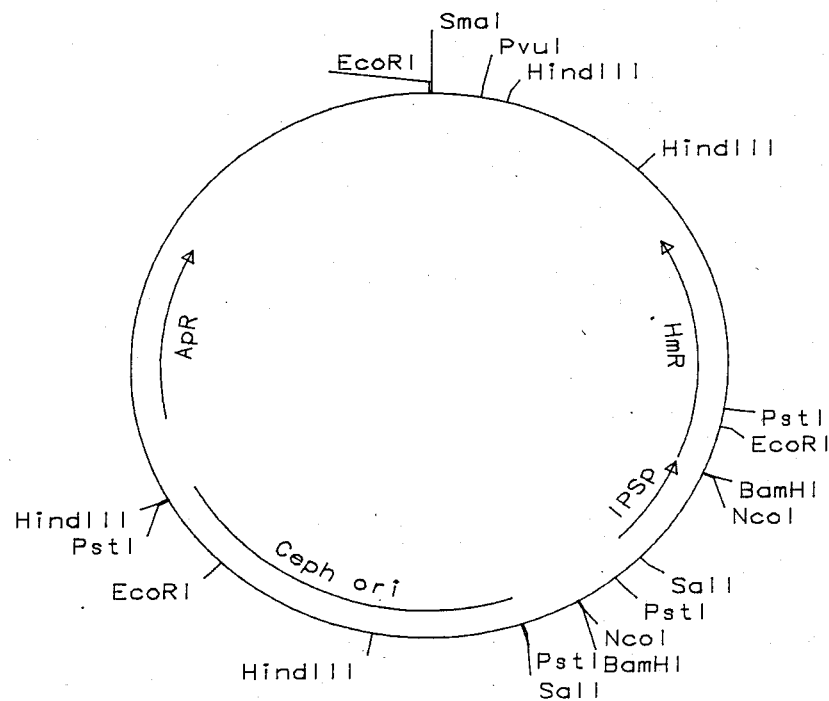
FIG. 7. A restriction site and function map of plasmid pPS21.

Of course, the Klenow-treated NcoI restriction fragment can insert in one of two orientations, with only one of the possible orientations achieving the desired result—the correct positioning of the *Cephalosporium acremonium* transcriptional and translational activating sequence to drive expression of the hygromycin resistance-conferring gene. A restriction site and function map of plasmid pPS21 is presented in FIG. 7 of the accompanying drawings, and a restriction site and function map of plasmid pPS19 is presented in FIG. 6 of the accompanying drawings. A more detailed description of the construction of plasmid pPS21 is presented in Example 5.

Plasmid pPS21A is another vector of the present invention that utilizes the transcriptional and translational activating sequence of the IPS gene to drive expression of a hygromycin resistance-conferring gene in *Cephalosporium acremonium*. A useful intermediate plasmid, designated plasmid pPS23, was used in the construction of plasmid pPS21A. Plasmid pPS23 was constructed by isolating the ~850 bp NcoI restriction fragment of plasmid pIT335 that comprises the activating sequence of the IPS gene, attaching linkers with BamHI and NcoI-compatible, single-stranded overlaps to the ~850 bp NcoI fragment, and ligating the resulting plasmid pIT335-derived, ~860 bp BamHI restriction fragment to BamHI-digested plasmid pUC8. This ligation produced two plasmids, designated pPS23 and pPS23.1, that differ only with respect to the orientation of the inserted BamHI Pharmacia P-L Biochemicals, 800 Centennial Ave., Piscataway, N.J. 08854.

Plasmid pPS23 was digested with restriction enzyme BamHI, and the ~860 bp BamHI restriction fragment that comprises the IPS transcriptional and translational activating sequence was isolated and ligated with BamHI-digested plasmid pPS19. This ligation produced a number of useful plasmids, including plasmid pPS21A. Plasmid pPS21A results from the ligation of the ~0.86 kb BamHI restriction fragment of plasmid pPS23 with the ~7.7 kb BamHI restriction fragment of plasmid pPS19 and comprises the transcriptional and translational activating sequence of the IPS gene located in the proper orientation to drive expression of the hygromycin resistance-conferring gene. The linkers used in the construction of plasmid pPS23 ensured that the proper reading frame would be maintained in plasmid pPS21A for expression of the hygromycin resistance conferring gene. The construction of plasmid pPS21A is described in Example 7; a restriction site and function map of plasmid pPS21A is presented in FIG. 8 of the accompanying drawings.

Several other useful plasmids were also produced in the same ligation that produced plasmid pPS21A. Plasmid pPS22 comprises the same sequences as plasmid pPS21A, but the BamHI restriction fragment that comprises the activating sequence of the IPS gene is oriented in the opposite direction of the orientation in plasmid pPS21A. Consequently, plasmid pPS22 does not confer hygromycin resistance to *Cephalosporium acremonium* at high frequency, so plasmid pPS22 serves as a useful negative control in *C. acremonium* transformations.

Another plasmid produced in this ligation has utility both as a negative control in *Cephalosporium acremonium* transformations and also as a plasmid that can be used to identify *C. acremonium* sequences that possess transcriptional and translational activating activity. As described above, plasmid pPS19 comprises the *Saccharomyces cerevisiae* PGK transcriptional and translational activating sequence in the proper orientation to drive expression of the hygromycin resistance conferring gene. Digestion of plasmid pPS19 with restriction enzyme BamHI yields two fragments: one fragment is about 230 bp in size and comprises the PGK activating sequence, and the other fragment is ~7.7 kb in size and comprises most of the coding sequence for the hygromycin resistance conferring gene.

Circularization of the ~7.7 kb BamHI restriction fragment of plasmid pPS19 yields plasmid pPS24, which lacks a transcriptional and translational activating sequence positioned to drive expression of the hygromycin resistance-conferring gene present on the vector. Plasmid pPS24 can therefore transform *Cephalosporium acremonium* to hygromycin resistance by integrating into the *C. acremonium* DNA in such a position that an endogenous *C. acremonium* transcriptional and translational activating sequence drives expression of the gene. Consequently, identification of the site of integration of the plasmid pPS24 DNA in a hygromycin-resistant, *C. acremonium*/pPS24 transformant will also identify a *C. acremonium* transcriptional and translational activating sequence. Alternatively, *C. acremonium* DNA can be cloned into the single BamHI site on plasmid pPS24 and the resulting plasmids used to transform *C. acremonium*. Those plasmids that transformed *C. acremonium* to hygromycin resistance at a high frequency will necessarily comprise a transcriptional and translational activating sequence functional in *C. acremonium*.

Yet other useful plasmids were produced in the same ligation that produced plasmid pPS21A. These plasmids, designated plasmids pPS25 and pPS25.1, were produced by the ligation of the two BamHI restriction fragments of plasmid pPS19 to the ~860 bp BamHI restriction fragment of plasmid pPS23. In plasmid pPS25, both the PGK and IPS activating sequences are in the proper orientation to drive expression of the hygromycin resistance-conferring gene. Plasmid pPS25 comprises the IPS activating sequence located immediately upstream of the coding sequence of the hygromycin resistance-conferring gene and the PGK activating sequence located immediately upstream of the IPS activating sequence. Plasmid pPS25 confers hygromycin resistance to *Cephalosporium acremonium*. A restriction site and function map of plasmid pPS25 is presented in FIG. 9 of the accompanying drawings. The construction of plasmids pPS22, pPS24, and pPS25 is also described in Example 7.

Plasmid pPS25.1 only differs from plasmid pPS25 with respect to the orientation of the ~0.23 kb BamHI restriction fragment that comprises the PGK activating sequence. In plasmid pPS25.1, the PGK activating sequence is not positioned in the orientation that allows the PGK activating sequence to drive expression of the hygromycin resistance-conferring gene. However, both plasmid pPS25 and pPS25.1 transform *Cephalosporium acremonium* to the hygromycin-resistant phenotype at the same high frequency, indicating that the PGK activating sequence is not necessary for the expression of the hygromycin-resistant phenotype.

Figure 10:
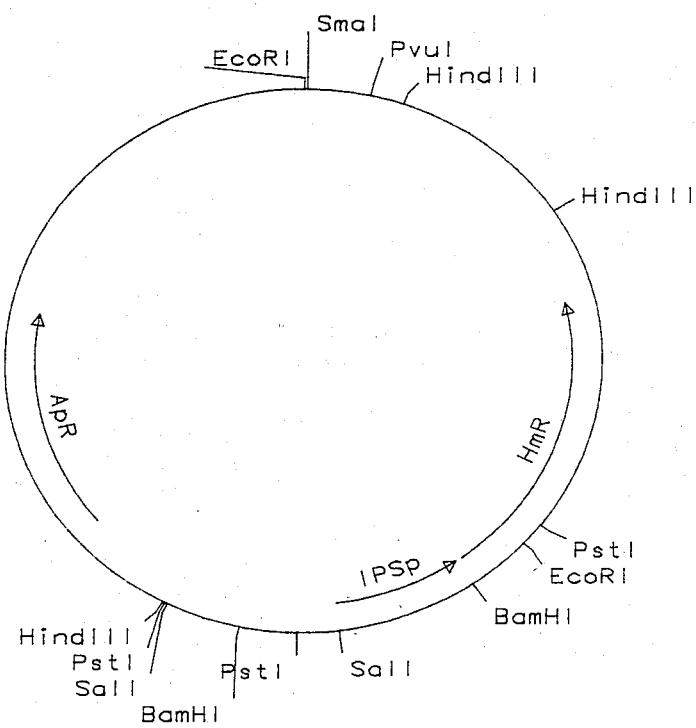
FIG. 10. A restriction site and function map of plasmid pPS28.
Figure 11:
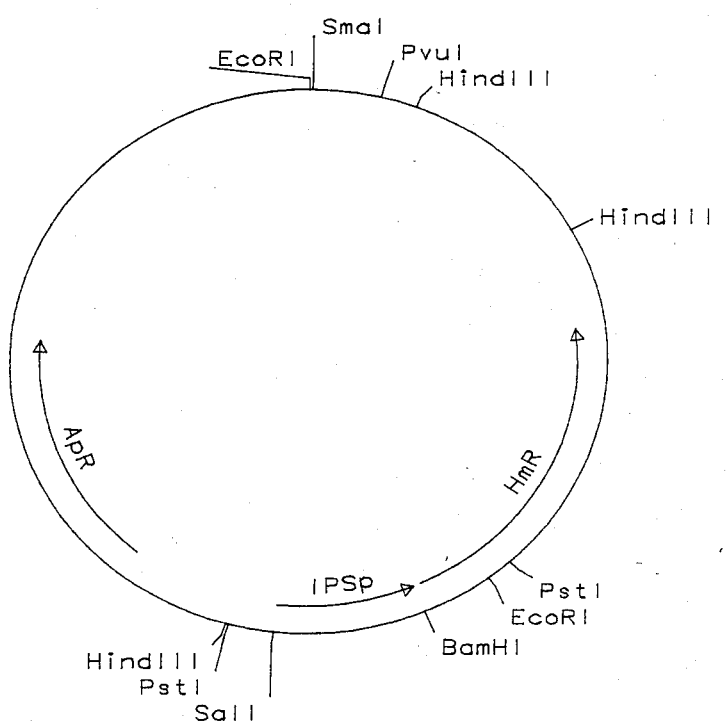
FIG. 11. A restriction site and function map of plasmid pPS29.

Other useful plasmids of the present invention that confer hygromycin resistance to *Cephalosporium acremonium* can be constructed by partial digestion of plasmid pPS21 with restriction enzyme PstI, followed by religation. Plasmid pPS28 results from deleting from plasmid pPS21A the ~1.85 kb PstI restriction fragment that comprises the Cephalosporium origin of replication. Plasmid pPS29 results from deleting from plasmid pPS21A the same PstI fragment that was deleted to get plasmid pPS28 together with the ~0.49 kb PstI restriction fragment that lies between the Cephalosporium origin of replication and the activating sequence of the IPS gene on plasmid pPS21A. Restriction site and function maps of plasmids pPS28 and pPS29 are respectively presented in FIGS. 10 and 11. The construction of plasmids pPS28 and pPS29 is described in Example 8.

Figure 12:
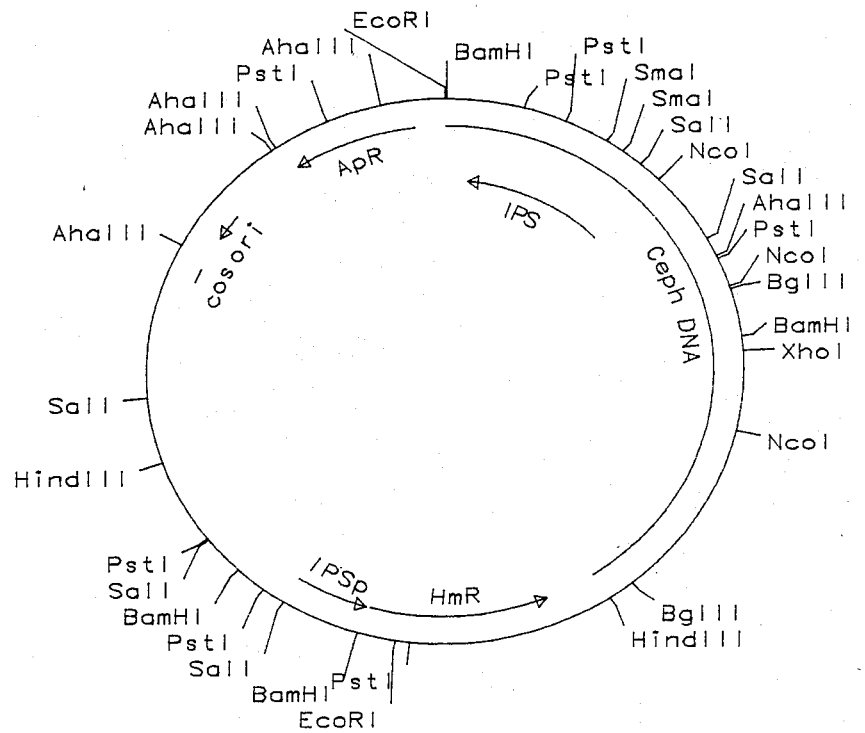
FIG. 12. A restriction site and function map of plasmid pPS26.

Yet another useful derivative was constructed using plasmid pPS21A as starting material. The ~3.45 kb HindIII restriction fragment of plasmid pPS21A was inserted into the single HindIII site of plasmid pIT335 to yield plasmids pPS26 and pPS26.1, which differ only with respect to the orientation of the inserted HindIII restriction fragment from plasmid pPS21A. Plasmids pPS26 and pPS26.1 comprise the intact IPS gene from *Cephalosporium acremonium* and the hygromycin resistance-conferring gene driven by the activating sequence of the IPS gene. The construction of plasmids pPS26 and pPS26.1 is described in Example 9, and a restriction site and function map of plasmid pPS26 is presented in FIG. 12 of the accompanying draings.

U.S. patent application Ser. No. 654,919, attorney docket no. X-6570, filed 9/27/84, describes the construction of a vector similar to plasmid pIT221, a plasmid which, as stated above, is also described and disclosed in the same application, but this similar vector further comprises *Cephalosporium acremonium* ribosomal RNA-encoding DNA. The plasmid, designated pPS6, has enhanced ability to integrate into *C. acremonium* chromosomal DNA due to the presence of the rRNA-encoding DNA. The construction of plasmid pPS6 is disclosed on pages 72 to 75, Example 13, of the above mentioned U.S. patent application Ser. No. 654,919, and the referenced Example 13 is incorporated herein by reference. Because plasmid pPS6 comprises the same PGK-HmR gene as does plasmid pIT221, the plasmid pPS6 derivative that results from replacing the PGK transcriptional and translational activating sequence with the *C. acremonium* activating sequence of the present invention is clearly within the scope of the present invention.

Plasmid pPS6 contains an ~3.7 kb XmaI restriction fragment that comprises rRNA genes of *Cephalosporium acremonium*. The presence of this XmaI fragment on a plasmid increases the likelihood that the plasmid will integrate into the *C. acremonium* genome by homologous recombination when the plasmid is transformed into *C. acremonium*. Thus, plasmids pPS30 and pPS30.1 were constructed by inserting the ~3.7 kb XmaI restriction fragment of plasmid pPS6 that comprises a portion of the *C. acremonium* rRNA genes into the single XmaI site of plasmid pPS21A; plasmids pPS30 and pPS30.1 differ only with respect to the orientation of the XmaI restriction fragment. Plasmids pPS31 and pPS31.1 were constructed by inserting the ~3.7 kb XmaI restriction fragment of plasmid pPS6 into the single XmaI site of plasmid pPS29. The construction of plasmids pPS30, pPS30.1, pPS31, and pPS31.1 is described in Example 10.

The plasmid vectors of the present invention that utilize the transcription and translation activating sequence of the *Cephalosporium acremonium* IPS gene to drive expression of the hygromycin resistance-conferring gene are far superior to plasmids that utilize the *Saccharomyces cerevisiae* PGK activating sequence to drive expression of the hygromycin resistance-conferring gene in *C. acremonium*. The superiority of the present vectors is demonstrated by two observations: (1) the transformation frequency, as measured by the number of hygromycin-resistant *Cephalosporium acremonium* transformants per microgram of vector DNA used in the transformation, is 50 to 300 times higher when the IPS activating sequence, as opposed to the PGK activating sequence, is used to drive expression of the hygromycin resistance-conferring gene on the vector; and (2) the protoplast regeneration time, as measured by the time it takes for colonies visible to the naked eye to appear after the transformation, under selective conditions is about 50% less when the IPS activating sequence, as opposed to the PGK activating sequence, is used to drive expression of the hygromycin resistance-conferring gene on the vector.

The *Cephalosporium acremonium* transcriptional and translational activating sequence can be used to express any DNA sequence in *C. acremonium*, as indicated by the expression vectors described above. Thus, the present invention comprises the use of the *C. acremonium* transcriptional and translational activating sequence encoded within the ~0.5 kb SalI-NcoI restriction fragment of plasmid pIT335 to drive expression of any DNA sequence that encodes a useful substance.

The present invention results from the cloning of an intact, functional, *Cephalosporium acremonium* DNA sequence that encodes not only the amino acid sequence of isopenicillin N synthetase but also the transcriptional and translational activating sequence necessary to drive expression of isopenicillin N synthetase in *C. acremonium*. Likewise, the IPS gene of the present invention comprises the sequences located downstream of the coding region that are responsible for terminating transcription and for providing the mRNA polyadenylation and processing signals. Usually, the sequences responsible for transcription termination, polyadenylation, and mRNA processing are encoded within the region ~500 bp downstream of the stop codon of the coding region. Therefore, the ~0.5 kb BamHI-PstI restriction fragment that comprises the IPS carboxy-terminal-encoding DNA and downstream sequences thereof also comprises the transcription termination and mRNA polyadenylation and processing signals of the IPS gene.

Figure 14:
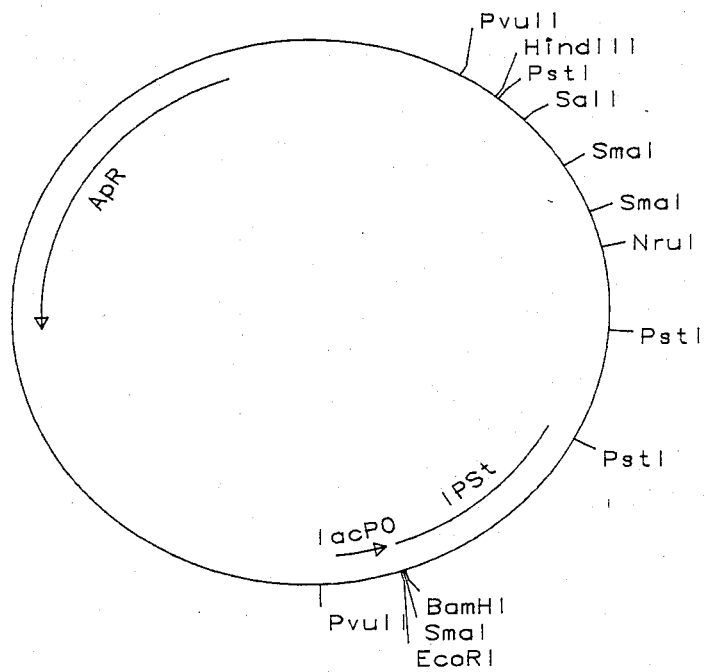
FIG. 14. A restriction site and function map of plasmid pIT336.

One vector, designated plasmid pPS27, has been constructed that contains the IPS transcription and translation activating sequence, followed by the hygromycin resistance-conferring gene, followed by the transcription termination and mRNA polyadenylation and processing signals of the IPS gene. To construct plasmid pPS27, the ~1.4 kb BamHI-XhoI restriction fragment of plasmid pIT335 was inserted into SalI-BamHI-digested plasmid pUC8 (SalI and XhoI overlaps are compatible) to yield plasmid pIT336 (FIG. 14).

Figure 15:
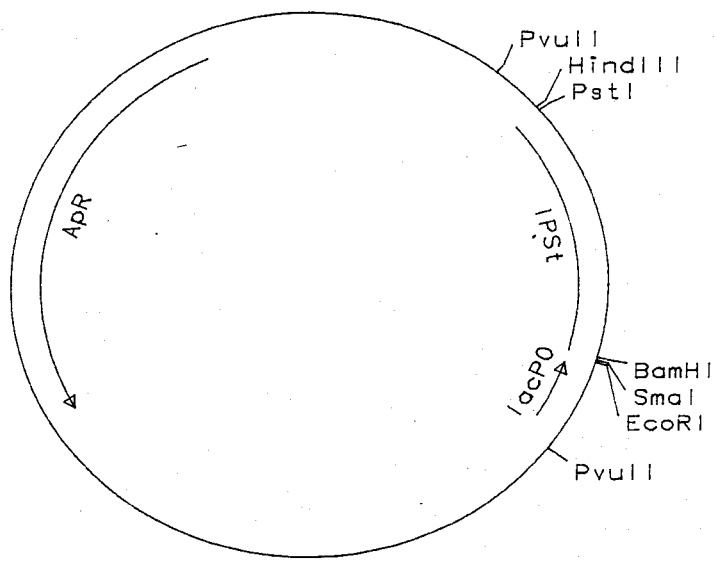
FIG. 15. A restriction site and function map of plasmid pPS35.

Plasmid pIT336 was digested with restriction enzyme PstI and recircularized to delete all of the Cephalosporium DNA sequences from the plasmid except the ~0.5 kb BamHI-PstI restriction fragment that comprises the transcription termination and mRNA polyadenylation and processing signals of the IPS gene to yield plasmid pPS35 (FIG. 15).

Figure 16:
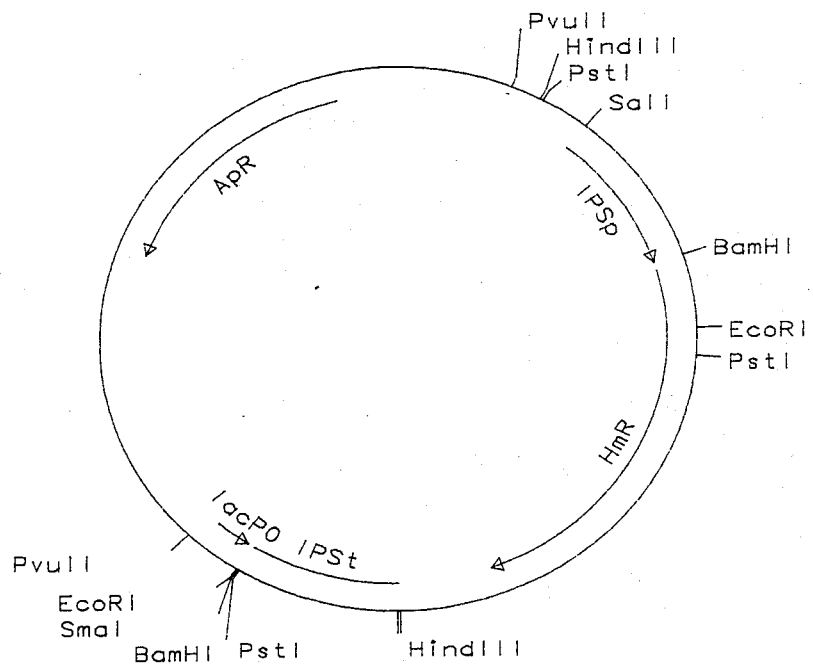
FIG. 16. A restriction site and function map of plasmid pPS27.
Figure 17:
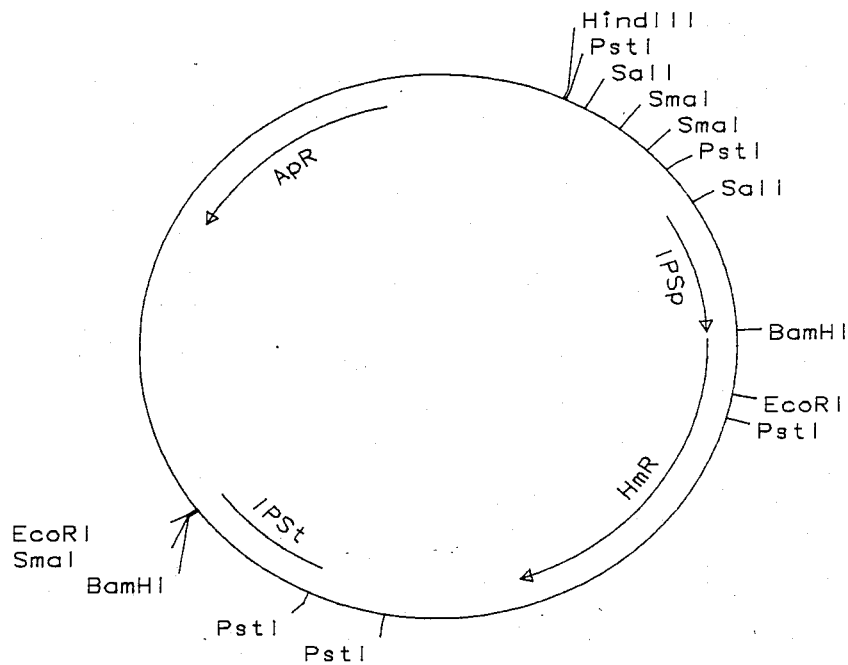
FIG. 17. A restriction site and function map of plasmid pPS37.

Plasmid pPS35 was then digested with restriction enzyme HindIII, and the ~2.3 kb HindIII restriction fragment of plasmid pPS29 that comprises the transcriptional and translational activating sequence of the IPS gene followed by the hygromycin resistance-conferring gene was inserted into HindIII-digested plasmid pPS35 in the proper orientation to yield plasmid pPS27. The construction of plasmid pPS27 is described in Example 11, and a restriction site and function map of plasmid pPS27 is presented in FIG. 16 of the accompanying drawings.

Figure 13:
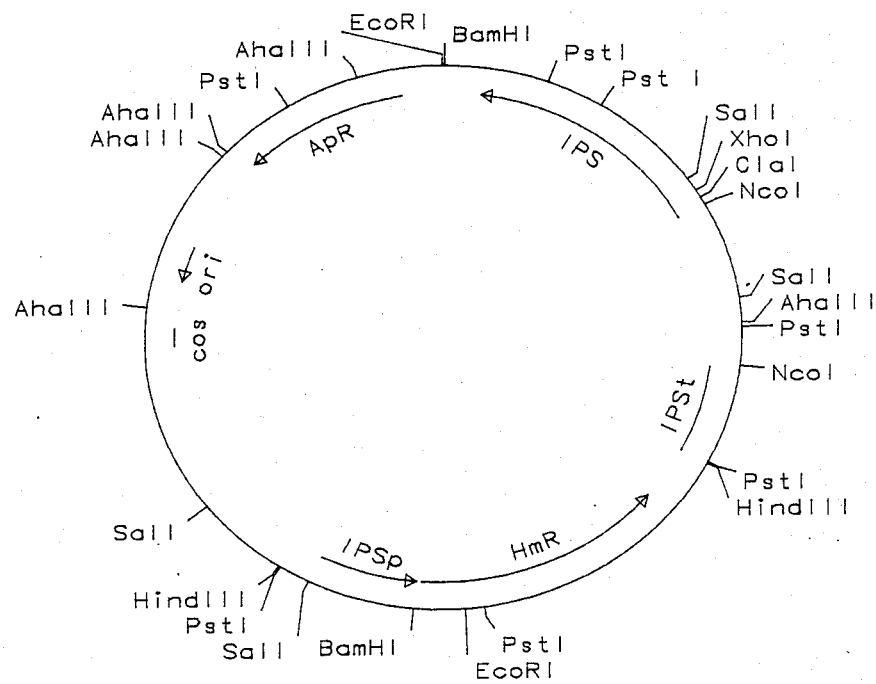
FIG. 13. A restriction site and function map of plasmid pPS34.

A useful derivative of plasmid pPS27 can be constructed by isolating the ~2.3 kb HindIII and ~0.5 kb HindIII-BamHI restriction fragments of plasmid pPS27 and inserting these fragments in the proper orientation into the ~5.9 kb BglII-HindIII restriction fragment of plasmid pIT335 to yield plasmid pPS34. Plasmid pPS34 comprises both the hygromycin resistance-conferring gene and also the isopenicillin N synthetase-encoding gene controlled by the regulatory elements of the IPS gene. A restriction site and function map of plasmid pPS34 is presented in FIG. 13 of the accompanying drawings.

Plasmid pIT336 can be used as starting material to construct a plasmid that will integrate into the *Cephalosporium acremonium* genome at the locus of the isopenicillin N synthetase gene. This plasmid, designated pPS37, has utility for insertional inactivation studies, for transformation of plasmid pPS37 into a *C. acremonium* strain will produce IPS-deficient mutants of that strain when plasmid pPS37 integrates into the coding region of the IPS gene. Plasmid pPS37 is constructed by inserting the ~3.45 kb HindIII restriction fragment of plasmid pPS21A, which comprises the hygromycin resistance-conferring gene under the control of the activating sequence of the IPS gene, into NruI-digested plasmid pIT336. Plasmid pIT336 has a single NruI site located in the portion of the IPS coding region present on the plasmid. The insertion of the ~3.45 kb HindIII restriction fragment, which is blunt ended by treatment with Klenow enzyme, into NruI-digested plasmid pIT336 actually produces two plasmids, designated pPS37 and pPS37.1, which differ only with respect to the orientation of the inserted fragment. Both plasmid pPS37 and plasmid pPS37.1 are useful to transform *C. acremonium* to obtain hygromycin-resistant, IPS-deficient transformants.

The present invention is a pioneering invention in that it represents the first cloning and genetic engineering of a DNA sequence that encodes the enzymatic activity, often called a cyclase activity, necessary to catalyze condensation of a tripeptide substrate into a substituted β-lactam. Many organisms other than *C. acremonium* express a substantially similar, if not identical, cyclase activity. The similarity of cyclase activity in antibiotic-producing organisms of different genera results from a corresponding similarity of the amino acid sequence of the different cyclases and of the DNA sequence encoding the cyclase activity.

The present invention provides both an amino acid and a DNA sequence for a cyclase enzyme, specifically the isopenicillin N synthetase of *Cephalosporium acremonium*, and thus can be used to isolate cyclase enzyme encoding DNA from β-lactam-producing organisms. For instance, the present DNA sequences can be used to prepare labelled probes that can, in turn, be used to find cyclase-encoding DNA sequences in the aforementioned β-lactam-producing organisms. The high G and C content of the present isopenicillin N synthetase-encoding DNA, ~63%, makes the present DNA compounds especially useful for isolating the *Streptomyces clavuligerus* isopenicillin N synthetase-encoding DNA. Streptomyces DNA is known to have high G and C content, often approaching 70%, so the high G and C content of the DNA of the present invention makes the present DNA compounds especially useful for isolating homologous *S. clavuligerus* or other streptomycetes IPS-encoding DNA sequences. The present invention comprises DNA compounds that encode cyclase activity and further comprises expression vectors that drive expression of that cyclase activity in a variety of host organisms.

The following Examples are provided to further illustrate and exemplify the present invention but are in no way intended to limit the scope of the present invention.

EXAMPLE 1

Culture of *E. coli* K12 JA221/pIT335 and Isolation of Plasmid pIT335

A. Culture of *E. coli* K12 JA221/pIT335

A lyophil of *E. coli* K12 JA221/pIT335 is obtained from the Northern Regional Research Laboratories, Peoria, Ill. under the accession number NRRL B-15960. The lyophil can be directly used as the "culture" in the process described below.

One liter of L-broth (10 g tryptone, 10 g NaCl, and 5 g yeast extract per liter) containing 50 μg/ml ampicillin was inoculated with a culture of *E. coli* K12 JA221/pIT335 and incubated in an air-shaker at 37° C. until the optical density at 590 nm (O.D.$_{590}$) was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

B. Isolation of Plasmid pIT335

The culture prepared in Example 1A was centrifuged in a Sorvall GSA rotor (DuPont Co., Instrument Products, Biomedical Division, Newtown, Conn. 06470) at 6000 rpm for 5 minutes at 4° C. The resulting supernatant was discarded, and the cell pellet was washed in 40 ml of TES buffer (10 mM Tris-HCl, pH=7.5; 10 mM NaCl; and 1 mM EDTA) and then repelleted. The supernatant was discarded, and the cell pellet was frozen in a dry ice-ethanol bath and then thawed. The thawed cell pellet was resuspended in 10 ml of a solution of 25% sucrose and 50 mM EDTA. About 1 ml of a 5 mg/ml lysozyme solution; 3 ml of 0.25 M EDTA, pH=8.0; and 100 μl of 10 mg/ml RNAse A were added to and mixed with the solution, which was then incubated on ice for 15 minutes. Three ml of lysing solution (prepared by mixing 3 ml 10% Triton-X 100; 75 ml 0.25 M EDTA, pH=8.0; 15 ml of 1 M Tris-HCl, pH=8.0; and 7 ml of water) were added to the lysozyme-treated cells, mixed, and the resulting solution incubated on ice for another 15 minutes. The lysed cells were frozen in a dry ice-ethanol bath and then thawed.

The cellular debris was removed from the solution by centrifugation at 25,000 rpm for 40 minutes in an SW27 rotor (Beckman, 7360 N. Lincoln Ave., Lincolnwood, Ill. 60646) and by extraction with buffered phenol. About 30.44 g of CsCl and ~1 ml of a 5 mg/ml ethidium bromide solution were added to the solution, which was then adjusted to a volume of 40 ml and decanted into a VTi50 ultra-centrifuge tube (Beckman). The tube was sealed, and the solution was centrifuged in a VTi50 rotor at 42,000 rpm for ~16 hours. The resulting plasmid band, visualized with ultraviolet light, was isolated and then placed in a Ti75 tube and rotor (Beckman) and centrifuged at 50,000 rpm for 16 hours. Any necessary volume adjustments were made using TES containing 0.761 g/ml CsCl. The plasmid band was again isolated, extracted with salt-saturated isopropanol to remove the ethidium bromide, and diluted 1:3 with TES buffer. Two volumes of ethanol were then added to the solution, which was then incubated at −20° C. overnight. The plasmid DNA was pelleted by centrifuging the solution in an SS34 rotor (Sorvall) for 15 minutes at 10,000 rpm.

The ~1 mg of plasmid pIT335 DNA obtained by this procedure was suspended in 1 ml of TE buffer (10 mM Tris-HCl, pH=8.0 and 1 mM EDTA) and stored at −20° C. A restriction site and function map of plasmid pIT335 is presented in FIG. 1 of the accompanying drawings.

EXAMPLE 2

Construction of Plasmid pIT337

A. Culture of E. coli K12 RV308/pCZ106 and Isolation of Plasmid pCZ106.

A lyophil of a culture of E. coli K12 RV308/pCZ106 is obtained from the Northern Regional Research Laboratories, Peoria, Ill., under the accession number NRRL B-15959. The lyophil is used to inoculate 1 liter of L-broth containing 50 μg/ml kanaan air-shaker until the O.D.$_{590}$ is between 0.5 and 1.0 absorbance units. When the culture reaches 0.5–1.0 absorbance units in optical density, the temperature is raised to 37° C., and incubation is continued for 2 to 6 hours. The runaway replicon, as stated previously herein, is temperature sensitive and loses copy number control at 37° C. The 2 to 6 hour incubation at 37° C. provides ample time for uncontrolled replication.

After the 2 to 6 hour incubation at 37° C., the cells are collected, and the plasmid pCZ106 DNA is isolated in substantial accordance with the procedure of Example 1B. About 5 mg of plasmid pCZ106 DNA is obtained and suspended in 5 ml of TE buffer. A restriction site and function map of plasmid pCZ106 is provided in FIG. 2 of the accompanying drawings.

B. NcoI and BamHI Digestion of Plasmid pCZ106 and Isolation of the ~8.7 kb NcoI-NcoI and ~1.6 kb NcoI-BamHI Restriction Fragments of Plasmid pCZ106

Approximately 25 μg, corresponding to 25 μl, of the plasmid pCZ106 DNA prepared in Example 2A were added to and mixed with 10 μl of 10X BamHI reaction buffer (1.5 M NaCl; 60 mM Tris-HCl, pH=7.9; 60 mM MgCl$_2$; and 1 mg/ml bovine serum albumin (BSA)), 5 μl (~50 units) of restriction enzyme* BamHI, 5 μl (~50 units) of restriction enzyme NcoI, and 55 μl of H$_2$O. The resulting reaction was incubated at 37° C. for four hours, after which time the reaction was essentially complete.

\* Unless otherwise noted, restriction and ligation enzymes were obtained from New England Biolabs, 32 Tozer Road, Beverly, Mass. 01915. Unit definitions herein correspond to the particular manufacturer's unit definitions.

The NcoI-BamHI reaction mixture was then electrophoresed on a 1% agarose gel until the desired 1.6 kb NcoI-BamHI and ~8.7 kb NcoI-NcoI fragments were clearly separated from the other digestion product, an ~0.3 kb restriction fragment. Visualization of the electrophoresed DNA was accomplished by staining the gel in a dilute solution (0.5 μg/ml) of ethidium bromide and exposing the stained gel to long-wave UV light. The desired fragments were located, and a small slit was made in the gel in front of each of the desired fragments. A small piece of Schleicher and Schuell (Keene, NH 03431) NA-45 DEAE membrane was placed in each slit. Upon further electrophoresis, the DNA non-covalently bound to the DEAE membrane. After the desired fragments were bound to the DEAE membrane, the membranes were removed and rinsed with low salt buffer (100 mM KCl; 0.1 mM EDTA; and 20 mM Tris-HCl, pH=8). Next, each membrane was placed in a small tube and immersed in high salt buffer (1 M NaCl; 0.1 mM EDTA; and 20 mM Tris-HCl, pH=8) and then incubated at 65° C. for one hour to remove the DNA from the DEAE paper. After the 65° C. incubation, the incubation buffer was collected and the membrane rinsed with high salt buffer. The rinse solution was pooled with the incubation buffer before collecting the desired DNA fragments.

The volume of the high salt-DNA solution was adjusted so that the NaCl concentration was 0.25 M, and then three volumes of cold, absolute ethanol were added. resulting solutions were mixed and placed at −70° C. for 10–20 minutes. The solutions were then centrifuged at 15,000 rpm for 15 minutes. After another precipitation to remove residual salt, the DNA pellets were rinsed with ethanol, dried, resuspended in 20 μl of ~1.6 kb NcoI-BamHI and ~8.7 kb NcoI-NcoI restriction fragments of plasmid pCZ106. The purified fragments obtained were individually dissolved in 25 μl of TE buffer and stored at −20° C.

C. NcoI and BamHI Digestion of Plasmid pIT335 and Isolation of the ~1.5 kb NcoI-BamHI Restriction Fragment that Encodes Isopenicillin N Synthetase Approximately 25 μg, corresponding to 25 μl, of the plasmid pIT335 DNA prepared in Example 1B were digested with restriction enzymes NcoI and BamHI in substantial accordance with the procedure of Example 2B. The NcoI-BamHI-digested DNA obtained was loaded onto a 1% agarose gel and the desired ~1.5 kb NcoI-BamHI restriction fragment was isolated in substantial accordance with the procedure of Example 2B. Approximately 5 μg of the desired fragment were obtained, suspended in 25 μl of TE buffer, and stored at −20° C.

D. Final Construction of Plasmid pIT337

Five μl of the ~1.6 kb NcoI-BamHI and 2.5 μl of the ~8.7 kb NcoI-NcoI restriction fragments of plasmid pCZ106 purified in Example 2B were ligated to five μl of the ~1.5 kb NcoI-BamHI restriction fragment of plasmid pIT335 purified in Example 2C to form plasmid pIT337. The reaction volume was 30 μl and comprised the aforementioned DNA fragments, 1.1 μl (~100 units) of T4 DNA ligase, 3 μl of 10X ligation buffer (0.5 M Tris-HCl, pH=7.8; 100 mM MgC$_2$; 200 mM dithiothreitol (DTT); 10 mM ATP; and 1 mg/ml BSA), and 13.4 μl of H$_2$O. The reaction was incubated at 15° C. for 2 hours, after which time the reaction was essentially complete. The ligated DNA constituted the desired plasmid pIT337 DNA. A restriction site and function map of plasmid pIT337 is presented in FIG. 3 of the accompanying drawings.

EXAMPLE 3

Construction of *E. coli* K12 RV308/pIT337 and Assay of *E. coli*-Produced Isopenicillin N Synthetase

A. Construction of *E. coli* K12 RV308/pIT337

A 50 ml culture of *E. coli* K12 RV308 (NRRL B-15624) in L-broth was grown to an O.D.$_{590}$ of ~0.5 absorbance units. The culture was chilled on ice for ten minutes, and the cells were collected by centrifugation. The cell pellet was resuspended in 25 ml of cold 100 mM CaCl$_2$ and incubated on ice for 25 minutes. The cells were once again pelleted by centrifugation, and the pellet was resuspended in 2.5 ml of cold 100 mM CaCl$_2$ and incubated on ice overnight.

Two hundred μl of this cell suspension were mixed with the ligated DNA prepared in Example 2D and incubated on ice for 20 minutes, and then the cells were collected by centrifugation. The cell pellet was resuspended in ~1 ml of L-broth, and the suspension was incubated at 25° C. for one hour. Aliquots of the cell mixture were plated on L-agar (L-broth with 15 g/l agar) plates containing 50 μg/ml kanamycin, and the plates were incubated at 25° C. *E. coli* K12 RV308/pIT337 transformants were verified by selection for kanamycin resistance and by restriction enzyme analysis of the plasmid DNA of the transformants. Plasmid DNA was obtained from the *E. coli* K12 RV308/pIT337 transformants in substantial accordance with the teaching of Example 2A, but on a smaller scale, and the CsCl-gradient steps were omitted.

B. Culture of *E. coli* K12 RV308/pIT337 for Expression of Isopenicillin N Synthetase Activity Several isolates of the *E. coli* K12 RV308/pIT337 transformants prepared in Example 3A were individually inoculated into 5 ml aliquots of L-broth containing 50 μg/ml kanamycin, and the cultures were incubated in an air-shaker at 25° C. until the O.D.$_{590}$ was ~0.2 absorbance units. The cultures were then transferred to a 37° C. air-shaker and incubated at 37° C. for ~6 hours.

After the six-hour, 37° C. incubation, one ml of each culture was collected, and the cells were pelleted by centrifugation. The cell pellets were individually washed with 1 ml of 10 mM NaCl and then resuspended in 1.0 ml of IPS extraction buffer (0.05 M Tris-HCl, pH=8.0; 0.01 M KCl; and 0.01 M MgSO$_4$). The cells were sonicated by six, five-second bursts of sonication delivered by a Sonifier Cell Disruptor, Model W185, Heat Systems-Ultrasonics, Inc., Plainview, Long Island, N.Y., using the micro tip. The time between bursts of sonication was 60 seconds, and the mixture was kept in an ice-ethanol bath during the procedure. After sonication, the cell mixture was centrifuged to remove debris and then used directly in the assay.

C. Assay for Isopenicillin N Synthetase Activity

The following assay procedure is derived from the procedure of Shen et al., 1984, J. of Antibiotics 37(9): 1044–1048.

The isopenicillin N synthetase assay reaction was carried out in a total volume of 500 μl. To start the reaction, 1.0 ml of a solution of 1.4 mM δ-(L-α-aminoadipyl)-L-cysteinyl-D-valine and 3.75 mM DTT was allowed to react at room temperature for 30–60 minutes to reduce any dimeric tripeptide to the monomeric form. Fifty μl of each of the following stock solutions were aliquoted into each assay tube (sterile, glass, disposable 13×100 mm tubes): 500 mM Tris-HCl, pH=7.4; 100 mM KCl; 100 mM MgSO$_4$; 2.0 mM FeSO$_4$; and 6.7 mM asorbic acid. Next, varying amounts of extract, diluted with water to a volume of 150 μl, were added. About 100 μl aliquots of the tripeptide solution were then added to each tube; the addition of the tripeptide starts the reaction. Each tube was vortexed upon addition of the substrate. The reaction mixture vessels were then placed in a gyrotory shaker bath at 250 rpm, with an incubation temperature of 25° C. The reaction time was 45 minutes.

After 45 minutes of reaction, 2 samples of 100 μl each were withdrawn and dispensed into wells in the bioassay plats, and 100 units of penicillinase A were added to the remainder of the sample. The penicillinase A was obtained from Riker's Laboratories, Inc.; the enzyme is sold in vials of 100,000 units, which were rehydrated to 5.0 mls with H$_2$O. Five μl (100 units) of the rehydrated pencillinase A were added to the remainder of each reaction mixture, allowed to react for 5 minutes at room temperature, and then 100 μl of each penicillinase A-treated extract were dispensed into the wells of a bioassay plate. This penicillinase A treatment is done to check that the zones on the bioassay plate are due to the presence of a penicillin rather than a cephalosporin or other contaminant.

The penicillin N standard curve was prepared by adding 0.5, 1.0, 2.0, 5.0, 10.0, and 20.0 μg of penicillin N to bioassay wells. The penicillinase A activity was also checked by adding 5 μl of the enzyme preparation to ~200 μl of 0.2 μg/ml penicillin N. The bioassay plates were composed of K131 nutrient agar, which is prepared by dissolving 30.5 g BBL Antibiotic Medium #11 (Becton Dickinson & Company, Cockeysville, Md.) in 1 liter of deionized water, bringing the solution to a boil, cooling to 70° C., and then autoclaving 35 minutes at 121° C. and 15 psi. The plates were seeded with 4 mls of fresh overnight culture of Micrococcus luteus (ATCC 9341) per 700 ml of agar. The M. luteus was grown in K544 nutrient broth, which is composed of: Difco peptone, 5.0 g; Difco yeast extract, 1.5 g; sodium chloride, 3.5 g; dipotassium phosphate (anhydrous), 3.7 g; monopotassium phosphate, 1.3 g; Difco beef extract, 1.5 g, in 1 liter of deionized water—the solution is brought to a boil, cooled to 25° C., adjusted to a pH=7.0 with 1 N HCl or 1 N NaOH, and then autoclaved for 20 minutes at 121° C. and 15 psi before use. The seeded agar was dispensed into 100×15 mm plates, at 15 mls of seeded agar per plate. The wells were prepared by applying suction using a disposable 5 ml pipette; each well was 10 mM in diameter.

After the plates were prepared and the samples were dispensed into the wells, the plates were placed in a 37° C. incubator for 18 hours. The assay results are determined by measuring the diameter of the cleared areas around each sample well, which result from the $M.$ luteus being unable to grow when a penicillin is present.

The results of the assay are tabulated below.

TABLE II

Isopenicillin N Synthetase Activity of Cell Extracts from $E.$ coli K12 RV308/pIT337

| Sample | Zone Size (mm) |
|---|---|
| 2 µg penicillin N standard | 16 |
| 5 µg penicillin N standard | 18 |
| 10 µg penicillin N standard | 27 |
| 20 µg penicillin N standard | 31 |
| 25 µl $E.$ coli K12 RV308/pIT337 cell extract | 10 |
| 50 µl $E.$ coli K12 RV308/pIT337 cell extract | 22 |
| 100 µl $E.$ coli K12 RV308/pIT337 cell extract | 27 |
| 150 µl $E.$ coli K12 RV308/pIT337 cell extract | 29 |
| All penicillinase-treated samples | 0 |
| $E.$ coli K12 RV308/pCZ106 cell extract control | 0 |
| Control reactions without substrate | 0 |

Although the linearity of the assay, as measured by zone size, drops off markedly when zone size increases above 21 mm, the results of the assay clearly indicate that the $E.$ coli K12 RV308/pIT337 transformants express isopenicillin N synthetase activity, whereas the $E.$ coli K12 RV308/pCZ106 transformants do not.

The $E.$ coli-produced material is substantially more stable than isopenicillin N synthetase derived from Cephalospoium acremonium. This greater stability was first observed in freeze-thaw experiments. The $C.$ acremonium isopenicillin N synthetase activity is quickly inactivated by refreezing and rethawing, but the $E.$ coli-produced isopenicillin N synthetase activity of the present invention is quite resistant to freezing and thawing.

The greater stability probably results from a difference in processing of the enzyme between $C.$ acremonium and $E.$ coli. For instance, the isopenicillin N synthetase activity isolated from $C.$ acremonium does not appear to have the first two amino-terminal amino acid residues, methionine and glycine, which are encoded in the $C.$ acremonium isopenicillin N synthetase activity-encoding DNA and which are also present in the $E.$ coli produced material of the present invention. As disclosed in Tsunasawa et al., 1985, J. of Biol. Chem. 260(9):5382-91, $E.$ coli produces a peptidase that cleaves the amino-terminal methionine residue of a protein when the following residue has a relatively small side chain. In the IPS protein, the amino-terminal methionine is followed by a glycine residue, so the amino-terminal methionine is cleaved in $E.$ coli.

In view of the greater stability and different amino acid residue sequence of the $E.$ coli-produced isopenicillin N synthetase activity, the present invention also comprises a novel protein: $E.$ coli-produced isopenicillin N synthetase.

EXAMPLE 4

Construction of Plasmid pPS20

A. Preparation of HindIII-Digested Plasmid pIT335

Five µl of the plasmid pIT335 DNA prepared in Example 1B, which correspond to ~5 µg of plasmid DNA, were added to and mixed with 5 µl of 10X HindIII reaction buffer (500 mM NaCl; 500 mM Tris-HCl, pH=8.0; 100 mM MgCl$_2$; and 1 mg/ml BSA), 5 µl (~50 units) of restriction enzyme HindIII, and 35 µl of H$_2$O. The resulting reaction was incubated at 37° C. for four hours. The HindIII-digested plasmid pIT335 DNA was extracted once with phenol and then extracted once with CHCl$_3$. After the extractions, the HindIII-digested plasmid pIT335 DNA was made 0.25 M in NaCl, diluted with two volumes of absolute ethanol, chilled in a dry ice-ethanol bath, and then the precipitated DNA was collected by centrifugation. The ~5 µg of HindIII-digested plasmid pIT335 DNA obtained by this procedure were dissolved in 10 µl of TE buffer and stored at −20° C.

B. HindIII Digestion of Plasmid pIT221 and Isolation of the ~2.7 kb HindIII Restriction Fragment of Plasmid pIT221 that Comprises a Hygromycin Resistance-Conferring Gene U.S. patent application Ser. No. 654,919, filed 9/27/84, attorney docket number X-6570, discloses vectors and conditions for transforming Cephalosporium acremonium. Construction flow sheets 1-6 and Examples 1-6 of U.S. patent application Ser. No. 654,919, incorporated herein by reference, disclose the construction of plasmid pIT221. A restriction site and function map of plasmid pIT221 is provided in FIG. 4 of the accompanying drawings.

Plasmid pIT221 was isolated from $E.$ coli K12 JA221-/pIT221 in substantial accordance with the procedure of Example 1 of the present application. About 50 µg of plasmid pIT221 were digested in 100 µl of 1X HindIII reaction buffer with 100 units of restriction enzyme HindIII in substantial accordance with the procedure of Example 4A. The HindIII-digested plasmid pIT221 DNA was extracted, precipitated, and redissolved in accordance with the procedure of Example 4A, and the DNA was loaded onto a 1% agarose gel for electrophoresis. The desired ~2.7 kb HindIII restriction fragment of plasmid pIT221 that comprises the yeast Saccharomyces cerevisiae phosphoglycerate kinase transcriptional and translational activating sequence and encodes a hygromycin resistance-conferring phosphotransferase enzyme was isolated and purified from the gel and other digestion products in substantial accordance with the procedure of Example 2B.

About 5 µg of the desired ~2.7 kb HindIII restriction fragment were isolated by the foregoing method. The purified fragment obtained was dissolved in 10 μl of TE buffer and stored at −20° C.

C. Final Construction of Plasmid pPS20

About 1 μl of the HindIII-digested plasmid pIT335 DNA prepared in Example 4A and 4 μl of the ~2.5 kb HindIII restriction fragment of plasmid pIT221 prepared in Example 4B were ligated in 30 μl of ligation buffer with 100 units of T4 DNA ligase in substantial accordance with the procedure of Example 2C. The ligated DNA constituted the desired plasmid pPS20. A restriction site and function map of plasmid pPS20 is presented in FIG. 5 of the accompanying drawings.

The ~2.7 kb HindIII restriction fragment could insert into plasmid pIT335 in either of two orientations, so the ligated DNA also constituted another plasmid, designated plasmid pPS20.1. Plasmid pPS20.1 is functionally equivalent to plasmid pPS20 and differs from plasmid pPS20 only with respect to the orientation of the ~2.7 kb HindIII restriction fragment.

D. Construction of E. coli K12 JA221/pPS20 and Isolation of Plasmid pPS20 DNA A 50 ml culture of E. coli K12 JA221 (NRRL B-15211) in L-broth was grown to an O.D.$_{590}$ of ~0.2. The culture was chilled on ice for ten minutes, and the cells were collected by centrifugation. The cell pellet was resuspended in 25 ml of cold 100 mM CaCl$_2$ and incubated on ice for 25 minutes. The cells were once again pelleted by centrifugation, and the pellet was resuspended in 2.5 ml of cold 100 mM CaCl2 and incubated on ice overnight.

Two hundred μl of this cell suspension were mixed with the ligated DNA prepared in Example 4C and incubated on ice for 20 minutes. The mixture was then incubated at 40° C. for 2 minutes, followed by a 10 minute incubation at room temperature. Three ml of L-broth were added to the cell mixture, and then the cells were incubated in an air-shaker at 37° C. for two hours.

Aliquots of the cell mixture were plated on L-agar (L-broth with 15 g/l agar) plates containing 100 μg/ml ampicillin, and the plates were then incubated at 37° C. E. coli K12 JA221/pPS20 transformants were verified by restriction enzyme analysis of the plasmid DNA of the ampicillin-resistant transformants. Plasmid DNA was obtained from the E. coli K12 JA221/pPS20 and E. coli K12 JA221/pPS20.1 transformants in substantial accordance with the procedure of Example 1, but on a smaller scale, and the CsCl gradient steps were omitted.

EXAMPLE 5

Construction of Plasmid pPS21

A. NcoI Digestion and Klenow Treatment of Plasmid pIT335 DNA and Isolation of the Resulting ~0.85 kb Fragment that Encodes a Cephalosporium acremonium Transcriptional and Translational Activating Sequence Approximately 50 μl, corresponding to 50 μg, of the plasmid pIT335 DNA prepared in Example 1 are added to and mixed with 10 μl 10X BamHI buffer, 5 μl (~50 units) restriction enzyme NcoI, and 35 μl of H$_2$O. The resulting reaction is incubated at 37° C. for four hours. The reaction mixture is then made 0.25 M in NaCl, diluted with two volumes of absolute ethanol, chilled for 10 minutes in a dry ice-ethanol bath, and centrifuged to pellet the precipitated DNA.

The NcoI-digested plasmid pIT335 DNA pellet is dissolved in 50 μl of 1X Klenow buffer (40 mM KPO$_4$, pH=7.5; 6.6 mM MgCl$_2$; 1.0 mM 2-mercaptoethanol; 33 μM dATP; 33 μM dCTP; 33 μM dGTP; and 33 μM TTP). Two μl (~10 units, New England Biolabs) of the large fragment of E. coli DNA polymerase I, known as Klenow, are added to and mixed with the DNA, and the resulting reaction is incubated at 16° C. for one hour. The reaction is terminated by a buffered phenol extraction.

The NcoI-digested, Klenow-treated plasmid pIT335 DNA is then loaded onto a 1% agarose gel for electrophoresis. The ~0.85 kb restriction fragment that comprises the Cephalosporium acremonium transcriptional and translational activating sequence of the IPS gene is isolated from the gel and purified in substantial accordance with Example 2B. About 4 μg of the desired fragment are obtained and suspended in 10 μl of TE buffer.

B. Construction of Intermediate Plasmid pPS19

One μg of plasmid pIT221 DNA was dissolved in five μl of 10X XmaI buffer (250 mM NaCl; 60 mM Tris-HCl, pH=7.5; 60 mM MgCl$_2$; 60 mM 2-mercaptoethanol; and 1 mg/ml BSA), 43 μl of H$_2$O and 2 μl (~10 units) of restriction enzyme XmaI. The resulting reaction was incubated at 37° C. for four hours. The reaction was terminated by a phenol extraction. After further extracting the XmaI reaction mixture with CHCl$_3$, the reaction mixture was made 0.25 M in NaCl, diluted with 2 volumes of absolute ethanol, chilled for 10 minutes in a dry ice-ethanol and the precipitated, XmaI-digested plasmid pIT221 DNA was pelleted by centrifugation.

The XmaI-digested plasmid pIT221 DNA was redissolved in 100 μl of 1X ligation buffer containing 500 units of T4 DNA ligase. The ligation reaction was incubated at 12° C. for ~16 hours and then used to transform E. coli K12 JA221 in substantial accordance with the procedure of Example 4D. The ampicillin-resistant, plasmid pPS19 transformants were identified by restriction enzyme analysis of the plasmid DNA of the transformants. Plasmid pPS19 DNA was prepared from the transformants in substantial accordance with the procedure of Example 1. A restriction site and function map of plasmid pPS19 is presented in FIG. 6 of the accompanying drawings.

C. BamHI Digestion and Klenow Treatment of Plasmid pPS19 DNA and Isolation of the ~7.7 kb Fragment Fifty μg of plasmid pPS19 DNA are digested with restriction enzyme BamHI and treated with Klenow in substantial accordance with the procedure of Example 5A, except that BamHI restriction enzyme, rather than NcoI restriction enzyme, is used to digest the plasmid pPS19 DNA. The BamHI-digested, Klenow-treated plasmid pPS19 DNA is loaded onto a 1% agarose gel, and the ~7.7 kb fragment was isolated and purified in substantial accordance with the procedure of Example 2B. About 5 μg of the desired fragment are obtained, dissolved in 10 μl of TE buffer, and stored at −20° C.

Final Construction of Plasmid pPS21

Two μl of the ~0.85 kb fragment prepared in Example 5A are ligated to two μl of the ~7.7 kb fragment prepared in Example 5C in 30 μl of 1X ligation buffer containing 500 units of T4 DNA ligase. The ligation reaction is incubated at 12° C. for 16 hours, and the ligated DNA constitutes the desired plasmid pPS21 DNA.

E. Construction of *E. coli* JA221/pPS21

The ligated DNA prepared in Example 5D is used to transform *E. coli* K12 JA221 in substantial accordance with the procedure of Example 4D. The ampicillin-resistant transformants are screened for the presence of plasmid pPS21 by restriction enzyme analysis of the plasmid DNA of the transformants. Because the ~0.85 kb fragment could insert into the ~7.7 kb fragment of plasmid pPS19 in either one of two orientations, and because only one orientation correctly positions the *Cephalosporium acremonium* transcriptional and translational activating sequence for expression of the hygromycin resistance-conferring gene, only about half of the transformants are the desired *E. coli* K12 JA221/pPS21. One such *E. coli* K12 JA221/pPS21 transformant is used to prepare plasmid pPS21 DNA in substantial accordance with the procedure of Example 1.

EXAMPLE 6

Genetic Transformation of *Cephalosporium acremonium* with Plasmids pPS20 and pPS21

U.S. patent application Ser. No. 654,919, filed 9/27/84, discloses a similar transformation procedure for *Cephalosporium acremonium*. An improved method for transforming *C. acremonium* is described in Example 14.

A. *Cephalosporium acremonium* Strains

The preferred Cephalosporium strain for transformation is obtained from the American Type Culture Collection, Rockville, Md., under the accession number ATCC 11550. Other Cephalosporium strains or any commercial strains derived from ATCC 11550 by mutation, selection, or genetic breeding for the purpose of improved production of cephalosporin C are also suitable for use in preparing transformants with the vectors and plasmids of the present invention.

B. Preparation of Inoculum for Cell Culture

To transform *Cephalosporium acremonium* cells efficiently, it is necessary to remove the cell walls to form stable protoplasts. In the preparation of such protoplasts, it is highly advantageous to begin with a uniform inoculum. Otherwise, preparation of cells in is not reproducible and time is lost by attempts to prepare *C. acremonium* protoplasts from unsuitable or inadequate amounts of cells.

C. Preparation of Uniform Inoculum for Cell Culture

An ampoule of spores (approximately $10^9$ conidia in 1.5 ml of preservation menstrum: 5% lactose, 10% glycerol, and 0.1% Tween 80), either lyophilized or taken from liquid nitrogen storage and thawed at room temperature, are diluted in 5 ml of sterile saline. About 0.1 ml of this suspension is used to inoculate each of approximately 50 slants containing 20 ml of Trypticase ®-Soy Agar (BBL ™, Division of Becton, Dickinson & Company, Cockeysville, Md. 21030) medium. Before inoculation, the medium is allowed to dry until surface moisture is no longer visible. Inoculated slants are incubated for about four days at 25° C. About 10 ml of preservation menstrum are added to the mycelial growth that covers the surface of the medium in each slant. The slants are vortexed to suspend the conidia, and the conidial suspension from each slant is pooled and 10 ml aliquots frozen at −80° C. The frozen conidial suspension slowly loses viability and should not be used after about three months of storage at −80° C.

D. Growth of Cells for Preparation of Protoplasts

Approximately 106 ml of aqueous medium in a 500 ml shake flask are inoculated with cells from the 10 ml of frozen conidial suspension prepared in Example 6C. Cells are obtained by centrifugation (10 min X 2600 rpm) and then directly suspended in the aqueous culture medium*. Decantation of the supernatant is necessary prior to suspension, because the lactose and glycerol adversely affect the growth of cells. The flask containing the suspended cells is placed on a gyrotory water bath shaker and incubated at 29°–30° C. for 24 hours at 285 rpm with a 1 inch throw. The recommended temperature of 29°–30° C. in the culturing step is especially preferred for preparing transformable protoplasts, but lower temperatures of about 25° C. are also suitable. Those familiar with the art will recognize that the 29°–30° C. is different from the temperature (25° C.) preferred for culturing *Cephalosporium acremonium* for purposes of antibiotic production.

*Aqueous culture medium was prepared as follows: one hundred ml of solution A is dispensed into a 500 ml shake flask; the flask are covered with a commercial closure and is autoclaved at 121° C. for 20 minutes. Two ml of solution B and 4 ml of solution C are then added to solution A to prepare the aqueous culture medium.
Solution A: Sucrose, 36 g/L; L-asparagine, 7.5 g/L; $KH_2PO_4$, 15 g/L; $K_2HPO_4$, 21 g/L; $Na_2SO_4$, 75 g/L; $MgSO_4 7H_2O$; 0.18 g/L; $CaCl_2$, 0.06 g/L; salts solution, 1 ml/L; natural pH. Salts solution: $Fe(NH_4)(SO_4)_2 \cdot 6H_2O$, 15 g/L; $MnSO_4 \cdot 4H_2O$, 3 g/L; $ZnSO_4 \cdot 7H_2O$, 3 g/L; $CuSO_4 \cdot 5H_2O$, 0.8 g/L).
Solution B: Glucose, 108 g/L (autoclaved at 121° C., 30 minutes)
Solution C: Sucrose, 25 g/L; corn steep liquor (4% w/v nitrogen), 12.5 ml; ammonium acetate, 5.5 g/L; $CaCO_3$, 5 g/L; pH adjusted to 6.5 with KOH; and autoclaved at 121° C. for 20 minutes.

E. Preparation of Cephalosporium Protoplasts

Cells from a 24 hour culture are harvested by suction filtration (Whatman #1 paper in a Buchner funnel) and suspended in McIlvaine's Buffer, pH=7.1, (0.1 M citric acid and 0.2 M dibasic sodium phosphate) to which dithiothreitol has been added to a concentration of 0.01 M. Sufficient buffer is added to obtain a final cell concentration of 1 g (weighed after suction filtration) of cell mass per 20 ml of buffer. The cell suspension is placed on a gyrotory water bath shaker in a 50 ml shake flask and incubated at 29°–30° C. for 90 minutes at 140 rpm with a 1 inch throw. Dithothreitol treated cells are washed with water and then resuspended in enzyme solution (25 mg/ml of beta-glucuronidase from Sigma Chemical Company, in McIlvaine's buffer, pH=6.35, and supplemented with 0.8 M NaCl and 0.02 M $MgSO_4$) The final cell concentration is 1 g of treated cell mass per 10 ml of enzyme solution. The cell suspension is then placed on a gyrotory water bath shaker at 29°–30° C. for 3 hours at 120 rpm with a 1 inch throw. The suspension of protoplasts is diluted with 4 volumes of washing solution (0.8 M NaCl and 0.02 M $MgSO_4$) and then gravity filtered through two layers of paper towels. The filtrate containing the protoplasts is centrifuged at room temperature for 5 minutes at 2600 rpm. The supernatant is decanted, and the pellet of protoplasts is suspended in 10 ml of washing solution. After repeating the washing procedure twice, the protoplasts are resuspended in sufficient 0.8 M NaCl to achieve a concentration of 2 to $3 \times 10^8$ protoplasts per ml, by hemacytometer count.

F. Transformation Procedure

For each plasmid to be transformed, a 1 ml suspension of Cephalosporium protoplasts (2 to 3×10$^8$ per ml) in 0.8 M NaCl is added to 0.005 ml of freshly distilled DMSO and then made 80 mM in CaCl$_2$. About 20 μg of transforming plasmid, either pPS20 or pPS21, depending on the transformation, and polyethylene glycol 4000 (Baker, >20% w/v in water) are added to the suspension of protoplasts to achieve a mixture with a volume of 10 ml. The mixture is incubated for 10 minutes at room temperature and then centrifuged at 700 rpm for 5 minutes, which is followed by a 2500 rpm centrifugation for 10 minutes. The pellet of protoplasts is suspended in 1 ml of 0.8 M NaCl. Aliquots (0.1 ml) are delivered to the surface of Trypticase-Soy Agar medium (BBL) that has been enriched with 10.8% sucrose to osmotically stabilize the protoplasts. After the petri plates are incubated at 15° C. for 24 hours, 4 ml of liquified agar (0.41% w/v, at 42° C.) containing 0.8 M sodium chloride and sufficient hygromycin to achieve a final concentration of 100 μg/ml are added to each petri dish. After the overlay has solidified, the petri plates are then incubated at 25° C. in a humidified chamber. For cells transformed with a plasmid that contains only the PGK activating sequence for purposes of driving expression of the hygromycin resistance-conferring gene, transformant colonies of sufficient size to subculture are usually present 12 days after transformation, although slower growing transformants may take as long as 60 days to achieve a suitable size for subculture. Abortive transformants are easily distinguished from stable transformants, because abortive transformants fail to grow upon subculture to fresh medium containing 100 μg/ml of hygromycin. Cells transformed with a plasmid that contains the IPS activating sequence for purposes of driving expression of the hygromycin resistance-conferring gene from visible colonies within a few days after transformation.

G. Analysis of Cephalosporium acremqnium/pPS20 and C. acremonium/pPS21 Transformants Cephalosporium acremonium/pPS20 transformants express significantly higher levels of isopenicillin N synthetase activity than do C. acremonium transformants of control plasmids, such as plasmid pIT221. This higher level of activity results in an increased ability of the transformants to make isopenicillin N, whether in fermentation or in cell extracts of the C. acremonium/pPS20 transformants.

Cephalosporium acremonium/pPS21 transformants are hygromycin-resistant, which indicates the functionality of the C. acremonium transcriptional and translational activating sequence of the present invention.

EXAMPLE 7

Construction of Plasmids pPS21A, pPS22, pPS23, pPS23.1, pPS24, pPS25, and pPS25.1

A. Construction of Intermediate Plasmids pPS23 and pPS23.1

(i) Preparation of BamHI-digested plasmid pUC8.

About 5 μg of plasmid pUC8 (obtained from Pharmacia P-L Biochemicals) were dissolved in 5 μl of 10X BamHI reaction-buffer and 40 μl of H$_2$O. About 5 μl (50 units) of restriction enzyme BamHI were added to the solution of DNA, and the resulting reaction was incubated at 37° C. for two hours. The reaction was terminated by extraction with buffered phenol, followed by extraction with chloroform. The BamHI-digested plasmid pUC8 DNA was precipitated by adjusting the NaCl concentration to 0.25 M, adding 2 volumes of ethanol, and chilling at −70° C. for 10 minutes. The BamHI-digested plasmid pUC8 DNA was collected by centrifugation and resuspended in 5 μl of H$_2$O.

(ii) Isolation of the ~0.85 kb coI restriction fragment of plasmid pIT335.

About 10 μg of plasmid pIT335 were dissolved in 5 μl of 10X BamHI buffer and 40 μl of H$_2$O. About 5 μl (50 units) of restriction enzyme NcoI were added to the solution of DNA, and the resulting reaction was incubated at 37° C. for two hours. The reaction mixture was then loaded onto a 1% agarose gel, and the desired ~0.85 kb NcoI restriction fragment that comprises the transcription and translation activating sequence of the IPS gene was isolated in substantial accordance with the procedure of Example 2B. About 1 μg of the desired fragment was obtained and suspended in 5 μl of H$_2$O.

(iii) Preparation of the linker used in the construction of plasmid pPS23.

The single-strands of the following linker were synthesized using an automated DNA synthesizer:

About 75 picomoles of each single strand of the linker were individually dissolved in 22.5 μl of H$_2$O and 2.5 μl of ligase buffer. About 1 μl (10 units) of T4 DNA kinase (Bethesda Research Laboratories) was added to each solution of single-stranded DNA, and the reactions were incubated at 37° C. for 10 minutes. Following the kinase reaction, the reaction mixtures were incubated at 70° C. for 15 minutes. Then, to anneal the single-stranded DNA to form the linker, the two reaction mixtures were pooled, incubated at 65° C. for 10 minutes, incubated at room temperature for 2 hours, and then incubated at 4° C. overnight.

(iv) Final Construction of plasmids pPS23 and pPS23.1.

One μl of the BamHI-digested plasmid pUC8 DNA was added to a mixture of 4 μl of the ~0.85 kb NcoI restriction fragment of plasmid pIT335 and 10 μl of the annealed linker. About 4 μl of 10X ligase buffer, 2 μl (500 units) T4 DNA ligase, and 29 μl of H$_2$O were added to the mixture of DNA, and the resulting reaction was incubated at 4° C. overnight. The ligated DNA constituted the desired plasmids pPS23 and pPS23.1.

A 50 ml culture of E. coli K12 JM109, available from Pharmacia P-L Biochemicals, in L-broth was grown to an O.D.$_{590}$ of approximately 0.5 absorbance units. The culture was chilled on ice for ten minutes, and the cells were collected by centrifugation. The cell pellet was resuspended in 25 ml of cold 100 mM CaCl$_2$ and incubated on ice for 25 minutes. The cells were once again pelleted by centrifugation, and the pellet was resuspended in 2.5 ml of cold 100 mM CaCl$_2$ and incubated on ice overnight.

Two hundred μl of this cell suspension were mixed with the ligated DNA prepared above and incubated on ice for 20 minutes. At the end of this period, the cells were placed in a water bath at 42° C. for 2 minutes and then returned to the ice for an additional 10 minutes. The cells were collected by centrifugation and resuspended in one ml of L-broth and incubated at 37° C. for 2 hours.

Aliquots of the cell mixture were plated on L-agar (L-broth with 15 grams per liter agar) plates containing 100 µg ampicillin/ml, 40 µg X-gal/ml, and 40 µg IPTG/ml. The plates were incubated at 37° C. overnight. Colonies that contain a plasmid without an insert, such as E. coli K12 JM109/pUC8, appear blue on these plates. Colonies that contain a plasmid with an insert, such as E. coli K12 JM109/pPS23, are white. Several white colonies were selected and screened by restriction analysis of their plasmid DNA for the presence of the ~0.86 kb BamHI restriction fragment containing the IPS activating sequence. Plasmid DNA was obtained from the E. coli K12 JM109/pPS23 and E. coli K12 JM109/pPS23.1 cells in substantial accordance with the teaching of Example 2A.

B. Isolation of the ~0.86 kb BamHI Restriction Fragment of Plasmid pPS23

About 50 µg of plasmid pPS23 DNA were dissolved in 15 µl of 10X BamHI reaction buffer and 125 µl of H₂O. About 10 µl (100 units) of restriction enzyme BamHI were added to the solution of DNA, and the resulting reaction was incubated at 37° C. for two hours. The BamHI-digested plasmid pPS23 DNA was loaded onto a 1% agarose gel, and the ~0.86 kb BamHI restriction fragment that comprises the activating sequence of the IPS gene was isolated in substantial accordance with the procedure of Example 2B. About 5 µg of the desired fragment were obtained and suspended in 10 µl of H₂O.

Preparation of BamHI-Digested Plasmid pPS19 DNA

About 5 µg of plasmid pPS19 DNA were dissolved in 10 µl 10X BamHI reaction buffer and 35 µl of H₂O. About 5 µl (50 units) of restriction enzyme BamHI were added to the solution of plasmid pPS19 DNA, and the resulting reaction was incubated at 37° C. for two hours. The reaction mixture of BamHI-digested plasmid pPS19 DNA was extracted once with buffered phenol and then extracted twice with chlorofoam. The DNA was then precipitated, collected by centrifugation, and resuspended in 10 µl of H₂O.

D. Final Construction of Plasmids pPS21A, pPS22, pPS24, pPS25, and pPS25.1

About 1 µl of the ~0.86 kb BamHI restriction fragment of plasmid pPS23 was added to 1 µl of the BamHI-digested plasmid pPS19 DNA, 3 µl 10X ligase buffer, 2 µl T4 DNA ligase, and 23 µl of H₂O. The resulting ligation reaction was incubated at 15° C. overnight. The ligated DNA constituted the desired plasmids pPS21A, pPS22, pPS24, pPS25, and pPS25.1.

The ligated DNA was used to transform E. coli K12 C600, a strain available from the American Type Culture Collection, Rockville, Md. 20852, under the accession number ATCC 33525, in substantial accordance with the procedure of Example 7A(iv). The transformed cells were plated on L-agar plates containing 100 µg/ml ampicillin, and the plates were incubated at 37° C. overnight.

Individual colonies were picked from the transformation plates, cultured, and used to prepare plasmid DNA. The plasmid DNA was analyzed by restriction enzyme analysis. The following chart demonstrates the appropriate restriction enzyme digests that can be used to distinguish the plasmids.

| Plasmid | Enzyme | Size of Fragments (in kb) |
|---|---|---|
| pPS19 | BamHI | 7.62 and 0.23 |
|  | PstI | 5.15, 1.85, and 0.86 |
| pPS21A | BamHI | 7.62 and 0.86 |
|  | PstI | 5.15, 1.85, 0.99, and 0.49 |
| pPS22 | BamHI | 7.62 and 0.86 |
|  | PstI | 5.15, 1.85, 0.94, and 0.54 |
| pPS24 | BamHI | 7.62 |
|  | PstI | 7.62 |
| pPS25 and | PstI | 5.15, 1.85, 0.99, and 0.72 |
| pPS25.1 | BamHI | 7.62, 0.86, and 0.23 |

Figure 8:
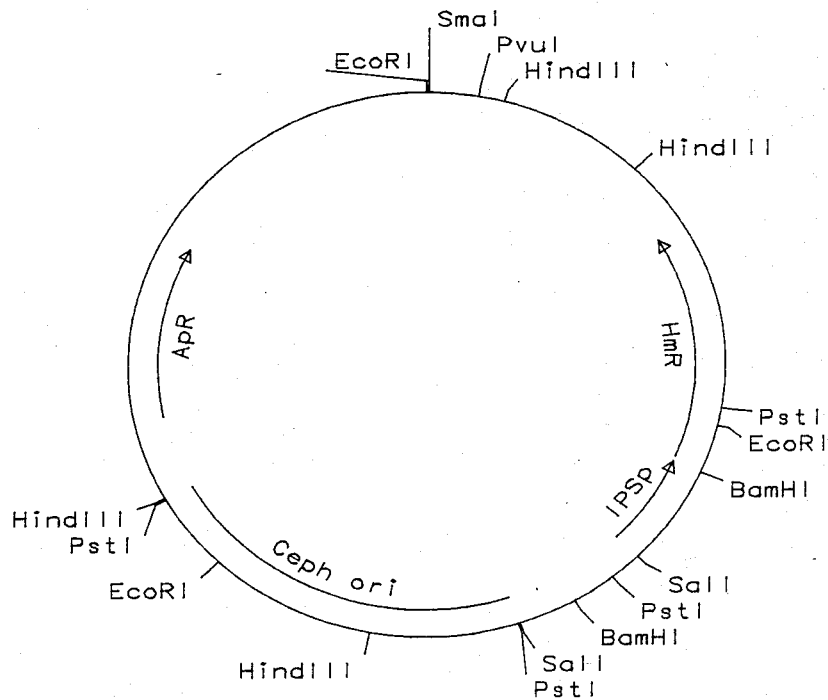
FIG. 8. A restriction site and function map of plasmid pPS21A.
Figure 9:
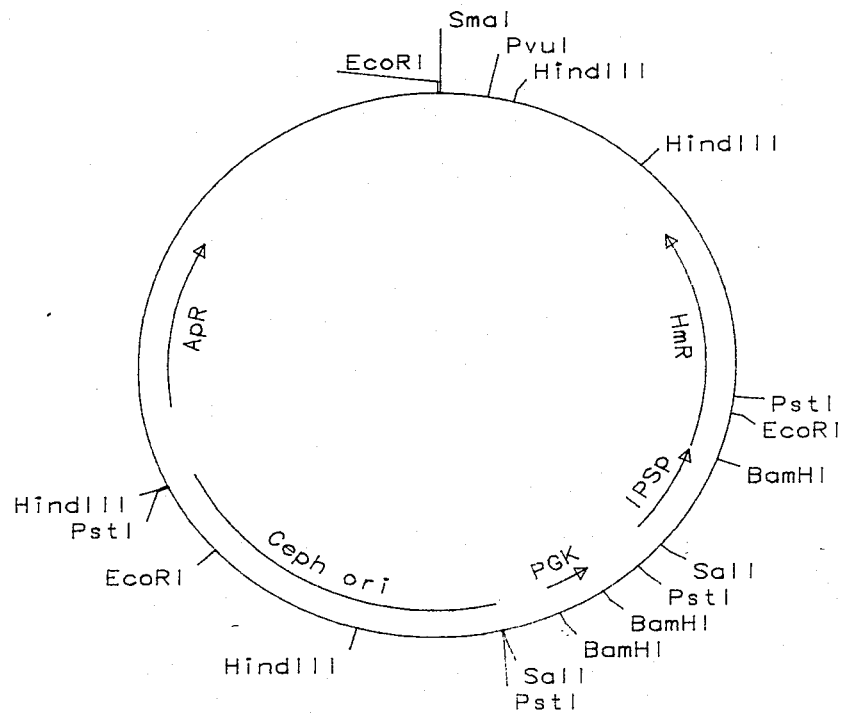
FIG. 9. A restriction site and function map of plasmid pPS25.

Restriction site and function maps of plasmids pPS21A and pPS25 are respectively presented in FIGS. 8 and 9 of the accompanying drawings.

Plasmids pPS21A, pPS25.1, and pPS25 were used to transform Cephalosporium acremonium in substantial accordance with the procedure of Examples 6 and 14. The C. acremonium/pPS21A, C. acremonium/pPS25.1, and C. acremonium/pPS25 transformants were hygromycin-resistant. Plasmids pPS22 and pPS24 were also used to transform C. acremonium, but these plasmids transformed C. acremonium to hygromycin resistance at a much lower frequency than did plasmids pPS21A, pPS25.1, and pPS25, presumably because plasmids pPS22 and pPS24 must integrate into the C. acremonium genome in the proper position for a genomic C. acremonium activating sequence to drive expression of the hygromycin resistance-conferring gene.

EXAMPLE 8

Construction of Plasmids pPS28 and pPS29

About 20 µl of plasmid pPS21A DNA were dissolved in 10 µl 10X PstI reaction buffer (1.0 M NaCl; 100 mM Tris-HCl, pH=7.5; 100 mM MgCl₂; and 1 mg/ml BSA) and 88 µl of H₂O. About 2 µl (150 units) of restriction enzyme PstI were added to the solution of DNA, and the reaction was incubated at 37° C. for 4 minutes, and then, the reaction was terminated by incubation at 70° C. for 10 minutes. The partially PstI-digested plasmid pPS21A DNA was loaded onto an agarose gel, and after electrophoresis and staining of the gel, the following fragments were observed: 8.5 kb (linearized plasmid); 8.0 kb; 7.5 kb; 7.0 kb; 6.6 kb; 6.1 kb; 5.2 kb; 3.3 kb; 2.3 kb; 1.9 kb; 1.5 kb; 1.0 kb; and 0.5 kb. The ~6.6 kb and ~6.1 kb PstI restriction fragments were individually isolated in substantial accordance with the procedure of Example 2B; about 0.5 µg of each fragment were recovered.

The ~6.6 kb PstI restriction fragment was dissolved in 3 µl 10X ligase buffer and 25 µl of H₂O. About 2 µl of T4 DNA ligase were added to the solution of DNA, and the resulting reaction was incubated at 15° C. plasmid pPS28 DNA, which was used to transform E. coli K12 C600 in substantial accordance with the procedure of Example 7. In a similar fashion, the ~6.1 kb PstI restriction fragment was circularized by ligation to yield plasmid pPS29, which was also transformed into E. coli K12 C600. Restriction site and function maps of plasmids pPS28 and pPS29 are respectively presented in FIGS. 10 and 11 of the accompanying drawings.

Plasmids pPS28 and pPS29 were used to transform Cephalosporium acremonium in substantial accordance with the procedure of Examples 6 and 14. The C. acremonium/pPS28 and C. acremonium/pPS29 transformants exhibited the hygromycin-resistant phenotype, and the plasmid pPS28 and plasmid pPS29 DNA transformed the *C. acremonium* to hygromycin resistance at high frequency.

EXAMPLE 9

Construction of Plasmids pPS26 and pPS26.1

About 20 µg of plasmid pPS21A were dissolved in 10 µl 10X HindIII reaction buffer and 85 µl of H₂O. About 5 µl (50 units) of restriction enzyme HindIII were added to the solution of DNA, and the resulting reaction was incubated at 37° C. for two hours. The HindIII-digested plasmid pPS21A DNA was loaded onto a 1% agarose gel and electrophoresed until the ~3.45 kb, ~3.16 kb, ~1.2 kb, and ~0.69 kb HindIII restriction fragments were clearly separated on the gel. The ~3.45 kb HindIII restriction fragment was isolated in substantial accordance with the procedure of Example 2B. About 5 µg, of the desired ~3.45 kb HindIII restriction fragment were obtained and suspended in 10 µl of H₂O.

About 2 µl of the ~3.45 kb HindIII restriction fragment of plasmid pPS21A were added to 1 µl of the HindIII-digested plasmid pIT335 prepared in Example 4A, 3 µl 10X ligase buffer, 22 µl of H₂O and 2 µl of T4 DNA ligase. The resulting ligation reaction was incubated at 15° C. overnight. The ligated DNA constituted the desired plasmids pPS26 and pPS26.1. The ligated DNA was used to transform *E. coli* K12 C600 in substantial accordance with the procedure of Example 7. The *E. coli* K12 C600/pPS26 and *E. coli* K12 C600/pPS26.1 transformants were identified by their ampicillin-resistant phenotype and by restriction enzyme analysis of their plasmid DNA. A restriction site and function map of plasmid pPS26 is presented in FIG. 12 of the accompanying drawings.

Plasmids pPS26 and pPS26.1 were used to transform *Cephalosporium acremonium* in substantial accordance with the procedure of Example 6. Plasmids pPS26 and pPS26.1 transformed *C. acremonium* to hygromycin resistance at high frequency, and the *C. acremonium*/pPS26 and *C. acremonium*/pPS26.1 transformants produced significantly more isopenicillin N, as measured by zones of inhibition of growth of *Micrococcus luteus*, than their untransformed counterparts.

EXAMPLE 10

Construction of Plasmids pPS30, pPS30.1, pPS31, and pPS31.1

Those skilled in the art recognize that *Cephalosporium acremonium* rRNA genes other than those encoded on the ~3.7 kb XmaI restriction fragment used in the construction of plasmids pPS30, pPS30.1, pPS31, and pPS31.1 can be incorporated onto the vectors of the present invention. Thus, the present invention comprises vectors that drive expression of IPS in *C. acremonium* and also contain one or more of the 18S, 5.8S, and 25S rRNA genes of *C. acremonium* for purposes of directing integration of the vector into the *C. acremonium* genome.

A. Isolation of the ~3.7 kb XmaI Restriction Fragment of Plasmid pPS6

Plasmid pPS6 is disclosed and claimed in Example 13, pages 72-75, of U.S. patent application No. 654,919, attorney docket number X-6570, filed 9-27-85, incorporated herein by reference. About 10 µg of plasmid pPS6 were dissolved in 20 µl 10X XmaI reaction buffer (250 mM NaCl; 100 mM Tris-HCl, pH=7.5; 100 mM MgCl₂; 100 mM 2-mercaptoethanol; and 1 mg/ml BSA) and 65 µl of H₂O. About 15 µl (30 units) of restriction enzyme XmaI were added to the solution of plasmid pPS6 DNA, and the resulting reaction was incubated at 37° C. for four hours.

The XmaI-digested plasmid pPS6 DNA was loaded onto a 1% agarose gel and electrophoresed until the ~3.7 kb XmaI restriction fragment was clearly separated from the other digestion product. The ~3.7 kb XmaI restriction fragment was then isolated in substantial accordance with the procedure of Example 2B. About 5 µg of the desired ~3.7 kb XmaI restriction fragment were obtained and suspended in 10 µl of H₂O.

B. Final Construction of Plasmids pPS30 and pPS30.1

About 1 µg of plasmid pPS21A NA was dissolved in 2 µl 10X XmaI reaction buffer and 6 µl of H₂O. About 2 µl (6 units) of restriction enzyme XmaI were added to the solution of plasmid pPS21A DNA, and the resulting reaction was incubated at 37° C. for four hours. The reaction was terminated by extraction with buffered phenol, followed by two extractions with chloroform. The reaction mixture was then precipitated, collected by centrifugation, and resuspended in 23 µl of H₂O.

About 2 µl of the ~3.7 kb XmaI restriction fragment of plasmid pPS6, 3 µl of 10X ligase buffer, and 2 µl of T4 DNA ligase were added to the solution of XmaI-digested plasmid pPS21A DNA, and the resulting ligation reaction was incubated at 15° C. overnight. The ligated DNA constituted the desired plasmids pPS30 and pPS30.1, which differ only with respect to the orientation of the ~3.7 kb XmaI restriction fragment.

The ligated DNA was used to transform *E. coli* K12 C600 in substantial accordance with the procedure of Example 7. The *E. coli* K12 C600/pPS30 and *E. coli* K12 C600/pPS30.1 transformants were identified by their ampicillin-resistant phenotype and by restriction enzyme analysis of their plasmid DNA.

Plasmids pPS30 and pPS30.1 were also used to transform Cephalosporium acremonium. The *C. acremonium*/pPS30 and *C. acremonium*/pPS30.1 transformants were resistant to hygromycin.

C. Final Construction of Plasmids pPS31 and pPS31.1

Plasmids pPS31 and pPS31.1 were constructed and then transformed into *E. coli* K12 C600 and *Cephalosporium acremonium* in substantial accordance with the procedure of Example 10B, with the exception that plasmid pPS29, rather than plasmid pPS21A, was used as starting material in the construction.

EXAMPLE 11

Construction of Plasmid pPS27

A. Construction of Plasmid pIT336

About 1 µg of plasmid pUC8 was dissolved in 2 µl 10X BamHI reaction buffer and 16 µl of H₂O. About 2 µl (20 units) of restriction enzyme BamHI were added to the solution of plasmid pUC8 DNA, and the resulting reaction was incubated at 37° C. for two hours. The BamHI-digested plasmid pUC8 DNA was precipitated, collected by centrifugation, and resuspended in 2 µl 10X SalI reaction buffer (1.5 M NaCl; 60 mM Tris-HCl, pH=7.9; 60 mM MgCl₂; 60 mM 2-mercaptoethanol; and 1 mg/ml BSA) and 16 µl of H₂O. About 2 µl (20 units) of restriction enzyme SalI were added to the solution of BamHI-digested plasmid pUC8 DNA, and the resulting reaction was incubated at 37° C. for two hours. The reaction was terminated by extraction with phenol, followed by two extractions with chloroform. The SalI-BamHI-digested plasmid pUC8 DNA was precipitated, collected by centrifugation, and resuspended in 5 μl of H₂O.

About 10 μg of plasmid pIT335 were dissolved in 10 μl 10X BamHI reaction buffer and 80 μl of H₂O. About 5 μl (50 units) each of restriction enzymes XhoI and BamHI were added to the solution of plasmid pIT335 DNA, and the resulting reaction was incubated at 37° C. for two hours. The reaction mixture was then loaded onto a 1% agarose gel and electrophoresed until the ~1.4 kb BamHI-XhoI restriction fragment was separated from the other reaction products, which were 5.6 kb, 1.3 kb, and 0.01 kb fragments. The ~1.4 kb BamHI-XhoI restriction fragment, which comprises the transcription termination and mRNA polyadenylation and processing signals of the IPS gene, was isolated in substantial accordance with the procedure of Example 2B. About 2 μg of the desired fragment were obtained and suspended in 5 μl of H₂O.

The 5 μl of SalI-BamHI digested plasmid pUC8 were added to 2 μl of the ~1.4 kb BamHI-XhoI restriction fragment of plasmid pIT335, 3 μl 10X ligase buffer 18 μl of H₂O, and 2 μl of T4 DNA ligase. The resulting reaction was incubated at 15° C. overnight. SalI and XhoI overlaps are compatible for ligation, but once ligated, neither SalI nor XhoI will cleave the DNA at the junction. The ligated DNA constituted the desired plasmid pIT336 and was used to transform *E. coli* K12 RR1ΔM15, available from the NRRL under the accession number NRRL B-15440, in substantial accordance with the procedure of Example 7A(iv). The transformed cells were plated on L-agar plates containing 100 μg/ml ampicillin, 40 μg/ml X-gal, and 40 μg/ml IPTG. Colonies that failed to exhibit the blue color on the transformation plates were cultured, used to prepare plasmid DNA, and the plasmid DNA was analyzed by restriction enzyme analysis to identify the *E. coli* K12 RR1ΔM15/pIT336 transformants. A restriction site and function map of plasmid pIT336 is presented in FIG. 14 of the accompanying drawings.

B. Construction of Plasmid pPS35

About 2 μg of plasmid pIT336 were dissolved in 2 μl 10X PstI reaction buffer and 17 μl of H₂O. About 1 μl (10 units) of restriction enzyme PstI was added to the solution of pIT336 DNA, and the resulting reaction was incubated at 37° C. for 2 hours. The reaction was terminated by extraction with phenol, followed by two extractions with chloroform. The PstI-digested plasmid pIT336 DNA was then precipitated, collected by centrifugation, and resuspended in 86 μl of H₂O.

About 10 μl of 10X ligase buffer and 4 μl of T4 DNA ligase were added to the solution of PstIdigested plasmid pIT336 DNA, and the resulting reaction was incubated at 15° C. overnight. The ligated DNA constituted the desired plasmid pPS35 and was used to transform *E. coli* K12 JA221, available from the NRRL under the accession number NRRL B-15211, in substantial accordance with the procedure of Example 7A(iv). The transformed cells were plated on L-agar plates containing 100 μg/ml ampicillin. Several ampicillin resistant colonies were isolated and used to prepare plasmid DNA. The desired *E. coli* K12 JA221/pPS35 transformants were identified by restriction enzyme analysis of their plasmid DNA. A restriction site and function map of plasmid pPS35 is presented in FIG. 15 of the accompanying drawings.

C. Final Construction of Plasmid pPS27

About 2 μg of plasmid pPS35 were dissolved in 2 μl 10X HindIII reaction buffer and 17 μl of H₂O. About 1 μl (10 units) of restriction enzyme HindIII was added to the solution of plasmid pPS35 DNA, and the resulting reaction was incubated at 37° C. for two hours. The reaction was terminated by extraction with phenol, followed by two extractions with chloroform. The HindIII-digested plasmid pPS35 DNA was then precipitated, collected by centrifugation, and resuspended in 3 μl 10X ligase buffer and 23 μl of H₂O.

About 2 μl of the ~2.3 kb HindIII restriction fragment ff plasmid pPS29, which was prepared and isolated in substantial accordance with the procedure of Example 9 using plasmid pPS29 as starting material instead of plasmid pPS21A and which comprises the hygromycin resistance-conferring gene driven by the activating sequence of the IPS gene, and 2 μl of T4 DNA ligase were added to the solution of HindIII-digested plasmid pPS35 DNA. The resulting ligation reaction was incubated at 15° C. overnight. The ligated DNA constituted the desired plasmid pPS27 and was used to transform *E. coli* K12 JA221 in substantial accordance with the procedure of Example 11B.

The ampicillin-resistant transformants were cultured and used to prepare plasmid DNA, which was analyzed by restriction enzyme analysis to identify the desired *E. coli* K12 JA221/pPS27 transformants. Only one orientation of the inserted ~3.45 kb HindIII restriction fragment produces the desired plasmid pPS27. A restriction site and function map of plasmid pPS27 is presented in FIG. 12 of the accompanying drawings.

Plasmid pPS27 transforms *Cephalosporium acremonium* to a hygromycin-resistant phenotype at high frequency. *C. acremonium*/pPS27 transformants are prepared in substantial accordance with the procedure of Example 6.

EXAMPLE 12

Construction of Plasmid pPS47

A. Construction of Intermediate Plasmid pPS48

Figure 18:
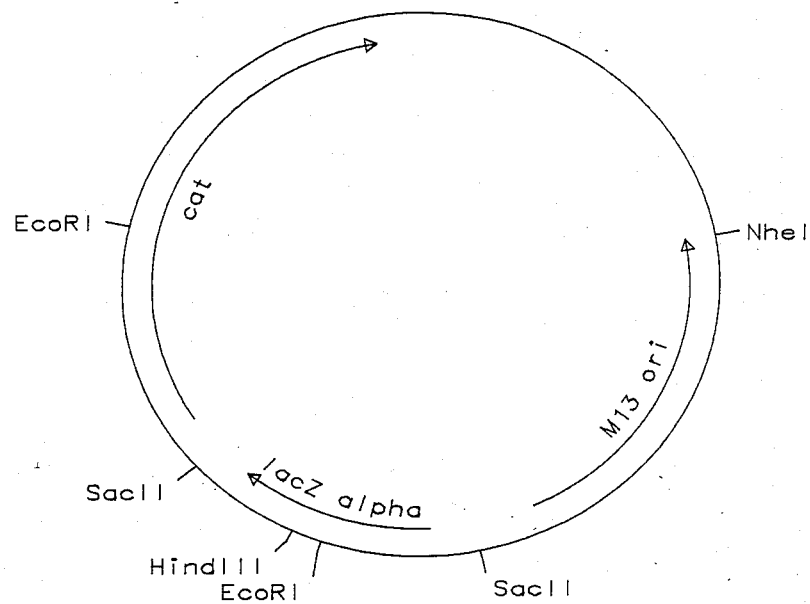
FIG. 18. A restriction site and function map of plasmid pMLC12.

Plasmid pMLC12 is an *E. coli* vector that encodes the lacZ α fragment and a chloramphenicol resistance-conferring gene. Plasmid pMLC12 also encodes two EcoRI restriction enzyme recognition sites, one on the lacZ α fragment-encoding DNA and the other in the chloramphenicol resistance-conferring gene. A restriction site and function map of plasmid pMLC12 is presented in FIG. 18 of the accompanying drawings. Plasmid pMLC12 is available from the Northern Regional Research Center under the accession number NRRL B-18097. Plasmid pMLC12 can be obtained from the deposited culture in substantial accordance with the procedure of Example 1, except that the cells are cultured in media containing chloramphenicol, rather than ampicillin, at 100 μg/ml.

About 10 μg of plasmid pMCL12 in 10 μl of TE buffer were dissolved in 2 μl of 10X EcoRI buffer (1.0 M Tris-HCl, pH=7.5; 0.5 M NaCl; 50 mM MgCl₂; and 1 mg/ml BSA) and 6 μl of H₂O. About 2 μl (~50 units) of restriction enzyme EcoRI were added to the solution of plasmid pMLC12 DNA, and the resulting reaction was incubated at 37° C. for 3 minutes. The short reaction time was designed to yield a partial EcoRI digestion. The partially-EcoRI-digested plasmid pMLC12 DNA was extracted twice with an equal volume of TE buffer-saturated phenol to stop the digestion; two chloroform extractions were then performed on the mixture to remove the phenol. About one-tenth volume of 3.0 M sodium acetate (NaOAc) and two volumes of ethanol were added to the mixture, which was incubated at −70° C. for 15 minutes and then centrifuged to pellet the DNA.

About 30 μg of plasmid pPS34 DNA in 30 μl of TE buffer were added to 10 μl of 10X EcoRI buffer and 55 μl of H₂O. About 5 μl (~100 units) of restriction enzyme EcoRI were added to the solution of plasmid pPS34 DNA, and the resulting reaction was incubated at 37° C. for 2 hours. The reaction was stopped by extraction with phenol as described above; then, the mixture was extracted with chloroform and precipitated, also as described above. The EcoRI-digested plasmid pPS34 DNA was loaded onto an agarose gel and electrophoresed to separate the ~4.3 kb restriction fragment from the ~3.4 kb restriction fragment. The ~4.3 kb fragment, which contains an intact copy of the IPS gene of *Cephalosporium acremonium*, was purified from the gel in substantial accordance with the procedure of Example 2B. About 5 μg of the desired fragment were obtained.

Figure 19:
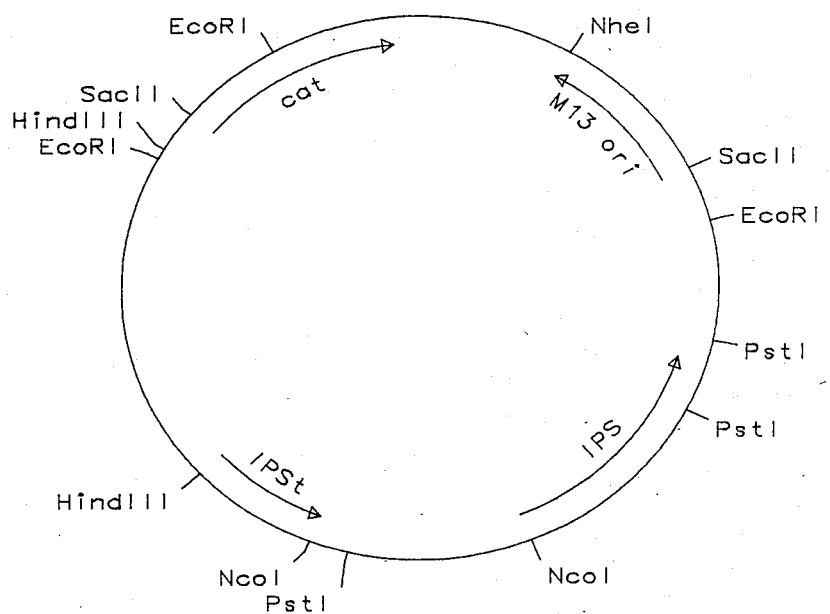
FIG. 19. A restriction site and function map of plasmid pPS48.

About 0.2 μg of the partially-EcoRI-digested plasmid pMLC12 DNA were added to ~0.3 μg of the ~4.3 kb EcoRI restriction fragment of plasmid pPS34. The DNA was pelleted with NaOAc and ethanol and then resuspended in 20 μl of lX ligase buffer containing 1 unit (Boehringer-Mannheim) of T4 DNA ligase. The reaction mixture was incubated overnight at 15° C. and constituted the desired plasmids pPS48 and pPS48.1. Plasmid pPS48 results from the insertion of the ~4.3 kb EcoRI restriction fragment of plasmid pPS34 into the EcoRI restriction enzyme recognition sequence in the lacZ α fragment-encoding DNA of plasmid pMLC12. Plasmid pPS48.1 differs from plasmid pPS48 only with respect to the orientation of the ~4.3 kb fragment. A restriction site and function map of plasmid pPS48 is presented in FIG. 19 of the accompanying drawings.

The ligated DNA was used to transform *E. coli* K12 JM109 in substantial accordance with the procedure of Example 7(a)(IV). The transformed cells were plated on L agar containing 1 mM IPTG, 20 μg/ml x-Gal, and 100 μg/ml chloramphenicol. A number of colorless, chloramphenicol-resistant colonies were selected and used to prepare plasmid DNA, which was subjected to restriction enzyme analysis to identify those transformants that contained plasmid pPS48 or plasmid pPS48.1. Plasmid pPS48 DNA was isolated from the *E. coli* K12 JM109/pPS48 transformants in substantial accordance with the procedure of Example 1, except that selection was based on chloramphenicol, not ampicillin, resistance, and there was no amplification of plasmid DNA.

B. Final Construction of Plasmid pPS47

About 20 μg of plasmid pPS29 DNA in 20 μl of TE buffer were added to 10 μl of 10X HindIII buffer and 65 μl of H₂O. About 5 μl (~50 units) of restriction enzyme HindIII were added to the solution of plasmid pPS29 DNA, and the resulting reaction was incubated at 37° C. for 2 hours. The reaction was stopped by extracting the reaction mixture with TE-saturated phenol; then, the reaction mixture was extracted twice with chloroform and the DNA pelleted by precipitation with NaOAc and ethanol followed by centrifugation. The HindIII-digested plasmid pPS29 DNA was loaded onto an agarose gel and electrophoresed to separate the ~2.3 kb fragment from the 3.0 kb and 0.69 kb fragments. The ~2.3 kb fragment, which contains the hygromycin B resistance-conferring gene fused to the promoter of the IPS gene, was purified from the gel in substantial accordance with the procedure of Example 2B. About 3 μg of the 2.3 kb fragment were recovered.

About 10 μg of plasmid pPS48 DNA in 10 μl of TE buffer were added to 5 μl of 10X HindIII buffer and 30 μl of H₂O. About 5 μl (~50 units) of restriction enzyme HindIII were added to the solution of plasmid pPS48 DNA, and the resulting reaction was incubated at 37° C. for 2 hours. The reaction was stopped and the DNA pelleted as described above. The HindIII-digested plasmid pPS48 DNA was loaded onto an agarose gel and electrophoresed to separate the ~5.6 kb restriction fragment from the ~1.4 kb fragment. The ~5.6 kb fragment was purified from the gel in substantial accordance with the procedure of Example 2B. About 5 μg of the desired ~5.6 kb fragment were obtained.

About 0.5 μg of the ~2.3 kb HindIII restriction fragment of plasmid pPS29 were mixed with ~0.5 μg of the ~5.6 kb HindIII restriction fragment of plasmid pPS48, and the DNA was pelleted from the solution by precipitation with NaOAc and ethanol followed by centrifugation. The DNA pellet was resuspended in 20 μl of 1X T4 DNA ligase buffer containing 1 unit (Boehringer Mannheim) of T4 DNA ligase. The ligation reaction mixture was incubated at 15° C. overnight. The ligated DNA constituted the desired plasmid pPS47 and another plasmid, designated pPS47.1, that differs from plasmid pPS47 with respect to the orientation of the 2.3 kb HindIII restriction fragment and therefore does not confer hygromycin resistance. A restriction site and function map of plasmid pPS47 is presented in FIG. 20 of the accompanying drawings.

The ligated DNA was used to transform *E. coli* K12 C600 in substantial accordance with the procedure of Example 7(a)(iv). The transformed cells were plated on L agar containing 100 μg/ml chloramphenicol, and the plasmid DNA of the chloramphenicol resistant transformants was subjected to restriction enzyme analysis to identify the desired *E. coli* K12 C600/pPS47 and *E. coli* K12 C600/pPS47.1 transformants.

Plasmids pPS47 and pPS47.1 were prepared from their respective transformants in substantial accordance with the procedure of Example 1, although chloramphenicol, not ampicillin, resistance was the basis for selection. Plasmid pPS47 was used to transform *Cephalosporium acremonium*, in substantial accordance with the procedure of Example 14. The *C. acremonium*/pPS47 transformants were hygromycin-resistant and produced more cephalosporin C than their untransformed counterparts. Use of plasmid pPS47 eliminates the possibility of expressinq a plasmid-borne β-lactamase gene in *C. acremonium*, for plasmid pPS47 does not contain a α-lactamase gene.

EXAMPLE 13

Construction of Mutant Isopenicillin N Synthetase Genes

A. Construction of Phage mIT110

About 50 μg of plasmid pIT335 DNA in 50 μl of TE buffer were added to 25 μl of 10X BamHI buffer and 170 μl of H₂O. About 5 μl (~50 units) of restriction enzyme BamHI were added to the solution of plasmid pIT335 DNA, and the resulting reaction was incubated at 37° C. for 2 hours. The reaction was stopped by extracting the reaction mixture with TE-saturated phenol; the phenol was removed by chloroform extractions. The BamHI-digested plasmid pIT335 DNA was then collected by precipitation and centrifugation, loaded onto a 6% acrylamide gel, and electrophoresed to isolate the ~2.67 kb BamHI restriction fragment. After electrophoresis, the gel was stained, and the fragment of the gel containing the ~2.67 kb BamHI restriction fragment was cut away from the remainder of the gel. This acrylamide fragment was subjected to further electroelution such that the DNA contained in the fragment was electroeluted into dialysis tubing. The solution of DNA was removed from the dialysis tubing, extracted with TE-saturated phenol, extracted with chloroform, extracted with isopropanol, precipitated, and collected by centrifugation. About 5 µg of the ~2.67 kb BamH restriction fragment of plasmid pIT335 were obtained and dissolved in 10 µl of TE buffer.

About 5 µg of phage m13mp19 (obtained from New England Biolabs, 32 Tozer Road, Beverly, Mass.) were dissolved in 20 µl of 1X BamHI buffer containing ~20 units of restriction enzyme BamHI, and the resulting reaction was incubated at 37° C. for 2 hours. The reaction mixture was extracted with phenol and then chloroform; then, the DNA was precipitated, collected by centrifugation, and resuspended in about 7 µl of TE buffer.

Figure 21:
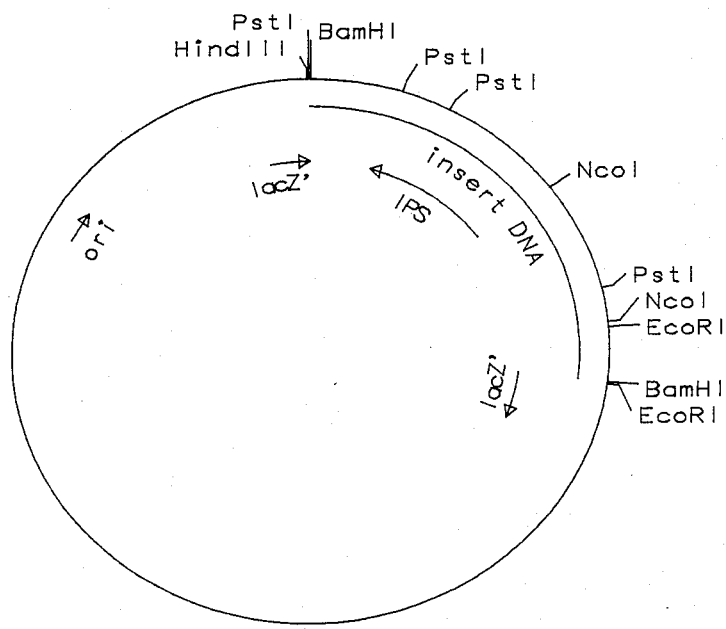
FIG. 21. A restriction site and function map of phage mIT110.

About 2 µl of the ~2.67 kb BamHI restriction fragment of plasmid pIT335 were added to 1 µl of the BamHI-digested m13mp19 DNA together with 2 µl of 10X ligase buffer, 1 µl (~100 units) of T4 DNA ligase, and 14 µl of H2O. The ligation reaction was incubated at 15° C. for 1.5 hours; the ligated DNA constituted the desired phage mIT110 DNA. A restriction site and function map of phage mIT110 is presented in FIG. 21 of the accompanying drawings.

One ml of an overnight culture of *E. coli* K12 JM103 (*E. coli* K12 JM101, available from New England Biolabs, can be used in place of *E. coli* K12 JM103) was used to inoculate 50 ml of L broth, and the resulting culture was incubated at 37° C. with aeration until the O.D.$_{660}$ was between 0.3 and 0.4. The cells were resuspended in 25 ml of 10 mM NaCl, incubated on ice for 10 minutes, and collected by centrifugation. The cells were resuspended in 1.25 ml of 75 mM CaCl$_2$; a 200 µl aliquot of the cells was removed, added to 10 µl of the ligated DNA prepared above, and incubated on ice for about 40 minutes. The cell-DNA mixture was then incubated at 42° C. for 2 minutes, and varying aliquots (1, 10, and 100 µl) were removed and added to 3 ml of top agar (L broth with 0.5% agar kept molten at 45° C.) that also contained 50 µl of 2% X-Gal, 50 µl of 100 mM IPTG, and 200 µl of *E. coli* K12 JM103 in logarithmic growth phase. The cell-top agar mixture was then plated on L-agar plates containing 40 µg/ml X-Gal and 0.1 mM IPTG, and the plates were incubated at 37° C. overnight.

The following morning, several clear plaques were individually used to inoculate 2 ml of L broth, and the resulting cultures were incubated at 37° C. with aeration for 2 hours. Then, the cultures were centrifuged, and 200 µl of the resulting supernatant were added to 10 ml cultures (O.D.$_{550}$=0.5) of *E. coli* K12 JM103 growing at 37° C. with aeration. These cultures were incubated for another 30 minutes at 37° C.; then, the cells were pelleted by centrifugation and used to prepare the replicative-form of the recombinant phage they contained. The phage were isolated from the cells using a scaled-down version of the procedure described in Example 1. Transformants containing phage mIT110 DNA were identified by restriction enzyme analysis of their phage DNA.

B. Preparation of Single-Stranded Phage mIT110 DNA

One and one-half ml of an overnight culture of *E. coli* K12 JM103/mIT110 were centrifuged, and 100 µl of the phage mIT110-containing supernatant were used to inoculate a 25 ml culture of *E. coli* JM103 at an O.D.$_{660}$ of about 0.4–0.5. The culture was incubated for 6 hours at 37° C. with aeration, at which time the culture was centrifuged and the resulting supernatant, about 20 ml, transferred to a new tube. About 2 ml of a solution composed of 20% polyethylene glycol and 14.6% NaCl were added to the supernatant, which was then incubated on ice for 20 minutes.

The supernatant was centrifuged for 25 minutes at 7000 r.p.m., and the resulting pellet, which contained single-stranded phage mIT110 DNA, was resuspended in 500 µl of TE buffer. The DNA solution was extracted twice with TE-saturated phenol and twice with chloroform. form. The single-stranded DNA was then precipitated using NaOAc and ethanol and centrifuged, and, after the pellet was washed with 70% ethanol and dried, the pellet was dissolved in 60 µl of H$_2$O.

C. Mutagenesis

The single-stranded DNA fragments used in the mutagenesis were synthesized on an automated DNA synthesizer and will be referred to in this Example by IPS number, either "IPS8" or "IPS9":

IPS8 is a single-stranded DNA 36 nucleotides long that is homologous to the IPS coding sequence on mIT110 except for one base, the mismatch of which will create a serine codon in place of the cysteine codon that encodes the cysteine residue at position 106 in the IPS amino-acid residue sequence. IPS8 has the sequence:

SER 106
5'-AGGCGGTCGAATCGTTCTCCTACCTGAACCCCTCCT—3'

IPS9 is a single-stranded DNA 36 nucleotides long that is homologous to the IPS coding sequence on mIT110 except for one base, the mismatch of which will create a serine codon in place of the cysteine codon that encodes the cysteine residue at position 255 in the IPS amino-acid residue sequence. IPS9 has the sequence:

SER 255
5'-CGGGCTTCCTCATCAACTCCGGCAGCTACATGGCCC—3'
HpaII

About 10 picomoles each of IPS8, IPS9, and the M13 universal primer (marketed by Bethesda Research Laboratories (BRL), P.O. Box 6009, Gaithersburg, Md. were individually treated with 10 units (BRL) of T4 polynucleotide kinase in 20 μl of 1X kinase buffer (60 mM Tris-HCl, pH=7.8; 15 mM 2-mercaptoethanol; 10 mM MgCl$_2$; and 0.41 μM ATP) for 30 minutes at 37° C. The kinase-treated DNAs were used in the mutagenesis procedure described below.

The annealing reaction was carried out by adding 300 nanograms (1.2 μl) of single-stranded phage mIT110 to 1 picomole (2 μl) of the universal primer, 1 picomole (2 μl) of either IPS8 or IPS9, 2 μl of 10X annealing buffer (100 mM Tris-HCl, pH=7.5; 1 mM EDTA; and 500 mM NaCl), and 12.8 μl of H$_2$O, incubating the mixture at 80° C. for 2 minutes and then at 50° C. for 5 minutes, and, finally, allowing the mixture to cool to room temperature.

The extension reaction was carried out by adding 5 μl of 10X extension buffer (500 mM Tris-HCl, pH=8; 1 mM EDTA; and 120 mM MgCl2); 5 μl of 2 mM dATP; 1 μl of a solution 6 mM in each of dGTP, dTTP, and dCTP; 1 μl (~2 units, Pharmacia P-L Biochemicals) of Klenow enzyme; 1 μl (100 units) of T4 DNA ligase; and 17 μl of H$_2$O to the mixture of annealed DNA. The extension reaction was incubated at room temperature for 1 hour, then at 37° C. for 2.5 hours, and then overnight at 4° C.

The reaction was stopped by two extractions with TE-saturated phenol, which were followed by two chloroform extractions and precipitation of the DNA with ethanol and NaOAc. The DNA was collected by centrifugation and resuspended in 50 μl of H$_2$O, and 6 μl of 10X S1 buffer (0.3 M NaCl and 30 mM ZnOAc) were then added to the solution of DNA.

The solution of DNA was split equally into three tubes, and to two of the tubes, 200 units (Miles Laboratories) of S1 nuclease were added. One S1 reaction was incubated at room temperature for 5 minutes, and the other was incubated at room temperature for 10 minutes. The reactions were stopped by twice extracting the reaction mixture with TE-saturated phenol. The phenol extractions were followed by two extractions with chloroform; then, the DNA was precipitated from the reaction mixture with NaOAc and ethanol. The sample of DNA that was not treated with S1 nuclease (actually, two samples: one from the mutagenesis with IPS8 and the other from the mutagenesis with IPS9) served as a negative control. The samples treated with S1 nuclease for 5 minutes were kept separate from the samples treated with S1 for 10 minutes throughout the remainder of the procedure; however, the two samples gave similar results.

The DNA pellets were resuspended in 20 μl of H$_2$O, and 10 μl of the resulting solution were used to transform E. coli K12 JM109 (E. coli K12 JM101 could also be used) in accordance with the procedure used during the construction of phage mIT110, except that no IPTG or X-Gal was added to the plates. At least 20 plaques from each mutagenesis (one with IPS8; the other with IPS9) were picked from the plates, pooled (only with other plaques from the same mutagenesis), into 3 ml of L broth, and incubated with aeration at 37° C. for 4 hours. The cultures were then rplated, and after an overnight incubation at 37° C., 24 plaques from each mutagenesis were picked and individually inoculated into 2 ml of a culture of E. coli K12 JM109 in logarithmic growth phase. These cultures were incubated at 37° C. with aeration for about 6 hours, when they were then used to prepare single-stranded DNA as described above for phage mIT110.

The single-stranded DNA was sequenced using the dideoxy sequencing method (J. H. Smith, 1980, Methods in Enzymology 65:560-580), but only the C (cytidyl) sequencing reaction was performed and examined by electrophoresis, for a comparison of the C sequence of each of the 48 screened phage with that of phage mIT110 identifies those phage that have been mutagenized in the desired manner. Several phage were identified with the desired mutations. Phage in which the cysteine codon for residue 106 was changed to a serine codon were designated phage mIT111, while phage in which the cysteine codon for residue 255 was changed to a serine codon were designated mIT112. The mutation in phage mIT112 creates a new HpaII site not present in mIT110 that can be used to facilitate identification of phage mIT112.

D. Construction of Expression Vectors

Figure 22:
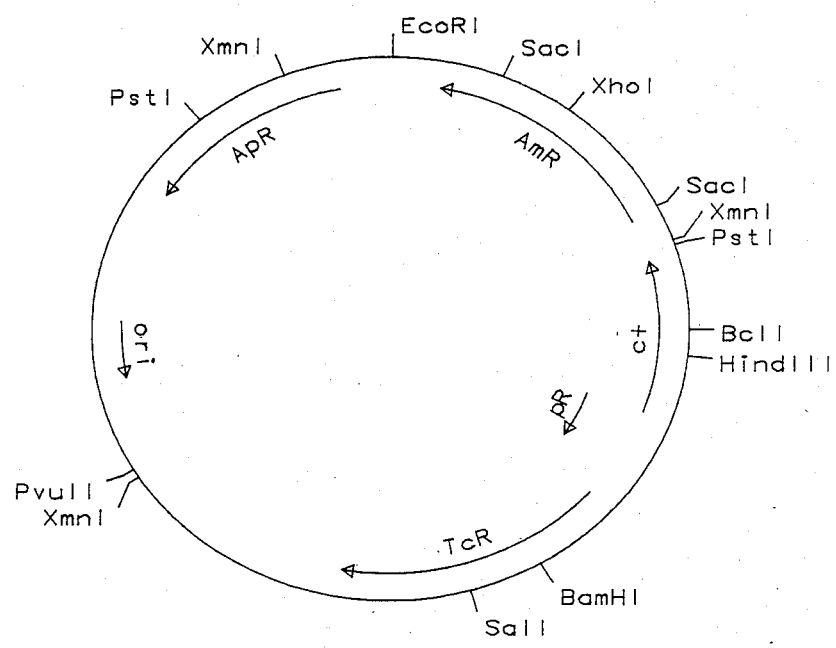
FIG. 22. A restriction site and function map of plasmid pKC309.

Plasmid pIT344WT is a useful expression vector that drives expression of IPS in E. coli. Plasmid pIT344WT was constructed from two plasmids, plasmid pKC309 and plasmid pIT337. Plasmid pKC309 is available from the Northern Regional Research Center under the accession number NRRL B-15827. A restriction site and function map of plasmid pKC309 is presented in FIG. 22 of the resistance to E. coli; apramycin is added to the media at a concentration of 100 μg/ml to select for a plasmid containing the apramycin resistance-conferring gene of plasmid pKC309.

The ~1.6 kb XmnI restriction fragment of plasmid pKC309 contains the intact apramycin resistance-conferring gene. Plasmid pKC309 was digested with restriction enzyme XmnI, and the ~1.6 kb XmnI fragment was isolated from the other fragments, about 1.8 kb and 3.5 kb in size, generated by the digestion. Plasmid pIT337 is ~11.8 kb in size, and BstEII and KpnI digestion of plasmid pCZ106 yields three fragments, one ~7.7 kb, one ~0.9 kb, and the other ~3.2 kb in size. The ~7.7 kb BstEII-KpnI restriction fragment of plasmid pIT337 comprises the trp transcription and translation activating sequence, the runaway replicon, and the IPS coding sequence. This ~7.7 kb BstEII-KpnI restriction fragment was isolated and treated first with T4 DNA polymerase in the absence of nucleotides to remove the 3' KpnI overlap and then with T4 DNA polymerase in the presence of nucleotides to generate a blunt-ended molecule that will ligate with the ~1.6 kb XmnI restriction fragment of plasmid pKC309 to yield plasmids pIT344WT and pIT344.1WT.

Figure 23:
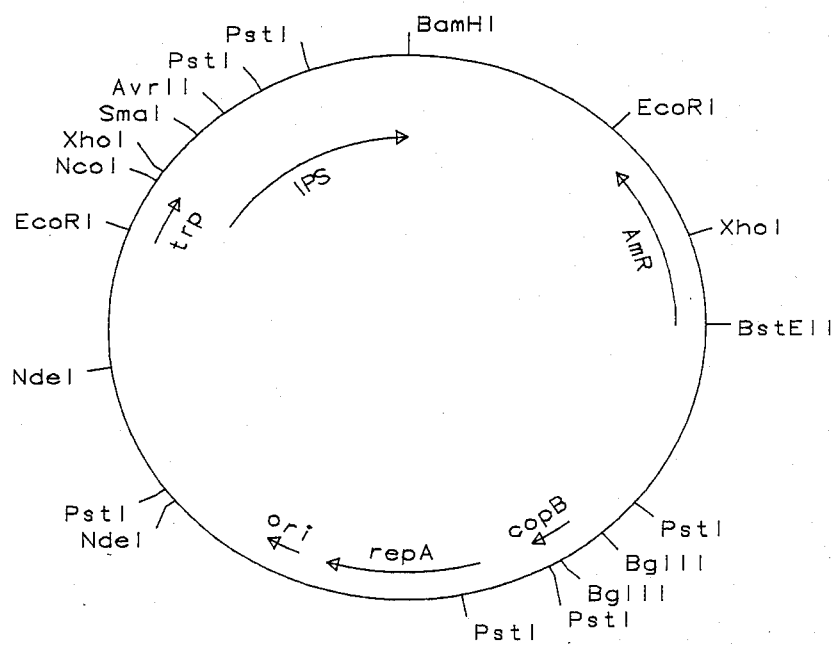
FIG. 23. A restriction site and function map of plasmid pIT344WT.

Thus, plasmid pIT344WT was constructed by ligating the ~1.6 kb, apramycin resistance-conferring XmnI restriction fragment of plasmid pKC309 to the ~7.7 kb, T4 DNA polymerase-treated BstEII-KpnI restriction fragment of plasmid pIT337. A restriction site and function map of plasmid pIT344WT is presented in FIG. 23 of the accompanying drawings.

Plasmid pIT344WT was digested with restriction enzymes NcoI and BamHI, and the ~7.8 kb NcoI-BamHI restriction fragment that comprises the trp promoter the runaway replicon, and the apramycin resistance conferring gene was isolated and prepared for ligation. Likewise, phages mIT111 and mIT112 were digested with restriction enzymes NcoI and BamHI, and the ~1.47 kb NcoI-BamHI restriction fragment that encodes the mutant IPS was isolated from each phage and prepared for ligation.

The ~1.47 kb NcoI-BamHI restriction fragment of phage mIT111 was ligated to the ~7.8 kb NcoI-BamHI restriction fragment of plasmid pIT344WT to construct plasmid pIT347. Plasmid pIT347 drives expression in *E. coli* of a mutant IPS enzyme that has a serine residue in place of a cysteine residue at position 106. Likewise, the ~1.47 kb NcoI-BamHI restriction fragment of phage mIT112 was ligated to the ~7.8 kb NcoI-BamHI restriction fragment of plasmid pIT344WT to construct plasmid pIT349. Plasmid pIT349 drives expression in *E coli* of a mutant IPS enzyme that has a serine residue in place of a cysteine residue at position 255.

Plasmids pIT347 and pIT349 were used to transform *E. coli* K12 RV308, and plasmid DNA from the transformants was isolated and used as starting material in the construction of plasmid pIT352. Plasmid pIT352 is analogous to plasmids pIT347 and pIT349, except plasmid pIT352 encodes a mutant IPS enzyme in which both the cysteine codons for residues 106 and 255 have been changed to serine codons. Plasmid pIT352 was constructed by isolating the ~975 bp AvrII-BamHI restriction fragment, which comprises that portion of the mutant IPS coding sequence that encodes residue 255, of plasmid pIT349 and ligating that fragment to the ~8.3 kb AvrII-BamHI restriction fragment, which comprises that portion of the mutant IPS coding sequence that encodes residue 106, of plasmid pIT347.

E. Expression and Activity of Mutant IPS Enzymes

Plasmids pIT347, pIT349, and pIT352 were transformed into *E. coli* K12 RV308 and *E. coli* K12 A85892. The resulting transformants were cultured and used to prepare cell-free extracts for determination of IPS activity. The control vector used in the assay was plasmid pIT344WT. Plasmid pIT344WT therefore drives expression of wild-type, or unmutated, isopenicillin N synthetase in *E. coli*.

The procedure set forth below is for one culture; however, each of the following cell lines were cultured and examined for IPS activity:
*E. coli* K12 RV308/pIT344WT
*E. coli* K12 RV308/pIT347
*E. coli* K12 RV308/pIT349
*E. coli* K12 RV308/pIT352
*E. coli* K12 A85892/pIT344WT
*E. coli* K12 A85892/pIT347
*E. coli* K12 A85892/pIT349
*E. coli* K12 A85892/pIT352

A sample of each culture was inoculated into 50 ml of L broth containing 100 μg/ml of apramycin and incubated at room temperature with aeration for about 16 hours. About 20 ml of the 50 ml culture were used to inoculate 1 liter of L broth containing 100 μg/ml apramycin and this culture was incubated at 37° C. for about 7 hours. The cells were collected by centrifugation and washed with 20 ml of 10 mM NaCl.

The cells were resuspended in buffer A+ (50 nM Tris-HCl, pH=8; 10 nM KCl; and 0.1% Triton X-100) using 10 ml of A+ buffer per gram of cells. Ten ml of the resuspended cells were placed in a tube to which was added: 10 μl of 1 M DTT; 50 μl of 0.2 M PMSF; and 500 μl of a solution containing 20 mg/ml lysozyme. The cells were then stirred on ice for about 30 minutes, at which time another 50 μl of 0.2 M PMSF were added. The solution of cells was then sonicated using there 20-second bursts of sonication. The solution was then centrifuged at 20,000 r.p.m. for 30 minutes at 4° C. Ten ml of the supernatant were collected and added to 10 μl of 1 M DTT and 50 μl of 0.2 M PMSF. Then 2.91 g of ammonium sulfate were slowly added and mixed into the solution, which was stirred on ice for about 30 minutes.

The solution was centrifuged at 20,000 r.p.m. for 20 minutes at 4° C. Once again, 10 ml of the supernatant were removed and added to 10 μl of 1 M DTT and 50 μl of 0.2 M PMSF. About 2.3 g of ammonium sulfate were slowly added and mixed into the solution, which was stirred on ice for about 30 minutes. The solution was then centrifuged at 20,000 r.p.m. for 20 minutes at 4° C. The supernatant was discarded, and the pellet was resuspended in about 2 ml of A— buffer (50 mM TrisHCl, pH=8, and 10 mM KCl).

The 2 ml sample was then passed over a PD-10 (Sephadex G-25M; pre-packaged, 9 ml column marketed by Pharmacia P-L Biochemicals) column equilibrated with A— buffer, which was also used to elute the sample. The IPS-containing fractions were collected and used in the IPS assay described in Example 3 after determining protein content by the Bradford assay. The results of the assay are presented below in Table III.

| Culture | IPS in Sample (μg) | Zone Size (mm) | Isopenicillin N equivalents (μmoles) | Specific Activity IU*/mg IPS |
|---|---|---|---|---|
| RV308/pIT344WT | 0.43 | 13 | $1.7 \times 10^{-3}$ | $3.9 \times 10^{-1}$ |
| RV308/pIT347 | 37.5 | 21** | $4.3 \times 10^{-3}$ | $1.1 \times 10^{-2}$ |
| RV308/pIT349 | 0.97 | 18 | $3.4 \times 10^{-3}$ | $3.5 \times 10^{-1}$ |
| RV308/pIT352 | 63 | 0 | $<1.4 \times 10^{-3}$ | $<2.3 \times 10^{-3}$ |
| A85892 RV308/pIT344WT | 2.4 | 27 | $1.42 \times 10^{-2}$ | $5.9 \times 10^{-1}$ |
| A85892 RV308/pIT347 | 10 | 16 | $2.71 \times 10^{-3}$ | $2.7 \times 10^{-2}$ |
| A85892 RV308/pIT349 | 2.0 | 23 | $5.7 \times 10^{-3}$ | $2.85 \times 10^{-1}$ |
| A85892 RV308/pIT352 | 91 | 12 | $1.9 \times 10^{-3}$ | $4.2 \times 10^{-3}$ |

*The amount of protein necessary to condense 1 μmole of ACV to isopenicillin N in 1 minute at 25° C.
**Zone size depressed due to the activity of an inhibitor.

EXAMPLE 14

An Improved Transformation Procedure for *Cephalosporium acremonium*,

The *Cephalosporium acremonium* inoculum is prepared and a cell culture for transformation is obtained in accordance with the procedure described in Example 6.

A. Preparation of Protoplasts

Cells from a 24 hour culture are harvested by suction filtration (Whatman #1 paper in a Buchner funnel) and suspended in an osmotically stabilized buffer (0.8 M NaCl; 0.1 M MgSO₄; and 10 mM NaH₂PO₄, pH=7.0) to which the reducing agent dithiothreitol has been added to a concentration of 0.05 M. Sufficient buffer is added to obtain a final cell concentration of 1 g (weighed after suction filtration) of cell mass per 20 ml of buffer. The cell suspension is placed on a gyrotory water bath shaker in a 50 ml flask and incubated at 29°–30° C. for 10 minutes at 140 r.p.m. with a 1 inch throw. Alternatively, 2-mercaptoethanol, at a final concentration of 140 mM, may be used as a reducing agent. Dithiothreitol-treated cells are harvested by centrifugation and resuspended in an enzyme solution (10 mg/ml Novozym 234 from Novo Biolabs, Bagsvaerd, Denmark, 0.8 M NaCl, 0.1 M $MgSO_4$, 10 mM $NaH_2PO_4$, pH=5.8) in a 250 ml erlenmeyer flask. The final cell concentration is 1 g of treated cell mass per 10 ml of enzyme solution. The cell suspension is then placed on a gyrotory water bath shaker at 29°–30° C. for 15–30 minutes at 120 r.p.m. with a 1 inch throw. At the end of this period, the protoplast suspension is transferred to a disposable centrifuge tube and vortexed for 2–3 seconds to liberate protoplasts still associated with mycelial fragments. This digestion procedure produces a heterogenous population of protoplasts with respect to size. The largest protoplasts regenerate cell walls and transform at a higher frequency than smaller protoplasts. A population of protoplasts enriched for large protoplasts is harvested by centrifugation at 100Xg for 2 minutes in a table-top clinical centrifuge. The supernatant is discarded, and the pelleted protoplasts are washed by resuspension in the osmotically stabilized buffer (pH=7.0) and harvested by centrifugation (550Xg for 6 minutes). The washing procedure is repeated two times. The washed protoplasts are resuspended in a sufficient amount of 0.8 M NaCl to achieve a concentration of 2 to $3 \times 10^9$ protoplasts per ml, by hemacytometer count.

B. Transformation Procedure

For each plasmid to be transformed, a 0.1 ml suspension containing 1 to $5 \times 10^7$ protoplasts of Cepalosporium in 0.8 M NaCl, and 80 mM $CaCl_2$ is used. About 20 μg of transforming plasmid and polyethylene glycol 4000 (Baker, >40% w/v in water) are added to the suspension of protoplasts to achieve a transformation mixture volume of 1.1 ml. The mixture is incubated for 10 minutes at room temperature and then centrifuged at 100Xg for 5 minutes. The protoplasts are then vortexed back into suspension in the same liquid. Aliquots (0.1 ml) are delivered to the surface of Trypticase-Soy Agar medium (BBL) that has been enriched with 10.8% sucrose to osmotically stabilize the protoplasts. After incubation of the petri plates at 15° C. for 24 hours, 4 ml of liquified agar (0.41% w/v, at 42° C.) containing 0.8 M NaCl and sufficient hygromycin B to achieve a final concentration of 100 μg/ml are added to each petri plate. *C. acremonium* strains exhibiting slow growth rates due to extensive mutagenesis are subjected to a reduced level of hygromycin B during the selection procedure (i.e., 10 μg/ml final concentration). After the overlay has solidified, the petri plates are incubated at 25° C. in a humidified chamber. Transformant colonies of sufficient size to subculture are present after four to five days incubation; however, slower growing transformants may take as long as 8 days to develop. Abortive transformants are easily distinguished from stable transformants, because abortive transformants fail to grow upon subculture to fresh medium containing the original selective level of hygromycin B.

The foregoing description of the invention is exemplary only and modifications thereof may be made without departing from the scope of the invention which is to be limited only by the appended claims.

We claim:

1. An isolated DNA compound that encodes isopenicillin N synthetase from Cephalosporium.

2. The DNA compound of claim 1 that is the ~1.5 kb NcoI-BamHI restriction fragment of plasmid pIT335.

3. The DNA compound of claim 1, wherein the sequence of the coding strand is

```
5'-ATG GGT TCC GTT CCA GTT CCA GTG GCC AAC GTC CCC CGA
ATC GAT GTC TCG CCC CTA TTC GGC GAT GAC AAG GAG AAG AAG
CTC GAG GTA GCT CGC GCC ATC GAC GCC GCA TCG CGC GAC ACA
GGC TTC TTT TAC GCG GTG AAC CAC GGT GTC GAC CTG CCG TGG
CTC TCG CGC GAG ACG AAC AAA TTC CAC ATG AGC ATC ACG GAC
GAG GAG AAG TGG CAG CTC GCC ATC CGG GCC TAC AAC AAG GAG
CAC GAG TCC CAG ATC CGG GCG GGC TAC TAC CTG CCG ATC CCG
GGC AAG AAG GCG GTC GAA TCG TTC TGC TAC CTG AAC CCC TCC
TTC AGC CCA GAC CAC CCG CGA ATC AAG GAG CCC ACC CCT ATG
CAC GAG GTC AAC GTC TGG CCG GAC GAG GCG AAG CAC CCG GGG
TTC CGG GCC TTC GCC GAG AAG TAC TAC TGG GAC GTC TTC GGC
CTC TCC TCC GCG GTG CTG CGC GGC TAC GCT CTC GCC CTA GGT
CGC GAC GAG GAC TTC TTC ACC CGC CAC TCC CGC CGT GAC ACG
ACG CTC TCG TCG GTC GTG CTC ATC CGT TAC CCG TAC CTC GAC
CCG TAC CCG GAG CCG GCC ATC AAG ACG GCC GAC GAC GGC ACC
AAG CTC AGC TTC GAG TGG CAC GAG GAC GTG TCC CTC ATC ACG
GTG TTG TAC CAG TCC GAC GTG CAG ATT CTG CAG GTC AAG ACC
CCG CAG GGC TGG CAG GAC ATC CAG GCT GAC GAC ACG GGC TTC
CTC ATC AAC TGC GGC AGC TAC ATG GCC CAT ATC ACC GAC GAC
TAC TAC CCG GCC CCG ATC CAC CGC GTC AAA TGG GTC AAC GAG
GAG CGC CAG TCA CTG CCC TTC TTC GTC AAC CTG GGC TGG GAG
GAC ACC ATC CAG CCG TGG GAC CCC GCG ACC GCC AAG GAT GGG
GCC AAG GAT GCC GCC AAG GAC AAG CCG GCC ATC TCC TAC GGA
GAG TAT CTG CAG GGG GGA CTG CGG GGC TTG ATC AAC AAG AAT
GGT CAG ACC TAA-3'
``` wherein A is deoxyadenyl, G is deoxyguanyl, C is deoxycytidyl, and T is thymidyl.

4. The amino acid residue sequence:

```
MET GLY SER VAL PRO VAL PRO VAL ALA ASN VAL PRO ARG ILE
ASP VAL SER PRO LEU PHE GLY ASP ASP LYS GLU LYS LYS LEU
GLU VAL ALA ARG ALA ILE ASP ALA ALA SER ARG ASP THR GLY
```

-continued

```
PHE PHE TYR ALA VAL ASN HIS GLY VAL ASP LEU PRO TRP LEU
SER ARG GLU THR ASN LYS PHE HIS MET SER ILE THR ASP GLU
GLU LYS TRP GLN LEU ALA ILE ARG ALA TYR ASN LYS GLU HIS
GLU SER GLN ILE ARG ALA GLY TYR TYR LEU PRO ILE PRO GLY
LYS LYS ALA VAL GLU SER PHE X TYR LEU ASN PRO SER PHE
SER PRO ASP HIS PRO ARG ILE LYS GLU PRO THR PRO MET HIS
GLU VAL ASN VAL TRP PRO ASP GLU ALA LYS HIS PRO GLY PHE
ARG ALA PHE ALA GLU LYS TYR TYR TRP ASP VAL PHE GLY LEU
SER SER ALA VAL LEU ARG GLY TYR ALA LEU ALA LEU GLY ARG
ASP GLU ASP PHE PHE THR ARG HIS SER ARG ARG ASP THR THR
LEU SER SER VAL VAL LEU ILE ARG TRY PRO TYR LEU ASP PRO
TYR PRO GLU PRO ALA ILE LYS THR ALA ASP ASP GLY THR LYS
LEU SER PHE GLU TRP HIS GLU ASP VAL SER LEU ILE THR VAL
LEU TYR GLN SER ASP VAL GLN ASN LEU GLN VAL LYS THR PRO
GLN GLY TRP GLN ASP ILE GLN ALA ASP ASP THR GLY PHE LEU
ILE ASN Y GLY SER TYR MET ALA HIS ILE THR ASP ASP TYR
TYR PRO ALA PRO ILE HIS ARG VAL LYS TRP VAL ASN GLU GLU
ARG GLN SER LEU PRO PHE PHE VAL ASN LEU GLY TRP GLU ASP
THR ILE GLN PRO TRP ASP PRO ALA THR ALA LYS ASP GLY ALA
LYS ASP ALA ALA LYS ASP LYS PRO ALA ILE SER TYR GLY GLU
TYR LEU GLN GLY GLY LEU ARG GLY LEU ILE ASN LYS ASN GLY
GLN THR
``` wherein ALA is an alanine residue, ARG is an arginine residue, ASN is an asparagine residue, ASP is an aspartic acid residue, CYS is a cysteine residue, GLN is a glutamine residue, GLU is a glutamic acid residue, GLY is a glycine residue, HIS is a histidine reidue, ILE is an isoleucine residue, LEU is a leucine residue, LYS is a lysine residue, MET is a methionine residue, PHE is a phenylalanine residue, PRO is a proline residue, SER is a serine residue, THR is a threonine residue, TRP is a tryptophan residue, TYR is a tyrosine residue, and VAL is a valine residue, X is either CYS or SER, and Y is either CYS or SER.

5. An isolated DNA sequence that encodes the amino acid residue sequence of claim 4.

6. A recombinant DNA vector that comprises a DNA sequence of claim 5.

7. The recombinant DNA vector of claim 6 that is phage mIT111.

8. The recombinant DNA vector of claim 6 that is phage mIT112.

9. The recombinant DNA vector of claim 6 that is plasmid pIT347.

10. The recombinant DNA vector of claim 6 that is plasmid pIT349.

11. The recombinant DNA vector of claim 6 that is plasmid pIT352.

12. A recombinant DNA vector that comprises a DNA compound of claim 1.

13. A recombinant DNA vector that comprises a DNA compound of claim 2.

14. A recombinant DNA vector that comprises a DNA compound of claim 3.

15. The recombinant DNA vector of claim 13 that is a plasmid.

16. A plasmid of claim 15 selected from the group consisting of plasmids pIT335, pIT337, pPS20, and pPS20.1.

17. A plasmid of claim 15 selected from the group consisting of plasmids pPS47, pPS47.1, pPS48, pPS48.1, pIT344WT, and pIT344.1WT.

18. The vector of claim 14 that is phage mIT110.

19. An isolated DNA compound that comprises the *Cephalosporium acremonium* transcriptional and translational activating sequence of the isopenicillin N synthetase gene.

20. The DNA compound of claim 19 which is the ~0.5 kb SalI-NcoI restriction fragment of plasmid pIT335.

21. An isolated DNA compound that comprises the sequence

```
5'-CGAATACTTG AATATTCCTT GGTCGCTCTT CTGATTTTCG
   ||||||||||  ||||||||||  ||||||||||  ||||||||||
3'-GCTTATGAAC TTATAAGGAA CCAGCGAGAA GACTAAAAGC

AGGCTTCTCC TTCCGCCATC GTCGCCTCAC GCATATCTCG
   ||||||||||  ||||||||||  ||||||||||  ||||||||||
   TCCGAAGAGG AAGGCGGTAG CAGCGGAGTG CGTATAGAGC

TCTTTCACAT CTTACACCAG CAGGACAAAC CGTCACC-3'
   ||||||||||  ||||||||||  ||||||||||  |||||||
   AGAAAGTGTA GAATGTGGTC GTCCTGTTTG GCAGTGG-5'
``` wherein, A is deoxyadenyl, G is deoxguanyl, C is eoxycytidyl, and T is thymidyl.

22. A recombinant DNA vector that comprises the DNA compound of claim 19.

23. A recombinant DNA vector that comprises the DNA compound of claim 21.

24. The recombinant DNA vector of claim 22 that is a plasmid.

25. The plasmid of claim 24 selected from the group consisting of plasmids pPS22, pPS23, and pPS23.1.

26. The plasmid of claim 24 in which the *Cephalosporium acremonium*, transcriptional and translational activating sequence is positioned for expression of a DNA sequence that encodes a functional polypeptide.

27. The plasmid of claim 26, wherein said functional polypeptide is an antibiotic biosynthetic enzyme.

28. The plasmid of claim 26, wherein said functional polypeptide is an antibiotic resistance-conferring enzyme.

29. The plasmid of claim 28, wherein said antibiotic resistance-conferring enzyme confers resistance to hygromycin.

30. The plasmid of claim 29 selected from the group consisting of plasmids pPS21, pPS21A, pPS25, pPS25.1, pPS26, pPS26.1, pPS27, pPS28, pPS29, pPS30, pPS30.1, pPS31, pPS31.1, pPS34, pPS37, and pPS37.1.

31. An isolated DNA compound that encodes the transcription termination and mRNA polyadenylation and processing signals of the *Cephalosporium acremonium* IPS gene.

32. The DNA compound of claim 31 that is the 0.5 kb PstI-BamHI restriction fragment of plasmid pIT335.

33. A recombinant DNA vector that comprises the DNA compound of claim 31.

34. The recombinant DNA vector of claim 33 selected from the group consisting of plasmids pIT336 and pPS35.

35. A plasmid selected from the group consisting of plasmids pPS19 and pPS24.

36. A method of producing isopenicillin N synthetase activity in a host cell that comprises:
  (1) transforming said host cell with a recombinant DNA expression vector comprising a DNA compound of claim 1 positioned for expression from a transcriptional and translational activating sequence functional in said host cell; and
  (2) culturing said host cell transformed in step (1) under conditions that allow for expression of said DNA.

37. A method of producing isopenicillin N synthetase activity in a host cell which comprises:
  (1) transforming said host cell with a recombinant DNA expression vector comprising a DNA compound of claim 2 positioned for expression from a transcriptional and translational activating sequence functional in said host cell; and
  (2) culturing said host cell transformed in step (1) under conditions that allow for expression of said DNA.

38. A method of producing isopenicillin N synthetase activity in a host cell which comprises:
  (1) transforming said host cell with a recombinant DNA expression vector comprising a DNA compound of claim 3 positioned for expression from a transcriptional and translational activating sequence functional in said host cell; and
  (2) culturing said host cell transformed in step (1) under conditions that allow for expression of said DNA.

39. A method of producing isopenicillin N synthetase activity in a host cell that comprises:
  (1) transforming said host cell with a recombinant DNA expression vector comprising a DNA compound of claim 5 positioned for expression from a transcriptional and translational activating sequence functional in said host cell; and
  (2) culturing said host cell transformed in step (1) under conditions that allow for expression of said DNA.

40. The method of claim 36, wherein said host cell is selected from the group consisting of Agrobacterium, Cephalosporium, Chromobacterium, *E. coli*, Gluconobacter, Nocardia, Penicillium, Serratia, and Streptomyces.

41. The method of claim 37, wherein said host cell is selected from the group consisting of Agrobacterium, Cephalosporium, Chromobacterium, *E. coli*, Gluconobacter, Nocardia, Penicillium, Serratia, and Streptomyces.

42. The method of claim 38, wherein said host cell is selected from the group consisting of Agrobacterium, Cephalosporium, Chromobacterium, *E. coli*, Gluconobacter, Nocardia, Penicillium, Serratia, and Streptomyces.

43. The method of claim 39, wherein said host cell is selected from the group consisting of Agrobacterium, Cephalosporium, Chromobacterium, *E. coli*, Gluconobacter, Nocardia, Penicillium, Serratia, and Streptomyces.

44. The method of claim 40, wherein said host cell is *Cephalosporium acremonium*.

45. The method of claim 40, wherein said host cell is *Penicillium chrysogenum*.

46. The method of claim 40, wherein said host cell is *Streptomyces clavuligerus*.

47. The method of claim 40, wherein said host cell is *E. coli*.

48. The method of claim 41, wherein said recombinant DNA expression vector is plasmid pIT337.

49. The method of claim 41, wherein said recombinant DNA expression vector is plasmid pPS20.

50. The method of claim 47, wherein said *E. coli* is selected from the group consisting of *E. coli* K12 RV308 and *E. coli* K12 A85892.

51. A host cell transformed with a recombinant DNA vector of claim 12.

52. The transformed host cell of claim 51 that is *E. coli* K12/pIT335.

53. The host cell cultured in the method of claim 44 that is *Cephalosporium acremonium*/pPS47.

54. The host cell cultured in the method of claim 41 that is *E. coli*/pIT337.

55. The host cell cultured in the method of claim 41 that is *Cephalosporium acremonium*/pPS20.

56. The host cell cultured in the method of claim 50 that is *E. coli* K12 A85892/pIT344WT.

57. The host cell cultured in the method of claim 50 that is *E. coli* K12 A85892/pIT347.

58. The host cell cultured in the method of claim 50 that is *E. coli* K12 A85892/pIT349.

59. The host cell cultured in the method of claim 50 that is *E. coli* K12 A85892/pIT352.

60. A host cell transformed with a recombinant DNA vector of claim 19.

61. The transformed host cell of claim 60 that is *E. coli*.

62. The transformed *E. coli* host cell of claim 61 wherein the vector is selected from the group consisting of plasmids pPS21A, pPS25, pPS25.1, pPS26, pPS26.1, pPS27, pPS28, pPS29, pPS30, pPS30.1, pPS31, pPS31.1, pPS34, pPS37, and pPS37.1.

63. The transformed host cell of claim 60 that is *Cephalosporium acremonium*.

64. The transformed *Cephalosporium acremonium* host cell of claim 63 wherein the vector is selected from the group consisting of plasmids pPS21A, pPS25, pPS25.1, pPS26, pPS26.1, pPS27, pPS28, pPS29, pPS30, pPS30.1, pPS31, pPS31.1, pPS34, pPS37, and pPS37.1.

65. An isolated DNA compound that encodes a protein having IPS activity, said sequence capable of hybridization with the DNA compound of claim 2, or a portion thereof.

* * * * *